United States Patent
Greene et al.

(10) Patent No.: US 6,417,168 B1
(45) Date of Patent: Jul. 9, 2002

(54) COMPOSITIONS AND METHODS OF TREATING TUMORS

(75) Inventors: Mark I. Greene, Penn Valley; Donald M. O'Rourke, Wynnewood; Ramachandran Murali, Drexel Hill; Byeong-Woo Park, Wayne, all of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/111,681

(22) Filed: Jul. 8, 1998

Related U.S. Application Data

(60) Provisional application No. 60/076,788, filed on Mar. 4, 1998.

(51) Int. Cl.[7] .................................................. A01N 43/04

(52) U.S. Cl. ............................. 514/44; 514/44; 514/2; 514/21; 530/350; 530/300

(58) Field of Search ................................ 530/350, 300; 514/44, 2, 21

(56) References Cited

U.S. PATENT DOCUMENTS

| | | | |
|---|---|---|---|
| 5,200,178 A | 4/1993 | Strauss et al. | 424/1.1 |
| 5,367,060 A | 11/1994 | Vandlen et al. | 530/399 |
| 5,464,751 A | 11/1995 | Greene et al. | 435/7.23 |
| 5,470,571 A | 11/1995 | Herlyn et al. | 424/1.49 |
| 5,663,144 A | 9/1997 | Greene et al. | 514/14 |
| 5,677,171 A | 10/1997 | Hudziak et al. | 435/240.27 |
| 5,703,055 A | 12/1997 | Felgner et al. | 514/44 |
| 5,705,157 A | 1/1998 | Greene | 424/138.1 |
| 5,707,618 A | 1/1998 | Armentano et al. | 424/93.21 |
| 5,720,954 A | 2/1998 | Hudziak et al. | 424/130.1 |
| 5,725,856 A | 3/1998 | Hudziak et al. | 424/130.1 |
| 5,756,283 A | 5/1998 | Wilson et al. | 435/5 |
| 5,770,195 A | 6/1998 | Hudziak et al. | 424/130.1 |
| 5,772,997 A | 6/1998 | Hudziak et al. | 424/130.1 |
| 5,824,311 A | 10/1998 | Greene et al. | 424/138.1 |
| 5,837,523 A | 11/1998 | Greene et al. | 435/320.1 |
| 6,100,377 A | 8/2000 | Greene | 530/317 |

FOREIGN PATENT DOCUMENTS

| | | |
|---|---|---|
| WO | WO 95/30331 | 11/1995 |
| WO | WO 95/34312 | 12/1995 |
| WO | WO 96/34312 | 12/1995 |
| WO | WO 96/34617 | * 11/1996 |
| WO | WO 96/39530 | 12/1996 |
| WO | WO 99/44645 | 9/1999 |

OTHER PUBLICATIONS

Alignments.*

Balaban, N., et al., "The effect of ionizing radiation on signal transduction: antibodies to EGF receptor sensitize A431 cells to radiation," *Biochimica et Biophysica Acta*, 1996, 1314, 147–156.

Bach, A. et al., "Structural Studies of Family of High Affinity LIgands for $GP^{IIb/IIIa}$", *New Adv. Peptidomimetics Small Mol. Design* 1994, 1, 1–26.

Bargmann, C. et al., "The Neu Oncogene Encodes an Epidermal Growth Factor Receptor–Related Protein", *Nature* 1986, 319, 226–230.

Bargmann, C. and Weinberg, R., "Increased tyrosine kinase activity associated with the protein encoded by the activated neu oncogene", *Proc. Natl. Acad. Sci. USA* 1988, 85, 5394–5398.

Bookman, M.A. et al., "Immunotoxins Directed Against c–erbB2: Limited Activity Due to Poor Internalization", *3rd International Symposium on Immunotoxins*, 1992, p. 15.

Di Blasio et al., "Noncoded Residues as Building Block in the Design of Specific Secondary Structures: Symmetrically Disubstituted Glycines and β–Alanine", *Biopolymers* 1993, 33, 1037–1049.

Dougall, W. et al., "Modulation of $p185^{c-erB-2}$ Expression and Tumorigenic Growth by Anti–receptor Monoclonal Antibodies", *J. of Cellular Biochem.* 1994, Supplement 18D, No. Y 507, p. 252.

Drebin et al., "Down–Modulation of an Oncogene Protein Product and Reversion of the Transformed Phenotype by Monoclonal Antibodies", *Cell* 1985, 41, 695–706.

Drebin, J. et al., "Inhibition of Tumor Growth by a Mono-clonal Antibody reactive with an Oncogene–Encoded Tumor Antigen", *PNAS USA* 1986, 83, 9129–9133.

Drebin, J. et al., "Monoclonal Antibodies Reactive with Distinct Domains of the Neu Oncogene–Encoded p185 Molecule Exert Synergistic Anti–Tumor Effects in Vivo", *Oncogene* 1988, 2, 273–277.

Hruby, V.J. et al., "Conformational and Topographical Considerations in the Design of Biologically Active Peptides", *Biopolymers* 1993, 33, 1073–1082.

Lodato, R.F. et al., "Immunohistochemical Evaluation of c–erbB–2 Oncogene Expression in Ductal Carcinoma In Situ and Atypical Ductal Hyperplasia of the Breast", *Modern Pathol.* 1990, 3(4), 449–454.

Manning,M. et al., "Design of cyclic and linear peptide antagonists of vasopression and oxytocin: current status and future directions", *Regulatory Peptides* 1993, 45, 279–283.

Matsuyama, T. et al., A Novel Extracellular Cyclic Lipopeptide Which Promotes Glagellum–Dependent and—Independent Spreading Growth of *Serratia marcescens, J. of Bacteriology* 1992, 174, 1769–1776.

(List continued on next page.)

Primary Examiner—Karen Cochrane Carlson
Assistant Examiner—Hope A. Robinson
(74) Attorney, Agent, or Firm—Woodcock Washburn LLP

(57) ABSTRACT

Methods of treating an individual who has an erbB protein mediated tumor is disclosed. Methods of preventing erbB protein mediated tumors in an individual are disclosed. The methods comprise administering to the individual a nucleic acid molecule that encodes a protein that dimerizes with an erbB protein and that is deficient in tyrosine kinase activity. Composition that comprise such nucleic acid molecules including pharmaceutical compositions are disclosed.

29 Claims, 4 Drawing Sheets

OTHER PUBLICATIONS

Saragovi, H. et al., "Design and Synthesis of a Mimetic from an Antibody Complementarity–determining Region", *Science* 1991, 253, 792–795.

Saragovi, H., "Constrained Peptides and Mimetics as Probes of Protein Secondary Structure", *Immunomethods* 1992, 1, 5–9.

Slamon, D.J., "Role of the HEr–2/neu Gene in Human Breast and Ovarian Cancer", Meeting of the American Association of Clinical Research, 1992.

Wada, T. et al., "Anti–receptor Antibodies Reverse the Phenotype of Cells Transformed by Two Interacting Proto–oncogene Encoded Receptor Proteins", *Oncogene* 1990, 5, 489–495.

Wood, S. and Wetzel, "Novel Cyclization Chemistry Especially Suited for Biologically Derived, Unprotected Peptides", *Int. J. Peptide Protein Res.* 1992, 39, 533–539.

Wright, C. et al., "Expression of c–erbB–2 Oncoprotein: A Prognostic Indicator in Human Breast Cancer", *Cancer*.

Rudinger, J., "Characteristics of the amino acids as components of a peptide hormone sequence", Peptide Hormones, 1976, J.A. Parsons, ed., University Park Press, Baltimore, pp. 1–7.

Borgelt et al., "The Palliation of Brain Metastases: Final Results of the First Two Studies by the Radiation Therapy Oncology Group", *Int. J. Radiat. Oncol. Biol., Int. Phys.*, 1980, 6, 1–9.

Simpson, J.R., et al., "Influence of Location and Extent of Surgical Resection on Survival of Patients with Glioblastoma Multiforme: Results of Three Consecutive Radiation Therapy Oncology Group (RTOG) Clinical Trails", *Int. J. Radiation Oncology Biol. Phys.*, 1993, 26, 239–244.

Alaoui–Jamali, M.A. et al., "The role of ErbB–2 tyrosine kinase receptor in cellular intrinsic chemoresistance: mechanisms and implications," *Biochem. Cell Biol.*, 1997, 75(4), 315–325.

Messerle, K. et al., "NIH/3T3 cells transformed with the activated erbB–2 oncogene can be potentially reverted by a kinase deficient, dominant negative erbB–2 variant," *Mol. Cell. Endocrinology*, 1994, 105(1), 1–10.

O'Rourke, D.M. et al., "Trans receptor inhibition of human glioblastoma cells by erbB family ectodomains," *Proc. Natl. Acad. Sci. USA*, 1997, 94, 3250–3225.

Yen, L. et al., "Regulation of cellular response to cisplatin–induced DNA damage and DNA repair in cells in overexpressing $p185^{erbB-2}$ is dependent on the ras signaling pathway," *Oncogene*, 1997, 14(15), 1827–1835.

Qian, X. et al., "Heterodimerization of epidermal growth factor receptor and wild–type or kinase–deficient Neu: A mechanism of interreceptor kinase activation and transphosphorylation," *Proc. Natl. Acad. Sci. USA*, 1994, 91(4), 1500–1504.

Qian, X. et al., "Inhibition of $p185^{neu}$ kinase activity and cellular tranformation by co–expression of a truncated neu protein," *Oncogene*, 1996, 13, 2149–2157.

Carraway, K.L., et al., "A neu acquaintance for ErbB3 and ErbB4: A role for receptor heterodimerization in growth signaling, " *Cell*, 1994, 78, 5–8.

Chazin, V.R., et al., "Transformation Mediated by the human HER–2 gene independent of the epidermal growth factor receptor, " *Oncogene*, 1992, 7, 1859–1866.

DiFiore, P.P., et al., "erbB–2 is a potent oncogene when overexpressed in NIH/3T3 cells, " *Science*, 1987, 237, 178–182.

DiFiore, P.P., et al., "Overexpression of the human EGF receptor confers and EGF–dependent transformed phenotype to NIH 3T3 cells, " *Cell*, 1987, 51, 1063–1070.

DiMarco, et al., "Transformation of NIG 3T3 cells by overexpression of the normal coding sequence of the rat neu gene, " *Mol. Cell. Biol.*, 1990, 10(6), 3247–3252.

Dougall, et al., "Interaction of the Neu/p185 and EGF receptor tyrosine kinases: implications for cellular transformation and tumor therapy, " *J. Cell. Biochem.*, 1993, 53, 61–73.

Goldman, M.J. et al., "Transfer of the CFTR gene to the lung of nonhuman primates with E1–deleted, E2a–defective recombinant adenoviruses: a preclinical toxicology study, " *Hum. Gene Ther.*, 1995, 6, 839–851.

King, C.R., et al., "EGF binding to its receptor triggers a rapid tyrosine phosphorlylation of the erbB–2 protein in the mammary tumor cell line SK–BR–3, " *EMBO J.*, 1988, 7, 1647–1651.

Kokai, Y., et al., "Synergistic interaction of the p185c–neu and EGF receptor leads to transformation of rodent fibroblasts, " *Cell*, 1989, 58, 287–292.

Kraus, M.H., et al., "Isolation and characterization of ERBB3, a third member of the ERBB/epidermal growth factor receptor family: evidence for overexpression in a subset of human mammary tumors, " *Proc. Natl. Acad. Sci.*, 1989, 86, 9193–9197.

Lofts, E.J., et al., "Specific short transmembrane sequences can inhibit transformation by the mutant NEU growth factor receptor in vitro and in vivo, " *Oncogene*, 1993, 8, 2813–2820.

Pinkas–Kramarski, R., et al., "Differential expression of NDF/neuregulin receptors ErbB–3 and ErbB–4 and involvement in inhibition of neuronal differentiation, " *Oncogene*, 1997, 15, 2803–2815.

Plowman, G.D., et al., "Ligand–specific activation of HER4/$p180^{erbB4}$, a fourth member of the epidermal growth factor receptor family, " *Proc. Natl. Acad. Sci.*, 1993, 90, 1746–1750.

Qian, X., "$p185^{c-neu}$ and epidermal growth factor receptor associate into a structure composed of activated kinases, " *Proc. Natl. Acad. Sci. USA*, 1992, 89, 1330–1334.

Riese, D.J., et al., "The cellular response to neuregulins is governed by complex interactions of the erbB receptor family, " *Mol. Cell. Biol.*, 1995, 15(10), 5770–5776.

Schechter, A.L., et al., "The Neu Oncogene: an erb–B related gene encoding a 185,000–$M_r$, tumor antigen, " *Nature*, 1984, 312, 513–516.

Slamon, D.J., et al., "Human breast cancer: correlation of relapse and survival with amplification of the HER–2/neu oncogene, " *Science*, 1987, 235, 177–182.

Spivak–Kroizman, T., et al., "Heterodimerizatrion of c–erbB–2 with different epidermal growth factor receptor mutants elicits stimulatory or inhibitory responses, " *J. Biol. Chem.*, 1992, 267(12), 8056–8063.

Stern, D.F., et al., "Oncogenic activation of $p185^{neu}$ stimulates tyrosine phosphorylation in vivo, " *Mol. Cell. Biol.*, 1988, 8(9), 3969–3937.

Sugawa, N., et al., "Identical splicing of aberrant epidermal growth factor receptor transcripts from amplified rearranged genes in human glioblastomas, " *Proc. Natl. Acad. Sci.*, 1990, 87, 8602–8606.

Tzahar, E., et al., "Bivalence of EGF–like ligands drives the ErbB signaling network, " *EMBO J.*, 1997, 16(16), 4938–4950.

Ulrich, A., et al., "Human epidermal growth factor receptor cDNA sequence and aberrant expression of the amplified gene in A431 epidermoid carcinoma cells," *Nature*, 1984, 309, 418–425.

Wada, T., et al., "Intermolecular association of the p185$^{neu}$ protein and EGF receptor modulates EGF receptor function," *Cell*, 1990, 61, 1339–1347.

Weiner, D.B. et al., "Linkage of tyrosine kinase activity with transforming ability of the p185neu oncoprotein," *Oncogene*, 1989, 4, 1175–1183.

Yamamoto, T., et al., "Similarity of protein encoded by the human c–erb–B–2 gene to epidermal growth factor receptor," *Nature*, 1986, 319, 230–234.

U.S patent application Ser. No. 08/525,800, Greene et al., filed Nov. 11, 1995.

U.S. patent application Ser. No. 08/239,202, Greene et al., filed May 5, 1994.

* cited by examiner

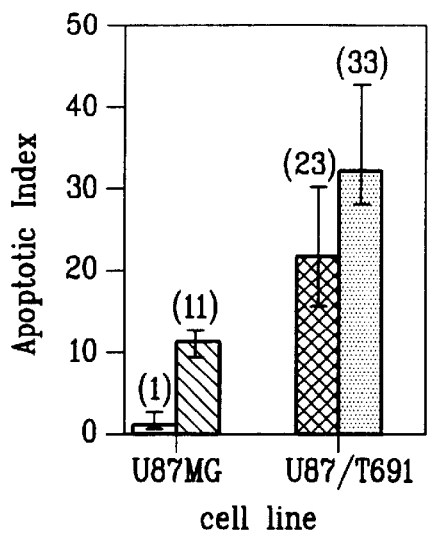
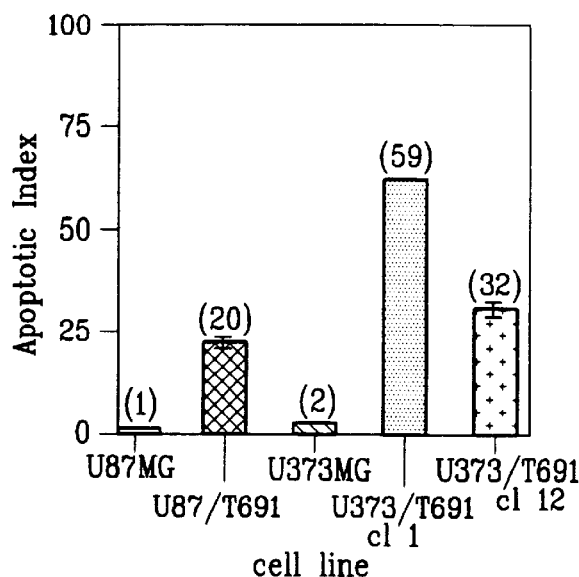
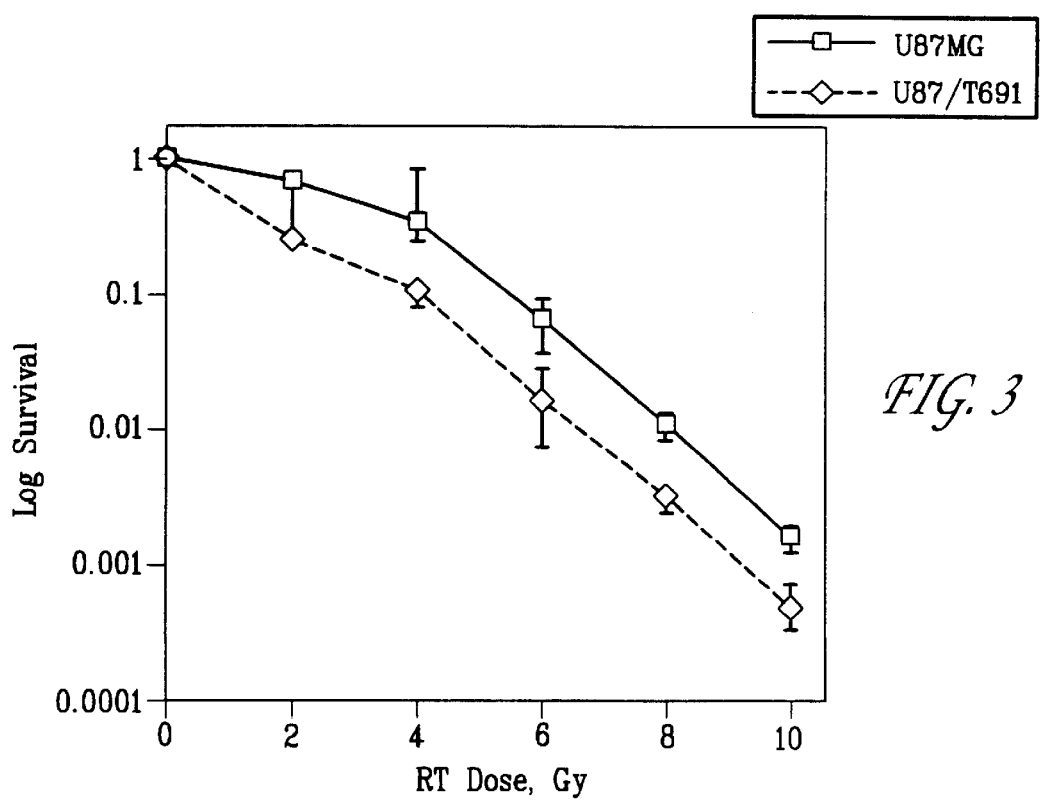

SEQUENCE LISTING

<160> NUMBER OF SEQ ID NOS: 200

<210> SEQ ID NO 1
<211> LENGTH: 13
<212> TYPE: PRT
<213> ORGANISM: Artificial Sequence
<220> FEATURE:
<223> OTHER INFORMATION: Synthetic Sequence
<221> NAME/KEY: MOD_RES
<222> LOCATION: (13)..(13)

<223> OTHER INFORMATION: AMIDATION

<400> SEQUENCE: 1

Phe Cys Gly Asp Gly Phe Tyr Ala Cys Tyr Met Asp Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Sequence
<221> NAME/KEY: MOD_RES
<222> LOCATION: (12)..(12)
<223> OTHER INFORMATION: AMIDATION

<400> SEQUENCE: 2

Phe Cys Asp Gly Phe Tyr Ala Cys Tyr Met Asp Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Sequence
<221> NAME/KEY: MOD_RES
<222> LOCATION: (12)..(12)
<223> OTHER INFORMATION: AMIDATION

<400> SEQUENCE: 3

Phe Cys Asp Pro Phe Tyr Ala Cys Tyr Met Asp Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Sequence
<221> NAME/KEY: MOD_RES
<222> LOCATION: (13)..(13)
<223> OTHER INFORMATION: AMIDATION

<400> SEQUENCE: 4

Phe Cys Pro Asp Gly Phe Tyr Ala Cys Tyr Met Asp Val
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Sequence
<221> NAME/KEY: MOD_RES
<222> LOCATION: (13)..(13)
<223> OTHER INFORMATION: AMIDATION

<400> SEQUENCE: 5

Phe Cys Asp Pro Pro Phe Tyr Ala Cys Tyr Met Asp Val
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Sequence
<221> NAME/KEY: MOD_RES

```
<222> LOCATION: (12)..(12)
<223> OTHER INFORMATION: AMIDATION

<400> SEQUENCE: 6

Phe Cys Asp Gly Phe Tyr Ala Cys Tyr Met Asp Val
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Sequence
<221> NAME/KEY: MOD_RES
<222> LOCATION: (12)..(12)
<223> OTHER INFORMATION: AMIDATION

<400> SEQUENCE: 7

Phe Cys Asp Pro Phe Tyr Ala Cys Tyr Met Asp Val
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic Sequence
<221> NAME/KEY: MOD_RES
<222> LOCATION: (13)..(13)
<223> OTHER INFORMATION: AMIDATION

<400> SEQUENCE: 8

Phe Cys Asp Pro Pro Phe Tyr Ala Cys Tyr Met Asp Val
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 9

Phe Cys Gly Asp Gly Phe Tyr Ala Cys Tyr Met Asp Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 10

Phe Cys Asp Gly Phe Tyr Ala Cys Tyr Met Asp Val
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 11

Phe Cys Asp Pro Phe Tyr Ala Cys Tyr Met Asp Val
1               5                   10
```

<210> SEQ ID NO 12
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 12

Phe Cys Pro Asp Gly Phe Tyr Ala Cys Tyr Met Asp Val
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 13

Phe Cys Asp Pro Pro Phe Tyr Ala Cys Tyr Met Asp Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 14

Phe Cys Asp Gly Phe Tyr Ala Cys Tyr Met Asp Val
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 15

Phe Cys Asp Pro Phe Tyr Ala Cys Tyr Met Asp Val
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 16

Phe Cys Asp Pro Pro Phe Tyr Ala Cys Tyr Met Asp Val
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 17

Phe Lys Thr Asn Lys
1               5

```
<210> SEQ ID NO 18
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 18

Glu Asn Trp Asp Trp Tyr
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 19

Asp Asn Trp Asp Trp Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 20

Glu Gln Trp Asp Trp Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 21

Asp Gln Trp Asp Trp Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 22

Glu Asn Trp Glu Trp Tyr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 23

Asp Asn Trp Glu Trp Tyr
1               5

<210> SEQ ID NO 24
```

```
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 24

Glu Gln Trp Glu Trp Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 25

Asp Gln Trp Glu Trp Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 26

Glu Asn Trp Asp Trp Phe
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 27

Asp Asn Trp Asp Trp Phe
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 28

Glu Gln Trp Asp Trp Phe
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 29

Asp Gln Trp Asp Trp Phe
1               5

<210> SEQ ID NO 30
<211> LENGTH: 6
```

```
<212> TYPE: PRT
<213> ORGANISM: Artificial Sequence
<220> FEATURE:
<223> OTHER INFORMATION: Synthetic Sequence

<400> SEQUENCE: 30

Glu Asn Trp Glu Trp Phe
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 31

Asp Asn Trp Glu Trp Phe
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 32

Glu Gln Trp Glu Trp Phe
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 33

Asp Gln Trp Glu Trp Phe
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Sequence
<221> NAME/KEY: misc_feature
<222> LOCATION: (1)..(1)
<223> OTHER INFORMATION: Xaa is Gly, Val, Ala, Ile or Leu
<221> NAME/KEY: misc_feature
<222> LOCATION: (2)..(2)
<223> OTHER INFORMATION: Xaa is Asp or Glu
<221> NAME/KEY: misc_feature
<222> LOCATION: (3)..(3)
<223> OTHER INFORMATION: Xaa is Gly, Val, Ala, Ile or Leu
<221> NAME/KEY: misc_feature
<222> LOCATION: (4)..(4)
<223> OTHER INFORMATION: Xaa is Phe or Tyr
<221> NAME/KEY: misc_feature
<222> LOCATION: (5)..(5)
<223> OTHER INFORMATION: Xaa is Tyr or Phe
<221> NAME/KEY: misc_feature
<222> LOCATION: (6)..(6)
<223> OTHER INFORMATION: Xaa is Ala, Gly, Val, Ile or Leu

<400> SEQUENCE: 34

Xaa Xaa Xaa Xaa Xaa Xaa
1               5
```

<210> SEQ ID NO 35
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 35

Gly Asp Gly Phe Tyr Ala
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 36

Gly Glu Gly Phe Tyr Ala
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 37

Gly Asp Gly Tyr Tyr Ala
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 38

Gly Glu Gly Tyr Tyr Ala
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 39

Gly Asp Gly Phe Phe Ala
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 40

Gly Glu Gly Phe Phe Ala
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 41

Gly Asp Gly Tyr Phe Ala
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 42

Gly Glu Gly Tyr Phe Ala
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 43

Ala Asp Gly Phe Tyr Ala
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 44

Ala Glu Gly Phe Tyr Ala
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 45

Ala Asp Gly Tyr Tyr Ala
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 46

Ala Glu Gly Tyr Tyr Ala
1               5

```
<210> SEQ ID NO 47
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 47

Ala Asp Gly Phe Phe Ala
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 48

Ala Glu Gly Phe Phe Ala
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 49

Ala Asp Gly Tyr Phe Ala
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 50

Ala Glu Gly Tyr Phe Ala
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 51

Gly Asp Ala Phe Tyr Ala
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 52

Gly Glu Ala Phe Tyr Ala
1               5

<210> SEQ ID NO 53
```

```
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 53

Gly Asp Ala Tyr Tyr Ala
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 54

Gly Glu Ala Tyr Tyr Ala
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 55

Gly Asp Ala Phe Phe Ala
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 56

Gly Glu Ala Phe Phe Ala
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 57

Gly Asp Ala Tyr Phe Ala
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 58

Gly Glu Ala Tyr Phe Ala
1               5

<210> SEQ ID NO 59
<211> LENGTH: 6
```

```
<212> TYPE: PRT
<213> ORGANISM: Artificial Sequence
<220> FEATURE:
<223> OTHER INFORMATION: Synthetic Sequence

<400> SEQUENCE: 59

Ala Asp Ala Phe Tyr Ala
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 60

Ala Glu Ala Phe Tyr Ala
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 61

Ala Asp Ala Tyr Tyr Ala
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 62

Ala Glu Ala Tyr Tyr Ala
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 63

Ala Asp Ala Phe Phe Ala
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 64

Ala Glu Ala Phe Phe Ala
1               5

<210> SEQ ID NO 65
<211> LENGTH: 6
<212> TYPE: PRT
```

```
<213> ORGANISM: Artificial Sequence
<220> FEATURE:
<223> OTHER INFORMATION: Synthetic Sequence

<400> SEQUENCE: 65

Ala Asp Ala Tyr Phe Ala
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 66

Ala Glu Ala Tyr Phe Ala
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 67

Gly Asp Gly Phe Tyr Gly
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 68

Gly Glu Gly Phe Tyr Gly
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 69

Gly Asp Gly Tyr Tyr Gly
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 70

Gly Glu Gly Tyr Tyr Gly
1               5

<210> SEQ ID NO 71
<211> LENGTH: 6
<212> TYPE: PRT
<213> ORGANISM: Artificial Sequence
```

```
<220> FEATURE:
<223> OTHER INFORMATION: Synthetic Sequence

<400> SEQUENCE: 71

Gly Asp Gly Phe Phe Gly
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 72

Gly Glu Gly Phe Phe Gly
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 73

Gly Asp Gly Tyr Phe Gly
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 74

Gly Glu Gly Tyr Phe Gly
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 75

Ala Asp Gly Phe Tyr Gly
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 76

Ala Glu Gly Phe Tyr Gly
1               5

<210> SEQ ID NO 77
<211> LENGTH: 6
<212> TYPE: PRT
<213> ORGANISM: Artificial Sequence
<220> FEATURE:
```

<223> OTHER INFORMATION: Synthetic Sequence

<400> SEQUENCE: 77

Ala Asp Gly Tyr Tyr Gly
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 78

Ala Glu Gly Tyr Tyr Gly
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 79

Ala Asp Gly Phe Phe Gly
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 80

Ala Glu Gly Phe Phe Gly
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 81

Ala Asp Gly Tyr Phe Gly
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 82

Ala Glu Gly Tyr Phe Gly
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic Sequence

```
<400> SEQUENCE: 83

Gly Asp Ala Phe Tyr Gly
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 84

Gly Glu Ala Phe Tyr Gly
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 85

Gly Asp Ala Tyr Tyr Gly
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 86

Gly Glu Ala Tyr Tyr Gly
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 87

Gly Asp Ala Phe Phe Gly
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 88

Gly Glu Ala Phe Phe Gly
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic Sequence
```

```
<400> SEQUENCE: 89

Gly Asp Ala Tyr Phe Gly
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 90

Gly Glu Ala Tyr Phe Gly
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 91

Ala Asp Ala Phe Tyr Gly
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 92

Ala Glu Ala Phe Tyr Gly
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 93

Ala Asp Ala Tyr Tyr Gly
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 94

Ala Glu Ala Tyr Tyr Gly
1               5

<210> SEQ ID NO 95
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 95
```

Ala Asp Ala Phe Phe Gly
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 96

Ala Glu Ala Phe Phe Gly
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 97

Ala Asp Ala Tyr Phe Gly
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 98

Ala Glu Ala Tyr Phe Gly
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 99

Tyr Pro Pro Gly Cys
1               5

<210> SEQ ID NO 100
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 100

Tyr Met Asp Val
1

<210> SEQ ID NO 101
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 101

```
Phe Glu Cys Glu Asn Trp Asp Trp Tyr Cys Tyr Pro Pro Gly Cys
1               5                   10                  15
```

<210> SEQ ID NO 102
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 102

```
Phe Cys Gly Asp Gly Phe Tyr Ala Cys Met Asp Val
1               5                   10
```

<210> SEQ ID NO 103
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 103

```
Phe Glu Cys Asp Asn Trp Asp Trp Tyr Cys Tyr Pro Pro Gly Cys
1               5                   10                  15
```

<210> SEQ ID NO 104
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 104

```
Phe Glu Cys Glu Gln Trp Asp Trp Tyr Cys Tyr Pro Pro Gly Cys
1               5                   10                  15
```

<210> SEQ ID NO 105
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 105

```
Phe Glu Cys Asp Gln Trp Asp Trp Tyr Cys Tyr Pro Pro Gly Cys
1               5                   10                  15
```

<210> SEQ ID NO 106
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 106

```
Phe Glu Cys Glu Asn Trp Glu Trp Tyr Cys Tyr Pro Pro Gly Cys
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 107

```
Phe Glu Cys Asp Asn Trp Glu Trp Tyr Cys Tyr Pro Pro Gly Cys
```

```
1               5               10              15
```

<210> SEQ ID NO 108
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 108

```
Phe Glu Cys Glu Gln Trp Glu Trp Tyr Cys Tyr Pro Pro Gly Cys
1               5                   10                  15
```

<210> SEQ ID NO 109
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 109

```
Phe Glu Cys Asp Gln Trp Glu Trp Tyr Cys Tyr Pro Pro Gly Cys
1               5                   10                  15
```

<210> SEQ ID NO 110
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 110

```
Phe Glu Cys Glu Asn Trp Asp Trp Phe Cys Tyr Pro Pro Gly Cys
1               5                   10                  15
```

<210> SEQ ID NO 111
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 111

```
Phe Glu Cys Asp Asn Trp Asp Trp Phe Cys Tyr Pro Pro Gly Cys
1               5                   10                  15
```

<210> SEQ ID NO 112
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 112

```
Phe Glu Cys Glu Gln Trp Asp Trp Phe Cys Tyr Pro Pro Gly Cys
1               5                   10                  15
```

<210> SEQ ID NO 113
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 113

```
Phe Glu Cys Asp Gln Trp Asp Trp Phe Cys Tyr Pro Pro Gly Cys
1               5                   10                  15
```

<210> SEQ ID NO 114
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 114

Phe Glu Cys Glu Asn Trp Glu Trp Phe Cys Tyr Pro Pro Gly Cys
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 115

Phe Glu Cys Asp Asn Trp Glu Trp Phe Cys Tyr Pro Pro Gly Cys
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 116

Phe Glu Cys Glu Gln Trp Glu Trp Phe Cys Tyr Pro Pro Gly Cys
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 117

Phe Glu Cys Asp Gln Trp Glu Trp Phe Cys Tyr Pro Pro Gly Cys
1               5                   10                  15

<210> SEQ ID NO 118
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 118

Phe Cys Glu Asn Trp Asp Trp Tyr Cys Tyr Pro Pro Gly Cys
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 119

Phe Cys Asp Asn Trp Asp Trp Tyr Cys Tyr Pro Pro Gly Cys
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 120

Phe Cys Glu Gln Trp Asp Trp Tyr Cys Tyr Pro Pro Gly Cys
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 121

Phe Cys Asp Gln Trp Asp Trp Tyr Cys Tyr Pro Pro Gly Cys
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 122

Phe Cys Glu Asn Trp Glu Trp Tyr Cys Tyr Pro Pro Gly Cys
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 123

Phe Cys Asp Asn Trp Glu Trp Tyr Cys Tyr Pro Pro Gly Cys
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 124

Phe Cys Glu Gln Trp Glu Trp Tyr Cys Tyr Pro Pro Gly Cys
1               5                   10

<210> SEQ ID NO 125
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 125

Phe Cys Asp Gln Trp Glu Trp Tyr Cys Tyr Pro Pro Gly Cys
1               5                   10

```
<210> SEQ ID NO 126
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 126

Phe Cys Glu Asn Trp Asp Trp Phe Cys Tyr Pro Pro Gly Cys
1               5                   10

<210> SEQ ID NO 127
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 127

Phe Cys Asp Asn Trp Asp Trp Phe Cys Tyr Pro Pro Gly Cys
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 128

Phe Cys Glu Gln Trp Asp Trp Phe Cys Tyr Pro Pro Gly Cys
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 129

Phe Cys Asp Gln Trp Asp Trp Phe Cys Tyr Pro Pro Gly Cys
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 130

Phe Cys Glu Asn Trp Glu Trp Phe Cys Tyr Pro Pro Gly Cys
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 131

Phe Cys Asp Asn Trp Glu Trp Phe Cys Tyr Pro Pro Gly Cys
1               5                   10

<210> SEQ ID NO 132
```

```
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 132

Phe Cys Glu Gln Trp Glu Trp Phe Cys Tyr Pro Pro Gly Cys
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 133

Phe Cys Asp Gln Trp Glu Trp Phe Cys Tyr Pro Pro Gly Cys
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 134

Phe Glu Cys Glu Asn Trp Asp Trp Tyr Cys Tyr
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 135

Phe Glu Cys Asp Asn Trp Asp Trp Tyr Cys Tyr
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 136

Phe Glu Cys Glu Gln Trp Asp Trp Tyr Cys Tyr
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 137

Phe Glu Cys Asp Gln Trp Asp Trp Tyr Cys Tyr
1               5                   10

<210> SEQ ID NO 138
<211> LENGTH: 11
```

<212> TYPE: PRT
<213> ORGANISM: Artificial Sequence
<220> FEATURE:
<223> OTHER INFORMATION: Synthetic Sequence

<400> SEQUENCE: 138

Phe Glu Cys Glu Asn Trp Glu Trp Tyr Cys Tyr
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 139

Phe Glu Cys Asp Asn Trp Glu Trp Tyr Cys Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 140

Phe Glu Cys Glu Gln Trp Glu Trp Tyr Cys Tyr
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 141

Phe Glu Cys Asp Gln Trp Glu Trp Tyr Cys Tyr
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 142

Phe Glu Cys Glu Asn Trp Asp Trp Phe Cys Tyr
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 143

Phe Glu Cys Asp Asn Trp Asp Trp Phe Cys Tyr
1               5                   10

<210> SEQ ID NO 144
<211> LENGTH: 11
<212> TYPE: PRT

```
<213> ORGANISM: Artificial Sequence
<220> FEATURE:
<223> OTHER INFORMATION: Synthetic Sequence

<400> SEQUENCE: 144

Phe Glu Cys Glu Gln Trp Asp Trp Phe Cys Tyr
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 145

Phe Glu Cys Asp Gln Trp Asp Trp Phe Cys Tyr
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 146

Phe Glu Cys Glu Asn Trp Glu Trp Phe Cys Tyr
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 147

Phe Glu Cys Asp Asn Trp Glu Trp Phe Cys Tyr
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 148

Phe Glu Cys Glu Gln Trp Glu Trp Phe Cys Tyr
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 149

Phe Glu Cys Asp Gln Trp Glu Trp Phe Cys Tyr
1               5                   10

<210> SEQ ID NO 150
<211> LENGTH: 10
<212> TYPE: PRT
<213> ORGANISM: Artificial Sequence
```

-continued

```
<220> FEATURE:
<223> OTHER INFORMATION: Synthetic Sequence

<400> SEQUENCE: 150

Phe Cys Glu Asn Trp Asp Trp Tyr Cys Tyr
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 151

Phe Cys Asp Asn Trp Asp Trp Tyr Cys Tyr
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 152

Phe Cys Glu Gln Trp Asp Trp Tyr Cys Tyr
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 153

Phe Cys Asp Gln Trp Asp Trp Tyr Cys Tyr
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 154

Phe Cys Glu Asn Trp Glu Trp Tyr Cys Tyr
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 155

Phe Cys Asp Asn Trp Glu Trp Tyr Cys Tyr
1               5                   10

<210> SEQ ID NO 156
<211> LENGTH: 10
<212> TYPE: PRT
<213> ORGANISM: Artificial Sequence
<220> FEATURE:
```

<223> OTHER INFORMATION: Synthetic Sequence

<400> SEQUENCE: 156

Phe Cys Glu Gln Trp Glu Trp Tyr Cys Tyr
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 157

Phe Cys Asp Gln Trp Glu Trp Tyr Cys Tyr
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 158

Phe Cys Glu Asn Trp Asp Trp Phe Cys Tyr
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 159

Phe Cys Asp Asn Trp Asp Trp Phe Cys Tyr
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 160

Phe Cys Glu Gln Trp Asp Trp Phe Cys Tyr
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 161

Phe Cys Asp Gln Trp Asp Trp Phe Cys Tyr
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic Sequence

```
<400> SEQUENCE: 162

Phe Cys Glu Asn Trp Glu Trp Phe Cys Tyr
 1               5                  10

<210> SEQ ID NO 163
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 163

Phe Cys Asp Asn Trp Glu Trp Phe Cys Tyr
 1               5                  10

<210> SEQ ID NO 164
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 164

Phe Cys Glu Gln Trp Glu Trp Phe Cys Tyr
 1               5                  10

<210> SEQ ID NO 165
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 165

Phe Cys Asp Gln Trp Glu Trp Phe Cys Tyr
 1               5                  10

<210> SEQ ID NO 166
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 166

Phe Glu Cys Asp Asn Trp Asp Trp Tyr Cys Tyr Pro Pro Gly Cys
 1               5                  10                  15

<210> SEQ ID NO 167
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 167

Phe Glu Cys Glu Gln Trp Asp Trp Tyr Cys Tyr Pro Pro Gly Cys
 1               5                  10                  15

<210> SEQ ID NO 168
<211> LENGTH: 15
<212> TYPE: PRT
<213> ORGANISM: Artificial Sequence
<220> FEATURE:
<223> OTHER INFORMATION: Synthetic Sequence
```

```
<400> SEQUENCE: 168

Phe Glu Cys Asp Gln Trp Asp Trp Tyr Cys Tyr Pro Pro Gly Cys
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 169

Phe Glu Cys Glu Asn Trp Glu Trp Tyr Cys Tyr Pro Pro Gly Cys
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 170

Phe Glu Cys Asp Asn Trp Glu Trp Tyr Cys Tyr Pro Pro Gly Cys
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 171

Phe Glu Cys Glu Gln Trp Glu Trp Tyr Cys Tyr Pro Pro Gly Cys
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 172

Phe Glu Cys Asp Gln Trp Glu Trp Tyr Cys Tyr Pro Pro Gly Cys
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 173

Phe Glu Cys Glu Asn Trp Asp Trp Phe Cys Tyr Pro Pro Gly Cys
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 174
```

```
Phe Glu Cys Asp Asn Trp Asp Trp Phe Cys Tyr Pro Pro Gly Cys
 1               5                  10                  15
```

<210> SEQ ID NO 175
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 175

```
Phe Glu Cys Glu Gln Trp Asp Trp Phe Cys Tyr Pro Pro Gly Cys
 1               5                  10                  15
```

<210> SEQ ID NO 176
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 176

```
Phe Glu Cys Asp Gln Trp Asp Trp Phe Cys Tyr Pro Pro Gly Cys
 1               5                  10                  15
```

<210> SEQ ID NO 177
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 177

```
Phe Glu Cys Glu Asn Trp Glu Trp Phe Cys Tyr Pro Pro Gly Cys
 1               5                  10                  15
```

<210> SEQ ID NO 178
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 178

```
Phe Glu Cys Asp Asn Trp Glu Trp Phe Cys Tyr Pro Pro Gly Cys
 1               5                  10                  15
```

<210> SEQ ID NO 179
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 179

```
Phe Glu Cys Glu Gln Trp Glu Trp Phe Cys Tyr Pro Pro Gly Cys
 1               5                  10                  15
```

<210> SEQ ID NO 180
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 180

Phe Glu Cys Asp Gln Trp Glu Trp Phe Cys Tyr Pro Pro Gly Cys
1               5                   10                  15

<210> SEQ ID NO 181
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 181

Phe Cys Glu Asn Trp Asp Trp Tyr Cys Tyr Pro Pro Gly Cys
1               5                   10

<210> SEQ ID NO 182
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 182

Phe Cys Asp Asn Trp Asp Trp Tyr Cys Tyr Pro Pro Gly Cys
1               5                   10

<210> SEQ ID NO 183
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 183

Phe Cys Glu Gln Trp Asp Trp Tyr Cys Tyr Pro Pro Gly Cys
1               5                   10

<210> SEQ ID NO 184
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 184

Phe Cys Asp Gln Trp Asp Trp Tyr Cys Tyr Pro Pro Gly Cys
1               5                   10

<210> SEQ ID NO 185
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 185

Phe Cys Glu Asn Trp Glu Trp Tyr Cys Tyr Pro Pro Gly Cys
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 186

Phe Cys Asp Asn Trp Glu Trp Tyr Cys Tyr Pro Pro Gly Cys

```
1               5                   10
```

<210> SEQ ID NO 187
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 187

```
Phe Cys Glu Gln Trp Glu Trp Tyr Cys Tyr Pro Pro Gly Cys
1               5                   10
```

<210> SEQ ID NO 188
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 188

```
Phe Cys Asp Gln Trp Glu Trp Tyr Cys Tyr Pro Pro Gly Cys
1               5                   10
```

<210> SEQ ID NO 189
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 189

```
Phe Cys Glu Asn Trp Asp Trp Phe Cys Tyr Pro Pro Gly Cys
1               5                   10
```

<210> SEQ ID NO 190
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 190

```
Phe Cys Asp Asn Trp Asp Trp Phe Cys Tyr Pro Pro Gly Cys
1               5                   10
```

<210> SEQ ID NO 191
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 191

```
Phe Cys Glu Gln Trp Asp Trp Phe Cys Tyr Pro Pro Gly Cys
1               5                   10
```

<210> SEQ ID NO 192
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 192

```
Phe Cys Asp Gln Trp Asp Trp Phe Cys Tyr Pro Pro Gly Cys
1               5                   10
```

```
<210> SEQ ID NO 193
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 193

Phe Cys Glu Asn Trp Glu Trp Phe Cys Tyr Pro Pro Gly Cys
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 194

Phe Cys Asp Asn Trp Glu Trp Phe Cys Tyr Pro Pro Gly Cys
1               5                   10

<210> SEQ ID NO 195
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 195

Phe Cys Glu Gln Trp Glu Trp Phe Cys Tyr Pro Pro Gly Cys
1               5                   10

<210> SEQ ID NO 196
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 196

Phe Cys Asp Gln Trp Glu Trp Phe Cys Tyr Pro Pro Gly Cys
1               5                   10

<210> SEQ ID NO 197
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 197

Cys Tyr Pro Pro Gly Cys
1               5

<210> SEQ ID NO 198
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 198

Cys Tyr Met Asp Val
1               5
```

```
<210> SEQ ID NO 199
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 199

Cys Phe Cys Phe Asp Val
1               5

<210> SEQ ID NO 200
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 200

Phe Cys Gly Asp Gly Phe Tyr Ala Cys Tyr Met Asp Val
1               5                  10
```

COMPOSITIONS AND METHODS OF TREATING TUMORS

CROSS REFERENCE TO RELATED APPLICATIONS

This application claims priority to U.S. Provisional Application No. 60/076,788 filed Mar. 4, 1998, which is incorporated herein by reference. This application is related to U.S. Ser. No. 08/737,269 filed Feb. 11, 1997, now U.S. Pat. No. 5,837,523, which is the U.S. National Stage application of PCT application PCT/US95/05614 filed May 5, 1995, and U.S. Ser. No. 08/239,202 filed May 5, 1994, abandoned, which are each incorporated herein by reference.

ACKNOWLEDGMENT OF GOVERNMENT RIGHTS

This invention was made under grants from the U.S. Government including grant DAMD17-96-6029 from the U.S. Army and grant 5R01 EY09333 from the National Institutes of Health. The U.S. government has rights in the invention.

FIELD OF THE INVENTION

The present invention relates to proteins which lack tyrosine kinase activity and dimerize with members of the erbB family of receptors; to nucleic acid molecules that encode such proteins; to pharmaceutical compositions that comprise such nucleic acid molecules in combination with delivery vehicles which facilitate transfer of the nucleic acid molecule to a cell; and to methods of preventing tumors and treating individuals having tumors by administering such pharmaceutical compositions. The present invention relates to compositions which are useful to convert tumor cells that are resistant to radiation- and/or chemical-induced cell death into cells which are sensitive to radiation. The present invention relates to methods of treating individuals who have tumors by administering such compositions in combination with radiation and/or chemotherapy.

BACKGROUND OF THE INVENTION

The erbB family of receptors includes erbB1 (EGFR), erbB2 (p185), erbB3 and erbB4. Ullrich, et al. (1984) *Nature* 309, 418–425, which is incorporated herein by reference, describes EGFR. Schechter, A. L., et al. (1984) *Nature* 312, 513–516, and Yamamoto, T., et al. (1986) *Nature* 319, 230–234, which are each incorporated herein by reference, describe p185neu/erbB2. Kraus, M. H., et al. (1989) *Proc. Natl. Acad. Sci. USA* 86, 9193–9197 which is incorporated herein by reference, describes erbB3. Plowman, G. D., (1993) *Proc. Natl. Acad. Sci. USA* 90, 1746–1750, which is incorporated herein by reference, describes erbB4.

The rat cellular protooncogene c-neu and its human counterpart c-erbB2 encode 185 kDa transmembrane glycoproteins termed p185. Tyrosine kinase (tk) activity has been linked to expression of the transforming phenotype of oncogenic p185 (Bargmann et al., *Proc. Natl. Acad. Sci. USA*, 1988, 85, 5394; and Stern et al., *Mol. Cell. Biol.*, 1988, 8, 3969, each of which is incorporated herein by reference). Oncogenic neu was initially identified in rat neuroglioblastomas (Schechter et al., *Nature*, 1984, 312, 513, which is incorporated herein by reference) and was found to be activated by a carcinogen-induced point mutation generating a single amino acid substitution, a Val to Glu substitution at position 664, in the transmembrane region of the transforming protein (Bargmann et al., *Cell*, 1986, 45, 649, which is incorporated herein by reference). This alteration results in constitutive activity of its intrinsic kinase and in malignant transformation of cells (Bargmann et al., *EMBO J*, 1988, 7, 2043, which is incorporated herein by reference). The activation of the oncogenic p185 protein tyrosine kinase appears to be related to a shift in the molecular equilibrium from monomeric to dimeric forms (Weiner et al., *Nature*, 1989, 339, 230, which is incorporated herein by reference).

Overexpression of c-neu or c-erbB2 to levels 100-fold higher than normal (i.e.,>$10^6$ receptors/cell) also results in the transformation of NIH3T3 cells (Chazin et al., *Oncogene*, 1992, 7, 1859; DiFiore et al., *Science*, 1987, 237, 178; and DiMarco et al., *Mol. Cell. Biol.*, 1990, 10, 3247, each of which is incorporated herein by reference). However, NIH3T3 cells or NR6 cells which express cellular p185 at the level of $10^5$ receptors/cell are not transformed (Hung et al., *Proc. Natl. Acad. Sci. USA*, 1989, 86, 2545; and Kokai et al., *Cell*, 1989, 58, 287, each of which is incorporated herein by reference), unless co-expressed with epidermal growth factor receptor (EGFR), a homologous tyrosine kinase (Kokai et al., *Cell*, 1989, 58, 287, which is incorporated herein by reference). Thus, cellular p185 and oncogenic p185 may both result in the transformation of cells.

Cellular p185 is highly homologous with EGFR (Schechter et al., *Nature*, 1984, 312, 513; and Yamamoto et al., *Nature*, 1986, 319, 230, each of which is incorporated herein by reference) but nonetheless is distinct. Numerous studies indicate that EGFR and cellular p185 are able to interact (Stern et al., *Mol. Cell. Biol.*, 1988, 8, 3969; King et al., *EMBO J.*, 1988, 7, 1647; Kokai et al., *Proc. Natl. Acad. Sci. USA*, 1988, 85, 53 89; and Dougall et al., *J. Cell. Biochem.*, 1993, 53, 61; each of which is incorporated herein by reference). The intermolecular association of EGFR and cellular p185 appear to up-regulate EGFR function (Wada et al., *Cell*, 1990, 61, 1339, which is incorporated herein by reference). In addition, heterodimers which form active kinase complexes both in vivo and in vitro can be detected (Qian et al., *Proc. Natl. Acad. Sci. USA*, 1992, 89, 1330, which is incorporated herein by reference).

Similarly, p185 interactions with other erbB family members have been reported (Carraway et al., *Cell* 1994, 78, 5–8; Alroy et al., *FEBS Lett.* 1997, 410, 83–86; Riese et al., *Mol. Cell. Biol.* 1995, 15, 5770–5776; Tzahar et al., *EMBO J.* 1997, 16, 4938–4950; Surden et al., *Neuron* 1997, 18, 847–855; Pinkas-Kramarski et al., *Oncogene* 1997, 15, 2803–2815; each of which is incorporated herein by reference). Human p185 forms heterodimers with either erbB3 or erbB4 under physiologic conditions, primarily in cardiac muscle and the nervous system, particularly in development.

Cellular p185 proteins are found in adult secretory epithelial cells of the lung, salivary gland, breast, pancreas, ovary, gastrointestinal tract, and skin (Kokai et al., *Proc. Natl. Acad. Sci. USA*, 1987, 84, 8498; Mori et al., *Lab. Invest.*, 1989, 61, 93; and Press et al., *Oncogene*, 1990, 5, 953; each of which is incorporated herein by reference). Recent studies have found that the amplification of c-erbB2 occurs with high frequency in a number of human adenocarcinomas such as gastric (Akiyama et al., *Science*, 1986, 232, 1644, which is incorporated herein by reference), lung (Kern et al., *Cancer Res.*, 1990, 50, 5184, which is incorporated herein by reference) and pancreatic adenocarcinomas (Williams et al., *Pathobiol.*, 1991, 59, 46, which is incorporated herein by reference). It has also been reported that increased c-erbB2 expression in a subset of breast and ovarian carcinomas is linked to a less optimistic clinical prognosis (Slamon et al., *Science*, 1987, 235, 177; and Slamon et al., *Science*, 1989, 244, 707, each of which is incorporated herein by reference). Heterodimeric association of EGFR and p185 has also been detected in human breast cancer cell lines, such as SK-Br-3 (Goldman et al., *Biochemistry*, 1990, 29, 11024, which is incorporated herein by reference), and transfected cells (Spivak-Kroizman et al., *J Biol. Chem.*, 1992, 267, 8056, which is incorporated herein by reference). Additionally, cases of erbB2 and EGFR coexpression in cancers of the breast and prostate have been reported. In addition, heterodimeric association of p185 and erbB3 as well as heterodimeric association of p185 and erbB4 have also been detected in human cancers. Coexpression of erbB2 and erbB3 has been observed in human breast cancers. Coexpression of EGFR, erbB2, and erbB3 has been seen in prostate carcinoma.

Amplification and/or alteration of the EGFr gene is frequently observed in glial tumor progression (Sugawa, et al. (1990) *Proc. Natl. Acad. Sci.* 87: 8602–8606; Ekstrand, et al. (1992) *Proc. Natl. Acad. Sci.* 89: 4309–4313), particularly in glioblastoma, the most malignant glial tumor (Libermann, et al Supra; Wong, et al. Supra; James, et al. (1988) *Cancer Res.* 48: 5546–5551; Cavenee, W. K. (1992) *Cancer* 70: 1788–93; Nishikawa, et al., (1994) *Proc. Natl. Acad. Sci.* 91: 7727–7731; Schlegel, et al. (1994) *Int J. Cancer* 56: 72–77). A significant proportion of these tumors show EGFr amplification with or without gene alteration (Ekstrand, et al Supra; Libermann, et al. Supra; Wong, et al. (1987) *Proc. Natl. Acad. Sci.* 84:6899–6903), and this has been correlated with a shorter interval to disease recurrence and poorer survival (Schlegel, et al. Supra).

EGFr amplification can be associated with aberrant EGFr transcripts along with normal EGFr transcripts (Sugawa, et al Supra). Frequent amplification and subsequent structural alteration suggests the EGFr may be important for the maintenance of the phenotype of malignant glioma. A frequently observed EGFr mutant has been identified in a subset of human glioblastomas and results from an in-frame truncation of 801 bp (corresponding to exons 2–7) in the extracellular domain of the receptor (Sugawa, et al. Supra; Ekstrand, et al Supra; Malden, et al. (1988) *Cancer Res.* 48: 2711–2714; Humphrey, et al. (1990) *Proc. Natl. Acad. Sci.* 87: 4207–4211; Wong, et al. (1992) *Proc. Natl. Acad. Sci.* 89: 2965–2969), which is thought to result in constitutive kinase activation and may also affect the ligand-binding properties of the molecule (Nishikawa, et al. Supra; Callaghan, et al. (1993) *Oncogene* 8: 2939–2948).

Observed mutations of EGFr in human epithelial malignancies consist of overexpression with or without amplification and, less commonly, of coding sequence alterations. Oncogenic transformation caused by mutants of EGFr appear to be tissue-specific and have been observed in erythroid leukemia, fibrosarcoma, angiosarcoma, melanoma, as well as glioblastoma (Carter, et al. (1994) *Crit Rev Oncogenesis* 5: 389–428). Overexpression of the normal EGFr may cause oncogenic transformation in certain cases, probably in an EGF-dependent manner (Carter, et al. Supra; Haley, et al. (1989) *Oncogene* 4: 273–283). Transfection of high amounts of wild-type EGFr into NIH3T3 cells results in ligand-dependent but incomplete transformation (Yamazaki, et al. (1990) *Jpn. J. Cancer Res.* 81: 773–779). Overexpression may cause altered cell-cycle regulation of the EGFr kinase, and contribute to the transformed state, as has been observed for oncogenic p185neu (Kiyokawa, et al. (1995) *Proc. Natl. Acad. Sci.* 92:1092–1096).

There is a need for therapeutic compositions useful to treat individuals identified as having erbB-mediated tumors. There is a need to develop prophylactic compositions for individuals susceptible to developing erbB-mediated tumors. There is a need for methods of treating individuals identified as having erbB-mediated tumors. There is a need to methods of preventing individuals who are susceptible to developing erbB-mediated tumors from developing such tumors.

SUMMARY OF THE INVENTION

The present invention relates to nucleic acid molecules which comprise a nucleotide sequence that encodes a protein that lacks tyrosine kinase activity and dimerizes with members of the erbB family of receptors, such as erbB1 (EGFR), erbB2 (p185), erbB3 and/or erbB4.

The present invention relates to nucleic acid molecules which comprise a nucleotide sequence that encodes a protein that lacks tyrosine kinase activity and dimerizes with human EGFR and human 185.

The present invention relates to nucleic acid molecules in combination with delivery components in which the nucleic acid molecules comprise a nucleotide sequence that encodes a protein that lacks tyrosine kinase activity and dimerizes with members of the erbB family of receptors, such as erbB1 (EGFR), erbB2 (p185), erbB3 and/or erbB4.

The present invention relates to nucleic acid molecules in combination with delivery components in which the nucleic acid molecules comprise a nucleotide sequence that encodes a protein that lacks tyrosine kinase activity and dimerizes with human EGFR and human p185.

The present invention relates to recombinant viral vectors which comprise nucleic acid molecules that include a nucleotide sequence that encodes a protein that lacks tyrosine kinase activity and dimerizes with members of the erbB family of receptors, such as erbB1 (EGFR), erbB2 (p185), erbB3 and/or erbB4.

The present invention relates to recombinant viral vectors which comprise nucleic acid molecules that include a nucleotide sequence that encodes a protein that lacks tyrosine kinase activity and dimerizes with human EGFR and human p185.

The present invention relates to a pharmaceutical composition comprising a nucleic acid molecule in combination with delivery components. The nucleotide sequence of the nucleic acid molecule encodes a protein that lacks tyrosine kinase activity and dimerizes with members of the erbB family of receptors, such as erbB1 (EGFR), erbB2 (p185), erbB3 and/or erbB4, and preferably a protein that lacks tyrosine kinase activity and dimerizes with human EGFR and human p185.

The present invention relates to a pharmaceutical composition comprising recombinant viral vectors that include nucleic acid molecules with a nucleotide sequence that encodes a protein that lacks tyrosine kinase activity and dimerizes with human EGFR and human p185.

The present invention relates to a method of treating an individual identified as undergoing erbB-mediated cellular transformation. The treatment includes administering to the individual a pharmaceutical composition comprising a nucleic acid molecule in combination with delivery components in an amount sufficient to reverse the cellular transformation. The nucleic acid sequence encodes a protein that lacks tyrosine kinase activity and dimerizes with members of the erbB family of receptors, such as erbB1 (EGFR), erbB2 (p185), erbB3 and/or erbB4. The delivery components may be viral particles and the nucleic acid molecule may be a viral genome.

The present invention relates to a method of treating an individual identified as undergoing p185-mediated cellular transformation. The treatment includes administering to the individual a pharmaceutical composition comprising a nucleic acid molecule in combination with delivery components in an amount sufficient to reverse the cellular transformation. The nucleic acid sequence encodes a protein that lacks tyrosine kinase activity and dimerizes with human EGFR and human p185. The delivery components may be viral particles and the nucleic acid molecule may be a viral genome.

The present invention relates to methods of preventing erbB-mediated cellular transformation in an individual identified as susceptible to erbB-mediated cellular transformation. The methods include administering to the individual a pharmaceutical composition comprising a nucleic acid molecule in combination with delivery components in an amount sufficient to prevent the cellular transformation. The nucleic acid sequence encodes a protein that lacks tyrosine kinase activity and dimerizes with members of the erbB family of receptors, such as erbB1 (EGFR), erbB2 (p185), erbB3 and/or erbB4. The delivery components may be viral particles and the nucleic acid molecule may be a viral genome.

The present invention relates to methods of preventing p185-mediated cellular transformation in an individual identified as being susceptible to p185-mediated cellular transformation. The methods include administering to the individual a pharmaceutical composition comprising a nucleic acid molecule in combination with delivery components in an amount sufficient to prevent the cellular transformation. The nucleic acid sequence encodes a protein that lacks tyrosine kinase activity and dimerizes with human EGFR and human p185. The delivery components may be viral particles and the nucleic acid molecule may be a viral genome.

The present invention relates to methods treating individuals who have erbB protein mediated tumors comprising the steps of administering to such individuals, nucleic acid molecules that encode a protein that dimerizes with said erbB protein and that is deficient in tyrosine kinase activity, and exposing said individual to a therapeutically effective amount of anti-cancer radiation and/or administering to said individual a therapeutically effective amount of an anti-cancer chemotherapeutic.

The present invention relates to methods of treating individuals who have erbB protein mediated tumors comprising the steps of first administering to the individuals a composition which inhibits formation of erbB protein dimers that produce elevated tyrosine kinase activity in a tumor cell, followed by exposing the individuals to a therapeutically effective amount of anti-cancer radiation.

The present invention relates to methods of treating an individual who have tumors that are characterized by tumor cells that have multimeric receptor ensembles which provide kinase activity associated with a transformed phenotype. The methods comprise the steps of administering to the individual, a composition that disrupts the kinase activity associated with the multimeric receptor ensemble; and exposing the individual to a therapeutic amount of gamma radiation.

The present invention relates to methods of treating individuals who have tumors that are characterized by tumor cells that have multimeric receptor ensembles which provide kinase activity associated with a transformed phenotype. The methods comprise the steps of administering to the individual, a active agent which is not an antibody, such as a peptide, non-proteinaceous compound or nucleic acid molecules that encodes a protein that disrupts the kinase activity associated with the multimeric receptor ensemble; and exposing the individual to a therapeutic amount of gamma radiation and/or administering a therapeutic amount of a cytotoxic chemotherapeutic agent to the individual.

The present invention relates to methods of treating individuals who have tumors that are characterized by tumor cells that comprise an EGFR species such as wild type or mutant EGFR, The method comprises the steps of administering to the individual, a composition that disrupts kinase activity mediated by an EGFR species; and exposing the individual to a therapeutic amount of gamma radiation and/or administering a therapeutic amount of a cytotoxic chemotherapeutic agent to said individual.

The present invention relates to methods of treating an individual who has an erbB protein mediated tumor comprising the steps of administering to the individual a nucleic acid molecule that encodes a protein that dimerizes with the erbB protein and that is deficient in tyrosine kinase activity, and exposing the individual to a therapeutically effective amount of anti-cancer radiation and/or administering to the individual a therapeutically effective amount of an anti-cancer chemotherapeutic. In some embodiments, the erbB-protein mediated tumor is a p185-mediated tumor. In some embodiments, the erbB-protein mediated tumor is an EGFR-mediated tumor. In some embodiments, the erbB-protein mediated tumor is a glial tumor. In some embodiments, the erbB-protein mediated tumor is a glioblastoma. In some embodiments, the administration of the nucleic acid molecule is by intratumor administration. In some embodiments, the individual has surgery prior to administration of the nucleic acid molecule. In some embodiments, the protein comprises a p185 ectodomain. In some embodiments, the protein comprises a rat neu transmembrane region with a val to glu mutation at amino acid 664. In some embodiments, the nucleic acid molecule is the viral genome of a recombinant adenovirus. In some embodiments, the nucleic acid molecule comprises a coding sequences operably linked to regulatory elements for translation in cells of the individual, the coding sequence comprises: a truncated rat neu gene with a stop codon at amino acid 691; a truncated rat neu gene with a stop codon at amino acid 691 and val→glu mutation at amino acid 664; a chimeric p185 gene comprising human p185c-erbB2 ectodomain linked to rat neu transmembrane with a stop codon at amino acid 691; a chimeric p185 gene comprising human p185c-erbB2 ectodomain linked to rat neu transmembrane with a stop codon at amino acid 691 and a val→glu mutation at amino acid 664; a chimeric p185 gene comprising human EGFR ectodomain linked to rat neu transmembrane with a stop codon at amino acid 691; a chimeric p185 gene comprising human EGFR ectodomain linked to rat neu transmembrane with a stop codon at amino acid 691 and a val→glu mutation at amino acid 664; a chimeric p185 gene comprising human erbB3 ectodomain linked to rat neu transmembrane with a stop codon at amino acid 691; a chimeric p185 gene comprising human erbB3 ectodomain linked to rat neu transmembrane with a stop codon at amino acid 691 and a val→glu mutation at amino acid 664; a chimeric p185 gene comprising human erbB4 ectodomain linked to rat neu transmembrane with a stop codon at amino acid 691; or a chimeric p185 gene comprising human erbB4 ectodomain linked to rat neu transmembrane with a stop codon at amino acid 691 and a val→glu mutation at amino acid 664. In some embodiments, the individual is exposed to a therapeutically effective amount of anti-cancer radiation. In some embodiments, the individual is administered a therapeutically effective amount of anti-cancer chemotherapeutic.

The present invention relates to methods of treating an individual who has an erbB protein mediated brain tumor comprising the step administering to the individual a nucleic acid molecule that encodes a protein that dimerizes with the erbB protein and is deficient in tyrosine kinase activity. In some embodiments, the protein comprises a p185 ectodomain. In some embodiments, the nucleic acid molecule contains a rat neu transmembrane region with a val to glu mutation at amino acid 664. In some embodiments, the erbB-protein mediated tumor is an EGFR-mediated tumor. In some embodiments, the erbB-protein mediated tumor is a mutant EGFR-mediated tumor. In some embodiments, the erbB-protein mediated tumor is a glioblastoma. In some embodiments, the individual is exposed to a therapeutically effective amount of anti-cancer radiation and/or administered a therapeutically effective amount of an anti-cancer chemotherapeutic. In some embodiments, the administration of the nucleic acid molecule is by direct injection into the tumor. In some embodiments, the administration of the nucleic acid molecule is by direct injection into the tumor using stereotaxic surgical procedures. In some embodiments, the individual has surgery to remove bulk tumor prior to administration of the nucleic acid molecule. In some embodiments, the nucleic acid molecule is the viral genome of a recombinant adenovirus. In some embodiments, the nucleic acid molecule comprises a coding sequences operably linked to regulatory elements for translation in cells of the individual, and the coding sequence comprises: a truncated rat neu gene with a stop codon at amino acid 691 (N691stop construct); a truncated rat neu gene with a stop codon at amino acid 691 and a val→glu mutation at amino acid 664; a chimeric p185 gene comprising human p185c-erbB2 ectodomain linked to rat neu transmembrane with a stop codon at amino acid 691; a chimeric p185 gene comprising human p185c-erbB2 ectodomain linked to rat neu transmembrane with a stop codon at amino acid 691 and a val→glu mutation at amino acid 664; a chimeric p185 gene comprising human EGFR ectodomain linked to rat neu transmembrane with a stop codon at amino acid 691; a chimeric p185 gene comprising human EGFR ectodomain linked to rat neu transmembrane with a stop codon at amino acid 691 and a val→glu mutation at amino acid 664; a chimeric p185 gene comprising human erbB3 ectodomain linked to rat neu transmembrane with a stop codon at amino acid 691; a chimeric p185 gene comprising human erbB3 ectodomain linked to rat neu transmembrane with a stop codon at amino acid 691 and a val→glu mutation at amino acid 664; a chimeric p185 gene comprising human erbB4 ectodomain linked to rat neu transmembrane with a stop codon at amino acid 691; or a chimeric p185 gene comprising human erbB4 ectodomain linked to rat neu transmembrane with a stop codon at amino acid 691 and a val→glu mutation at amino acid 664.

The present invention relates to methods of inhibiting proliferation of a mutant EGFR-mediated tumor cell comprising the step of delivering to the cell a nucleic acid molecule that encodes a protein that dimerizes with mutant EGFR and is deficient in tyrosine kinase activity. In some embodiments, the protein comprises a p185 ectodomain. In some embodiments, the protein contains a rat neu transmembrane region with a val to glu mutation at amino acid 664. In some embodiments, the mutant EGFR-mediated tumor cell is a glioblastoma cell.

The present invention relates to methods of treating an individual who has an erbB protein mediated tumor comprising the steps of administering to the individual a composition which inhibits formation of erbB protein dimers that produce elevated tyrosine kinase activity in a tumor cell, and exposing the individual to a therapeutically effective amount of anti-cancer radiation. In some embodiments, the erbB-protein mediated tumor is a p185-mediated tumor. In some embodiments, the erbB-protein mediated tumor is an EGFR-mediated tumor. In some embodiments, the erbB-protein mediated tumor is a glial tumor. In some embodiments, the erbB-protein mediated tumor is a glioblastoma. In some embodiments, the administration of the composition is by intratumor administration. In some embodiments, the individual has surgery prior to administration of the composition. In some embodiments, the composition that is administered to a patient comprises a compound that interacts with an erbB protein in a tumor cell to alter the erbB protein sufficient to result in a decreased propensity of it to dimerize with another erbB protein. In some embodiments, the compound that interacts with an erbB protein in a tumor cell to alter the erbB protein sufficient to result in a decreased propensity of it to dimerize with another erbB protein is an antibody. In some embodiments, the antibody is a monoclonal antibody. In some embodiments, the composition that is administered to a patient comprises a compound that competitively interacts with an erbB protein in a tumor cell to competitively inhibit dimer formation with another erbB protein and prevents elevated tyrosine kinase activity. In some embodiments the compound that competitively interacts with an erbB protein in a tumor cell to competitively inhibit dimer formation with another erbB protein is a peptide. In some embodiments, the compound that competitively interacts with an erbB protein in a tumor cell to competitively inhibit dimer formation with another erbB protein is an antibody. In some embodiments, the composition that is administered to the tumor cell is a nucleic acid molecule that encodes a protein that competitively interacts with an erbB protein in a tumor cell to competitively inhibit dimer formation with another erbB protein. In some embodiments, the protein is a mutant or truncated kinase deficient erbB protein. In some embodiments, the protein is a mutant or truncated kinase deficient p185 protein. In some embodiments, the protein interacts with the transmembrane region of the one erbB protein. In some embodiments, the protein comprises a rat neu transmembrane region with a val to glu mutation at amino acid 664. In some embodiments, the protein interacts with the ectodomain region of the one erbB protein. In some embodiments, the protein comprises a p185 ectodomain. In some embodiments, the nucleic acid molecule is administered by intratumor administration. In some embodiments, the individual has surgery prior to administration of the nucleic acid molecule. In some embodiments, the nucleic acid molecule is the viral genome of a recombinant adenovirus. In some embodiments, the nucleic acid molecule comprises a coding sequences operably linked to regulatory elements for translation in cells of the individual, and the coding sequence comprises: a truncated rat neu gene with a stop codon at amino acid 691; a truncated rat neu gene with a stop codon at amino acid 691 and a val→glu mutation at amino acid 664; a chimeric p185 gene comprising human p185c-erbB2 ectodomain linked to rat neu transmembrane with a stop codon at amino acid 691; a chimeric p185 gene comprising human p185c-erbB2 ectodomain linked to rat neu transmembrane with a stop codon at amino acid 691 and a val→glu mutation at amino acid 664; a chimeric p185 gene comprising human EGFR ectodomain linked to rat neu transmembrane with a stop codon at amino acid 691; a chimeric p185 gene comprising human EGFR ectodomain linked to rat neu transmembrane with a stop codon at amino acid 691 and a val→glu mutation at amino acid 664; a chimeric p185 gene comprising human erbB3 ectodomain linked to rat neu transmembrane with a stop codon at amino acid 691; a chimeric p185 gene comprising human erbB3 ectodomain linked to rat neu transmembrane with a stop codon at amino acid 691 and a val→glu mutation at amino acid 664; a chimeric p185 gene comprising human erbB4 ectodomain linked to rat neu transmembrane with a stop codon at amino acid 691; or a chimeric p185 gene comprising human erbB4 ectodomain linked to rat neu transmembrane with a stop codon at amino acid 691 and a val→glu mutation at amino acid 664.

The present invention relates to methods of treating an individual who has a tumor, wherein the tumor is characterized by tumor cells that have multimeric receptor ensembles which provide kinase activity associated with a transformed phenotype. The method comprises the steps of administering to the individual, a composition that disrupts the kinase activity associated with the multimeric receptor ensemble; and exposing the individual to a therapeutic amount of gamma radiation. In some embodiments, the tumor is characterized by tumor cells that have multimeric receptor ensembles selected from the group consisting of: erbB homodimers, erbB heterodimers, and multimers of platelet derived growth factor receptors. In some embodiments, the tumor is characterized by tumor cells that have erbB homodimers that are mutant EGFR homodimers or p185 homodimers. In some embodiments, the tumor is characterized by tumor cells that have erbB heterodimers that are p185/EGFR heterodimers, p185/mutant EGFR heterodimers, p185/erbB3 heterodimers; p185/erbB4 heterodimers or EGFR/mutant EGFR heterodimers. In some embodiments, the composition that disrupts the kinase activity associated with the multimeric receptor ensemble comprises an active agent selected from the group consisting of antibodies, peptides, and non-proteinaceous kinase inhibitors. In some embodiments, the composition that disrupts the kinase activity associated with the multimeric receptor ensemble comprises an active agent that is a nucleic acid molecule that encodes a protein or peptide which interacts with a monomeric component of the ensemble to prevent the monomeric component from interacting with a second monomeric component of the ensemble.

The present invention relates to methods of treating an individual who has a tumor, wherein the tumor is characterized by tumor cells that have multimeric receptor ensembles which provide kinase activity associated with a transformed phenotype. The method comprises the steps of administering to the individual, a small peptide, non-proteinaceous compound or nucleic acid molecules that encodes a non-antibody protein or peptide that disrupts the kinase activity associated with the multimeric receptor ensemble; and exposing the individual to a therapeutic amount of gamma radiation and/or administering a therapeutic amount of a cytotoxic chemotherapeutic agent to the individual. In some embodiments, the tumor is characterized by tumor cells that have multimeric receptor ensembles selected from the group consisting of: erbB homodimers, erbB heterodimers, and multimers of platelet derived growth factor receptors. In some embodiments, the tumor is characterized by tumor cells that have erbB homodimers that are mutant EGFR homodimers or p185 homodimers. In some embodiments, the tumor is characterized by tumor cells that have erbB heterodimers that are p185/EGFR heterodimers, p185/mutant EGFR heterodimers, p185/erbB3 heterodimers; p185/erbB4 heterodimers or EGFR/mutant EGFR heterodimers. In some embodiments, the composition that disrupts the kinase activity associated with the multimeric receptor ensemble comprises an active agent selected from the group consisting of peptides, and non-proteinaceous kinase inhibitors. In some embodiments, the composition that disrupts the kinase activity associated with the multimeric receptor ensemble comprises an active agent that is a nucleic acid molecule that encodes a protein or peptide which interacts with a monomeric component of the ensemble to prevent the monomeric component from interacting with a second monomeric component of the ensemble.

The present invention relates to methods of treating an individual who has a tumor, wherein the tumor is characterized by tumor cells that comprise an EGFR species. The methods comprise the steps of administering to the individual, a composition that disrupts kinase activity mediated by an EGFR species; and exposing the individual to a therapeutic amount of gamma radiation and/or administering a therapeutic amount of a cytotoxic chemotherapeutic agent to the individual. In some embodiments, the EGFR species is a mutant EGFR. In some embodiments, the composition that disrupts kinase activity mediated by an EGFR species comprises an active agent selected from the group consisting of antibodies, peptides, and non-proteinaceous kinase inhibitors. In some embodiments, the composition that disrupts kinase activity mediated by an EGFR species comprises an active agent that is a nucleic acid molecule that encodes a protein or peptide which interacts with a molecule of an EGFR species to prevent the molecule or from forming a kinase-activity elevating multimeric ensemble with a second molecule. In some embodiments, the individual is administered a cytotoxic chemotherapeutic agent.

BRIEF DESCRIPTION OF THE FIGURES

FIGS. 2A and 2B shows data relating to the determination of apoptosis and clonogenic survival following gamma-irradiation of human glioblastoma cells. In FIG. 2A, cells were plated and allowed to attach before being exposed to gamma-irradiation (10Gy) in 10% serum or serum-free media. After 72 h, quantitation of apoptosis was conducted by two independent observers. The apoptotic index is the percentage of apoptotic cells with morphologic evidence of apoptosis as determined by staining of nuclei with DAPI. Results presented are mean±S.E.M of four independent experiments and the mean is indicated in parentheses. U87MG cells were grown in 10% serum or serum-free media and U87/T691 cells were grown in 10% serum or serum-free media. In FIG. 2B, U87MG and U373MG human glioma cells and derivatives were stained with DAPI and analyzed for apoptotic morphology 72 h after gamma-irradiation. The mean is indicated in parentheses and the index shown in this representative experiment is mean±S.D. These results were confirmed in two additional experiments. Apoptotic indices were felt to be an underestimate since floating cells could not be assayed by this technique.

FIG. 3 shows clonogenic survival after irradiation. Cells were plated and gamma-irradiated with varying doses of radiation followed by incubation for 7–10 days at 37° C. with 5% $CO_2$. Colonies were then stained and those with more than 50 cells were counted under a dissecting microscope. The log survival was then determined by calculating the ratio of the number of colonies formed to the number of cells plated, after correcting for plating efficiency. Similar experiments were performed three times.

DESCRIPTION OF THE PREFERRED EMBODIMENTS

Figure 1A:
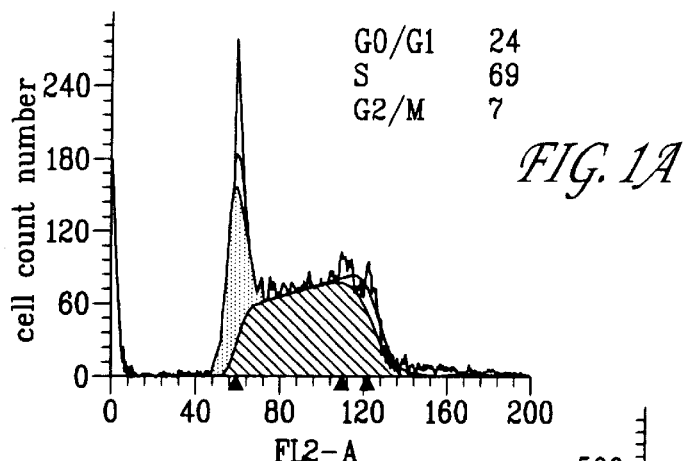
FIGS. 1A, 1B, 1C and 1D show data regarding cell cycle distribution of human glioblastoma cells with or without radiation treatment. Cells were plated in 60 mm dishes and allowed to attach before either being gamma-irradiated (10Gy) (FIGS. 1B and 1D) or mock-irradiated (FIG. 1A and 1C). After 72 h, cells were than analyzed by flow cytometry after PI staining. The distributions of cells according to DNA content are indicated in each panel. Representative experiments were performed four independent times.

As used herein, the terms "erbB-associated cancer" and "erbB-associated tumors" are meant to refer to tumor cells and neoplasms which express a member of the erbB gene family, the expression of which results in erbB-mediated transformation. Neu-associated tumors and EGFR-associated tumors are examples of erbB-associated tumors.

As used herein, the terms "neu-associated cancer" "neu-associated tumors" and "p185-associated tumors" are meant to refer to tumor cells and neoplasms which express the neu gene to produce p185. Neu-associated cancer is a an erbB-associated cancer in which the cellular transformation is mediated by tyrosine kinase activity related to p185.

As used herein, the terms "EGFR-associated cancer" and "EGFR-associated tumors" are meant to refer to tumor cells and neoplasms which express EGFR. EGFR-associated cancer is an erbB-associated cancer in which the cellular transformation is mediated by tyrosine kinase activity related to EGFR.

As used herein, the terms "mutant EGFR-associated cancer" and "mutant EGFR-associated tumors" are meant to refer to tumor cells and neoplasms which express mutant forms of EGFR. Mutant EGFR-associated cancer is an EGFR-associated cancer in which the cellular transformation is mediated by tyrosine kinase activity related to mutant EGFR. Alterations of receptor subunits as a result of structural changes may be coupled to receptor oligomerization resulting in amplification of signaling. A mutant EGFR may be a constitutively activated extracellular-deleted mutant EGFR form (ΔEGFR) commonly observed in human glial tumors. A ΔEGFR oncoprotein commonly observed in human glial neoplasms and other human epithelial malignancies (ΔEGFR or EGFRvIII) results from an in-frame truncation involving exons 2 through 7 (amino acids 6 to 273) in the gene encoding the extracellular region of the molecule resulting in the expression of truncated, constitutively phosphorylated ΔEGFRs of 140–155 kDa. ΔEGF receptors have been observed to exist spontaneously in a dimeric form and mediate constitutive signaling and oncogenic transformation of rodent fibroblasts in a ligand-independent manner, while overexpressed p170 holo-EGFRs are only weakly transforming in the presence of EGF. ΔEGFR oncoproteins confer a dramatic growth advantage in vivo in human glioblastoma cells and in murine fibroblasts. Recent reports indicate that ΔEGF receptors are present on the cell surface and internalize more slowly than ligand-stimulated holo-EGFRs, which may increase transforming efficiency of ΔEGFR oncoproteins. Other mutations which functionally separate the extracellular domain from the transmembrane and cytoplasmic region of RTK polypeptides have also been observed to lead to spontaneous dimerization and to the acquisition of transforming potential, suggesting that a portion of the extracellular domain imposes a structural constraint on dimer formation which is presumably removed by ligand-binding or mass action. Extracellular deletions observed in ΔEGFRs or avian v-erbB oncogenes presumably facilitate dimer formation by mimicking the conformational changes resulting from ligand-binding. Soluble extracellular domains of the EGFR have been observed to oligomerize and structural alteration in the ectodomain can induce spontaneous oligomerization of extracellular domains, cytoplasmic domains, or both. The extracellular deletion in EGFR removes the majority of amino acids comprising subdomains I and II of the EGFR, which includes a large portion of the first (more amino-terminal) of two cysteine-rich sequences in the extracellular region of the receptor. Subdomain III, which has been reported to confer ligand-binding properties to the EGFR, is preserved in the EGFR oncoprotein, although EGFRs do not appear to bind ligand in NIH3T3 cells. Coexpression of holo-EGFRs and ΔEGFRs has been observed in human glioblastoma and other tumor samples, suggesting that ΔEGFR/EGFR co-expressing cells may be a close correlate of human disease.

As used herein, the term "EGFR species" is meant to refer to wild-type and mutant forms of EGFR.

As used herein, the term "erbB-mediated cellular transformation" is meant to refer to the cellular transformation which erbB-associated tumor cells and neoplasms undergo. Cells undergo erbB-mediated transformation in connection with elevated levels of tyrosine kinase activity by members of the erbB family of receptors. The transformed phenotype of erbB-mediated transformed cells can be arrested and/or reversed by expression of tyrosine kinase deficient proteins that dimerize with members of the erbB family of receptors.

As used herein, the term "p185-mediated cellular transformation" is meant to refer to the cellular transformation that p185-associated tumor cells and neoplasms undergo and whose transformed phenotype can be arrested and/or reversed by expression of tyrosine kinase deficient proteins that dimerize with p185. P185-mediated cellular transformation is an erb-mediated cellular transformation.

As used herein, the term "EGFR-mediated cellular transformation" is meant to refer to the cellular transformation that EGFR-associated tumor cells and neoplasms undergo and whose transformed phenotype can be arrested and/or reversed by expression of tyrosine kinase deficient proteins that dimerize with EGFR. EGFR-mediated cellular transformation is an erb-mediated cellular transformation.

As used herein, the term "mutant EGFR-mediated cellular transformation" is meant to refer to the cellular transformation that mutant EGFR-associated tumor cells and neoplasms undergo and whose transformed phenotype can be arrested and/or reversed by expression of tyrosine kinase deficient proteins that dimerize with mutant EGFR. Mutant EGFR-mediated cellular transformation is an erb-mediated cellular transformation.

As used herein, the term "delivery components" is meant to refer to vehicles by which nucleic acid molecules may be delivered to cells of an individual. Delivery components is meant to include viral particles such as viral particles of gene therapy vectors as well as other vehicles, carriers, complexes, entities and structures which are useful to deliver a nucleic acid molecule to a cell.

As used herein, the term "high risk individual" is meant to refer to an individual who has had an erbB-associated tumor, such as for example a neu-associated tumor, either removed or enter remission and who is therefore susceptible to a relapse or recurrence. As part of a treatment regimen for a high risk individual, the individual can be prophylactically treated against tumors that they have been diagnosed as having had in order to combat a recurrence. Thus, once it is known that an individual has had erbB-associated cancer, the individual can be treated according to the present invention to prevent normal cells from transforming into tumor cells.

The present invention is useful to therapeutically treat an individual identified as suffering from erbB-associated tumors, such as neu-associated tumors, in order to reverse the transformed phenotype of the tumor cells. The present invention is useful to prophylactically treat an individual who is predisposed to develop erbB-associated tumors or who has had erbB-associated tumors and is therefore susceptible to a relapse or recurrence.

The translation product of the neu oncogene is p185, a transmembrane glycoprotein having tyrosine kinase activity and a molecular weight of about 185,000 daltons as determined by carrying out electrophoresis on the glycoprotein and comparing its movement with marker proteins of known molecular weight. Experiments have shown that p185 forms dimers with other p185 molecules or with epidermal growth factor receptor (EGFR) and that these dimers exhibit elevated tyrosine kinase activity which brings about the transformed phenotype in cells having such dimers.

P185neu mutants interfere with activated p185neu homodimers (Qian, O'Rourke, Zhao, Greene: Oncogene 13: 2149–2157, 1996). P185neu mutants also interfere with normal EGFR homodimers, mutant EGFR as well as activated EGFR homodimers in fibroblasts and in primary human cancer cells. Administration of nucleic acid molecules which encode proteins capable of forming dimers with other p185 molecules or with EGFR but which dimers do not exhibit elevated tyrosine kinase activity eliminate the transformed phenotype of neu-associated tumors in a population suffering from p185 mediated tumors. Further, administration of such nucleic acid molecules inhibit the neoplastic development in animals susceptible to developing neu transformed tumors.

As discussed above, p185-erbB2 interactions with other erbB family members includes have been reported (Carraway et al., supra; Alroy et al., supra; Riese et al., supra; Tzahar et al., supra; and Surden et al., supra; Pinkas-Kramarski et al., supra). Accordingly, kinase-deficient mutants of p185neu/erbB2 (human homologue) that retain the ability to form heterodimers with EGFR, erbB3, and erbB4 may be used to form dimers with erbB3 and erbB4, as well as EGFR, and modulate signaling in human tumor cells. Thus, the present invention additionally relates to administration of nucleic acid molecules which encode proteins capable of forming dimers with erbB3, and erbB4 but which dimers do not exhibit elevated tyrosine kinase activity eliminate the transformed phenotype of tumors in a population suffering from such tumors. Further, administration of such nucleic acid molecules inhibit the neoplastic development in animals susceptible to developing tumors.

In addition to p185 mutants to interfere with erbB-mediated cellular transformation, other mutant erbB members may be useful to dimerize with wild type erbB proteins and inhibit elevated tyrosine kinase activity associated with wild-type homodimers and heterodimers.

The present invention provides nucleic acid molecules that have a nucleotide sequence which encodes a protein that lacks tyrosine kinase activity and dimerizes with a member of the erbB family of receptors. The protein dimerizes with an erbB protein selected from the group consisting of EGFR, p185, erbB3 and erbB4, preferably at least two members of the erbB family selected from the group consisting of EGFR, p185, erbB3 and erbB4, more preferably at least three members of the erbB family selected from the group consisting of EGFR, p185, erbB3 and erbB4 and more preferably the protein dimerizes with each of EGFR, p185, erbB3 and erbB4. It is preferred that the protein be a mutated or truncated form of a protein that is a member of the erbB family or a chimeric protein that includes sequences from members of the erbB family derived form different species. In some preferred embodiments, the invention provides nucleic acid molecules that have a nucleotide sequence which encodes a protein that lacks tyrosine kinase activity and dimerizes with human EGFR or human p185. The nucleic acid molecules are provided in combination with delivery components such that upon administration of the combination, the nucleic acid molecule is delivered to cells of the individual. When provided as a pharmaceutical composition, the combination is useful for the treatment of individuals suffering from erbB-mediated cellular transformations such as p185-mediated cellular transformation and EGFR-mediated cellular transformation. Such a pharmaceutical composition may also be useful for the prevention of erbB-mediated cellular transformation, particularly in individuals susceptible to such transformation. The nucleic acid molecules of the invention may also be useful to produce specific erbB protein species in competent cells which may be subsequently isolated and used in various immunoassay to detect the presence of antibodies specific for such erbB proteins present in various bodily fluids.

Cellular rat p185 devoid of kinase activity due to either a single amino acid substitution in the consensus sequence for ATP binding, N757, or due to a cytoplasmic domain deletion, N691stop, was able to undergo EGF-induced heterodimerization with EGFR in living cells. EGF was also able to stimulate the trans-phosphorylation of N757 via EGFR. However, heterodimers composed of EGFR and certain truncated p185 proteins were kinase inactive. (See: Qian et al., Proc. Natl. Acad. Sci. USA, 1994, 91, 1500, which is incorporated herein by reference). Similar results were observed using a further modified construct in which the transmembrane region of the truncated p185 protein contained a single change in amino acid sequence, T691stop. Structural alterations in receptors have been shown to act as dominant negative mutations that can suppress the function of wild type (wt) receptors, such as insulin receptor (Chou et al., J. Biol. Chem., 1987, 262, 1842, which is incorporated herein by reference) or EGFR (Honegger et al., J. Cell Biol., 1990, 110, 1541; and Kashles et al., Mol. Cell. Biol., 1991, 11, 1454, each of which is incorporated herein by reference).

The present invention provides a receptor-based strategy of growth inhibition which targets activated oncoprotein receptors of the erbB tyrosine kinase family. Many systemic epithelial cancers express oncogenic forms of erbB receptors, which may confer tumorigenic potential either by overexpression, mutation, or coexpression with other erbB family members. Since the enzymatic kinase function of erbB receptors is activated upon dimerization or oligomerization, the present invention inhibits catalytic activity of surface-based receptors throughout the formation of kinase-defective receptor complexes, thereby reducing the tumorigenic effects of the erbB translation product.

The present invention relates to nucleic acid molecules which comprise a nucleotide sequence that encodes a protein that lacks tyrosine kinase activity and dimerizes with members of the erbB family of receptors, such as erbB1 (EGFR), erbB2 (p185), erbB3 and/or erbB4. The nucleic acid sequence may be either DNA or RNA. The nucleic acid sequence may encode any protein that dimerizes with an erbB protein and which lacks tyrosine kinase activity. The nucleic acid sequence preferably encodes rat or human erb protein which may dimerize with erbB proteins and which also lacks tyrosine kinase activity. According to one aspect of the invention, the nucleic acid molecule comprises a nucleic acid sequence that encodes a protein that lacks tyrosine kinase activity and dimerizes with human EGFR or human p185. The nucleic acid sequence may be either DNA or RNA. The nucleic acid sequence may encode any protein that dimerizes with human EGFR and/or p185 and which lacks tyrosine kinase activity. The nucleic acid sequence preferably encodes rat or human p185 species which may dimerize with human p185 or human EGFR and which also lacks tyrosine kinase activity.

Administration of nucleic acid molecules which encode proteins capable of forming dimers with erbB translation products but which dimers do not exhibit elevated tyrosine kinase activity eliminate the transformed phenotype of erbB-associated tumors in a population suffering from erbB-mediated tumors. Further, administration of such nucleic acid molecules inhibit the neoplastic development in animals susceptible to developing erbB- associated tumors. For example, experiments have shown that p185 forms dimers with erbB translation products such as other p185 molecules or with epidermal growth factor receptor (EGFR) and that these dimers exhibit elevated tyrosine kinase activity which brings about the transformed phenotype in cells having such dimers. Administration of nucleic acid molecules which encode proteins capable of forming dimers with erbB translation products such as other p185 molecules or with EGFR but which dimers do not exhibit elevated tyrosine kinase activity eliminate the transformed phenotype of neu-associated tumors in a population suffering from p185 mediated tumors. Further, administration of such nucleic acid molecules inhibit the neoplastic development in animals susceptible to developing neu transformed tumors.

The occurrence of mammalian tumors cells which express a translation product of a member of the erbB gene family on their surfaces and thereby have undergone erbB-mediated cellular transformation can be reversed or prevented by administration of nucleic acid molecules which comprise sequences that encode proteins which form dimers with translation products of erbB genes but which do not have tyrosine kinase activity. In accordance with the invention, such nucleic acid molecules are provided in combination with delivery components, i.e. delivery vehicles, in order to facilitate incorporation of such nucleic acid molecules into the cells of an animal. An effective amount of such combinations are administered to an individual who is identified as suffering from or being susceptible to susceptible to erbB-associated tumors.

The present invention provides nucleic acid molecules that have a nucleotide sequence which encodes a protein that lacks tyrosine kinase activity and dimerizes with the translation product of a member of the erbB gene family. The nucleic acid molecules are provided in combination with delivery components such that upon administration of the combination, the nucleic acid molecule is delivered to cells of the individual. When provided as a pharmaceutical composition, the combination is useful for the treatment of individuals suffering from erbB-mediated cellular transformations. Such a pharmaceutical composition may also be useful for the prevention of erbB-mediated cellular transformation, particularly in individuals susceptible to such transformation. The nucleic acid molecules of the invention may also be useful to produce specific translation products of a member of the erbB gene family in competent cells which may be subsequently isolated and used in various immunoassay to detect the presence of antibodies specific for the translation product present in various bodily fluids.

The nucleic acid molecules of the invention are used in combination with a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, lipofectin-mediated transfection, transferrin-mediated transfection and other receptor-mediated means. The invention is intended to include such other forms of expression vectors and other suitable delivery means which serve equivalent functions and which become known in the art subsequently hereto.

In a preferred embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions. Examples of recombinant adenoviral vectors include those which have the E1a region deleted and which carry a temperature-sensitive mutation in E2a (Engelhardt et al., Hum Gene Ther 5:1217–1229, 1994, which is incorporated herein by reference). Other examples of recombinant adenoviral vectors useful to deliver nucleic acid sequence of the present invention are described in U.S. Pat. Nos. 5,756,283 and 5,707,618, which are each incorporated herein by reference.

In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another preferred embodiment of the present invention, nucleic acid is delivered through folate receptor means. The nucleic acid sequence to be delivered to a host cell is linked to polylysine and the complex is delivered to the tumor cell by means of the folate receptor. U.S. Pat. No. 5,108,921 issued Apr. 28, 1992 to Low et al., which is incorporated herein by reference, describes such delivery components.

In another preferred embodiment of the present invention, nucleic acid is delivered through the use of lipofectin-mediated DNA transfer. LipofectAMINE™ liposome reagent (Life Technologies, Gaithersburg Md.) is a commercially available liposome encapsulation reagent which can be used for encapsulating cells following manufacturer's instructions. LipofectAMINE™ liposome reagent encapsulated nucleic acid molecules may be delivered to a host cell using liposome formulation administration methods.

In another preferred embodiment of the present invention, nucleic acid is delivered through the use of cationic lipid-mediated DNA transfer such as that which is described in U.S. Pat. No. 5,703,055, which is incorporated herein by reference.

In another preferred embodiment of the present invention, nucleic acid is delivered through the use of liposome-mediated DNA transfer such as that which is described in U.S. Pat. Nos. 4,235,871, 4,241,046 and 4,394,448, which are each incorporated herein by reference.

Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention.

Pharmaceutical compositions may be formulated by one having ordinary skill in the art with compositions selected depending upon the chosen mode of administration. Suitable pharmaceutical carriers are described in *Remington's Pharmaceutical Sciences*, A. Osol, a standard reference text in this field, which is incorporated herein by reference.

The pharmaceutical compositions of the present invention may be administered by any means that enables the active agent to reach the agent's site of action in the body of a mammal. Pharmaceutical compositions may be administered parenterally, i.e., intratumor, intravenous, subcutaneous, intramuscular. Intravenous and intratumor administration are preferred routes.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

In some embodiments, the invention relates to methods of treating patients suffering from human adenocarcinomas which are erbB-associated cancers such as gastric, lung and pancreatic adenocarcinomas and human breast and ovarian carcinomas as well as human breast and prostate cancer which are erbB-associated cancer. In some embodiments, the invention relates to methods of preventing these erbB-associated cancers in high risk individuals. In some embodiments, the invention relates to methods of treating patients suffering from glial tumor progression, particularly in glioblastoma, the most malignant glial tumor. In some embodiments, the invention relates to methods of preventing these erbB-associated cancers in high risk individuals.

In some embodiments, the invention relates to methods of treating patients suffering from human epithelial malignancies erythroid leukemia, fibrosarcoma, angiosarcoma and melanoma. In some embodiments, the invention relates to methods of preventing these erbB-associated cancers in high risk individuals.

According to some embodiments of the invention, the pharmaceutical compositions are administered locally at the site of the tumor. In some embodiments, the pharmaceutical compositions are administered directly into the tumor cells and the tissue immediately surrounding the tumor. In some embodiment, the pharmaceutical compositions are delivered into brain tumors such as, for example, glioblastomas. In some embodiment, the pharmaceutical compositions are delivered into brain tumors as part of the surgical resection of the tumor. In some embodiment, the pharmaceutical compositions are delivered into brain tumors using stereotaxic surgical techniques.

According to some embodiments of the invention, the patient is treated with radiation or other chemotherapy in conjunction the administration of pharmaceutical compositions according to the invention. Chemotherapy approaches include administration of cytotoxic and or cytostatic agents. It has been observed that expression of nucleotide molecules according to the invention in erbB-associated tumors renders the tumors radiosensitized. That is, the tumors are more vulnerable to destruction by radiation during radiotherapy when the patient is treated with pharmaceutical compositions according to the invention. The use of multiple therapeutic approaches provides the patient with a broader based intervention. In some preferred embodiments, treatment with pharmaceutical compositions according to the invention is preceded by surgical intervention. In preferred embodiments, the radiotherapy follows administration of pharmaceutical compositions according to the invention. In preferred embodiments, the radiation therapy using gamma radiation is provided following administration of compositions which convert radiation resistant tumors, radiation sensitive. Those skilled in the art can readily formulate an appropriate radiotherapeutic regimen. Carlos A Perez & Luther W Brady: Principles and Practice of Radiation Oncology, 2nd Ed. JB Lippincott Co, Phila., 1992, which is incorporated herein by reference describes radiation therapy protocols and parameters which can be used in the present invention. For GBMs (glioblastoma, the most malignant glial brain tumor), Simpson W. J. et al. : Influence of location and extent of surgical resection on survival of patients with glioblastoma multiforms: Results of three consecutive Radiation Therapy Oncology Group (RTOG) clinical trials. *Int J Radiat Oncol Biol Phys* 26:239–244, 1993, which is incorporated herein by reference describes clinical protocols useful in the methods of the present invention. Similarly, for Borgelt et al., *The palliation of brain metastases: Final results of the first two studies of the Radiation Therapy Oncology Group. Int J Radiat Oncol Biol Phys* 6:1–9, 1980, which is incorporated herein by reference, describes clinical protocols useful in the methods of the present invention.

According to some embodiments, variants of the p185neu/erbB-2 receptor are used since this receptor has been shown to be the preferred partner for heterodimer assembly for all erbB family kinases, including erbB1/Epidermal Growth Factor Receptor (EGFR), erbB3, and erbB4. According to a preferred embodiment of the invention, a preferred form of kinase-deficient p185neu for use in treating erbB-expressing human tumors is delivered by recombinant adenovirus particles as gene therapy to treat residual, local disease, rather than advanced, bulk disease. The application of surgical techniques will be employed for both local administration and for the reduction in bulk disease characteristic of solid tumors. Multiple human cancers expressing combinations of erbB receptors may be the targets for this receptor-based strategy of growth inhibition.

Inhibition mediated by the introduction of mutant p185neu receptors causes synergistic growth inhibition when combined with conventional cytotoxic agents such as gamma-irradiation. The present invention provides methods of treating many epithelial solid tumors since the methods of the invention complement the use of already established treatment modalities.

The kinase-deficient T691stop form of p185neu is more effective in achieving inhibition of cell growth and transformation than the N691stop form of p185neu in human brain tumor cells expressing elevated levels of the EGFR. T691stop neu also inhibits the constitutive signaling from a mutant EGFR expressed specifically in many epithelial tumors, including malignant human gliomas, and has been shown to reduce the kinase activity of oncogenic, full-length p185neu in primary mammalian cancer cells. T691stop neu contains the rat neu transmembrane point mutation which changes the amino acid at position 664 from valine to glutamine, resulting in a change in the tendency of this receptor to form dimeric and oligomeric complexes.

T691stop neu mutant cDNA has been subcloned into recombinant adenoviral constructs. One vector backbone has the E1a region deleted and carries a temperature-sensitive mutation in E2a (Engelhardt et al., Hum. Gene Ther. 5:1217–1229, 1994, incorporated herein by reference). The recombinant derivation was accomplished in two stages. First, we subcloned T691stop neu into an expression plasmid (pAd.CMV.link as per Example 6) containing adenoviral sequences necessary for viral recombinant production, generating pAd.CMV.T691stop. Placque-purified recombinant adenoviral particles expressing T691stop neu were generated. Our laboratory confirmed functional expression of T691stop mutant neu proteins after infection of human cancer cells with adenoviral recombinant particles by flow cytometric analysis. Thus, a recombinant pure adenoviral recombinant which expresses high levels of T691stop neu in human cancer cells has been isolated and may be used as an anti-cancer reagent. T691stop neu-expressing adenoviral recombinants with alterations in the viral backbone making viral recombinant administration more suitable for human application have been designed. Specifically, adenoviral recombinants that contain the E1a deletion with an additional deletion of the E4 region have been made (See Example 7).

According to some preferred embodiments, the present invention provides anti-cancer gene therapy treatment to treat residual, local disease, as a therapeutic adjuvant in combination with preexisting treatments. Delivery is local at the time of surgery, most likely after the resection of all gross disease. For primary malignant brain tumors, gene therapy is given at the time of tumor resection or, in certain cases, by stereotactic implantation, a precise and standard method of local delivery or resection. Expression of T691stop neu is not cytocidal or toxic to nondividing cells. However, inhibition of erbB receptor signaling by T691stop neu mutant receptors renders a dividing tumor cell population more sensitive to the apoptotic cell death induced by irradiation. The T691stop neu form also induces a higher fraction of growth arrest in tumor cells treated with gamma-irradiation. Inhibition of growth factor-mediated signaling has been correlated with increased sensitivity to standard anti-cancer reagents in a number of systems.

Residual, local disease may be treated according to the present invention with a receptor-based strategy of growth inhibition which disables signaling through erbB family oncoproteins. This gene therapy strategy is part of a combined treatment regimen to achieve synergy of growth inhibition by direct (inhibition of receptor signaling) and indirect (i.e. by rendering cancer cells more sensitive to concurrent treatment with preexisting agents) mechanisms.

Many tumors are notable for either overexpression and/or mutation or erbB receptors, including the EGFR (erbB1), p185neu/erbB2, erbB3, and/or erbB4. In many cases, coexpression of erbB family members result in synergistic signaling and contributes to cell transformation. Tumors notable for p185neu/erbB2 overexpression include breast, ovarian, lung, and pancreatic cancer. Tumors notable for EGFR overexpression include primary glial brain tumors and prostate cancers. Gene delivery of truncated p185neu forms, i.e. T691stop neu cDNAs or proteins, provide a rationale strategy for the treatment of residual, local disease in these human cancers.

The present invention is particularly useful to treat patients who have glial brain tumors, i.e. tumors characterized by glioblastomas. Such cells express a mutant form of EGFR typically associated with tumorigenicity. It has been discovered that the present invention is particularly useful to treat such patients.

In some embodiments, the nucleic acid sequences encoding the various rat p185 species are constructed from c-neu cDNA according to the procedures set forth in the Examples. Nucleic acid sequences encoding wt, truncated, and mutated rat p185 species are thus prepared. The nucleotide sequences of the prepared p185 constructs are verified by DNA sequencing. One skilled in the art would readily understand methods of constructing such nucleic acid constructs.

After preparing such constructs, they are transfected into suitable host cells within which they are expressed. One skilled in the art would readily comprehend the vast number of suitable host cells from which to use. Within these suitable host cells, the ability of the p185 species, produced from the prepared nucleotide construct, to dimerize with either p185 or EGFR is examined. Such examination may include immunoblotting, flow cytometry, SDS-PAGE analysis, as well as other techniques that are well known to those skilled in the art. In addition, the tyrosine kinase activity of the p185 species may also be evaluated. It is also within the knowledge of one skilled in the art to evaluate tyrosine kinase activity by a variety of techniques.

Once the lack of tk⁻ phenotype of the p185 species is established and the ability to dimerize with either EGFR or p185 is established, the nucleic acid sequence encoding the p185 species may be subcloned into a suitable expression vector for transfection in human cells. Alternatively, the nucleic acid sequence may be used in combination with another delivery means as set forth above.

According to one aspect of the invention, the nucleic acid molecule comprises a nucleic acid sequence that encodes a protein that lacks tyrosine kinase activity and dimerizes with human EGFR or human p185. The nucleic acid sequence may be either DNA or RNA. The nucleic acid sequence may encode any protein that dimerizes with human EGFR and/or p185 and which lacks tyrosine kinase activity. The nucleic acid sequence preferably encodes rat or human p185 species which may dimerize with human p185 or human EGFR and which also lacks tyrosine kinase activity. In some preferred embodiments, the nucleic acid sequence encodes a protein that comprise the ectodomain region of rat or human p185 species. Such proteins dimerize with erbB proteins such as human p185 or human EGFR and also lacks tyrosine kinase activity.

In some preferred embodiments, constructs include the rat neu transmembrane region. In some preferred embodiments, the rat neu transmembrane region contains a val→glu mutation at amino acid 664. The rat neu transmembrane region without the mutation at amino acid 664 is referred to as the "N" form and the rat neu transmembrane region with the mutation at amino acid 664 is referred to as the "T" form.

In some preferred embodiments of the present invention, the nucleic acid sequence encodes truncation species of rat p185. The present invention includes any truncation species of rat p185 comprising either N-terminal or C-terminal deletions which dimerizes with either human p185 or human EGFR and which lacks tyrosine kinase activity. In addition, truncation species comprising substituted amino acids may also be effective. However, truncation species must be able to dimerize with human p185 or human EGFR. Thus, any portion of p185 that is able to dimerize with either human p185 or human EGFR while also having a tk⁻ phenotype is included herein. Preferably, the nucleic acid sequence encodes a protein consisting of amino acid residues of rat p185 from about 1–690 to about 1–740. In some preferred embodiments comprise the N form of the transmembrane region while in others, the T form is present.

In another preferred embodiment of the present invention, the nucleic acid sequence encodes species of rat p185 which lack tyrosine kinase activity by means of substitution or deletion of portions of amino acids, specifically those within the region of the molecule responsible for the tyrosine kinase activity. The present invention includes any tk⁻ species of rat p185, comprising either substitution or deletion of amino acids responsible for tk activity, wherein the species also dimerizes with human p185 or human EGFR. In addition, such species comprising substituted amino acids outside tk-associated sequences may also be effective. In some preferred embodiments comprise the N form of the transmembrane region while in others, the T form is present.

Positions 753–758 of rat p185 comprise the critical lysine residue which directly binds the ATP molecule that is the phosphate donor in the tyrosine kinase reaction (Moller et al, *FEBS Lett.*, 1985, 186, 1; and Sternberg et al., *FEBS Lett.*, 1984, 175, 387 each of which is incorporated herein by reference). Lys$^{757}$ is 15 amino acid residues downstream of a conserved motif which is also found in nucleotide binding proteins without kinase activity (Wierenga et al., *Nature*, 1983, 302, 842 which is incorporated herein by reference). It is believed that the glycine residues form a hydrophobic pocket around the critical lysine residue which directly binds the ATP molecule (Moller et al., *FEBS Lett.*, 1985, 186, 1; and Sternberg et al., *FEBS Lett.*, 1984, 175, 387 each of which is incorporated herein by reference). Thus, any species of p185 which comprises a disruption in the ATP binding domain or surrounding region, wherein ATP no longer binds to the critical Lys residue, are included herein. However, these species must also dimerize with human p185 or human EGFR. Preferably, the nucleic acid sequence encodes a protein having the amino acid sequence of rat p185, which is set forth in GENEBANK Acession No. X03362, which is incorporated herein by reference, and Bargmann, et al. (1986) *Nature* 319, 226–230, MEDLINE Identifier:86118662; and Lofts, et al. (1993) *Oncogene* 8, 2813–2820; each of which is incorporated herein by reference, wherein this amino acid sequence contains a substitution or deletion, or any combination thereof, from about position 753 to about 758, wherein said substitution does not comprise a lysine residue. In some preferred embodiments comprise the N form of the transmembrane region while in others, the T form is present.

In another preferred embodiment of the present invention, the nucleic acid sequence encodes rat p185 wherein the amino acid sequence contains a substitution or deletion at position 757. This substitution or deletion specifically removes the critical Lys residue at this position. Thus, ATP can no longer bind this molecule resulting in a tk⁻ phenotype. In some preferred embodiments comprise the N form of the transmembrane region while in others, the T form is present.

In another preferred embodiment of the present invention, the nucleic acid sequence encodes truncation species of human p185. The present invention includes any truncation species of human p185 comprising either N-terminal or C-terminal deletions which dimerizes with either human p185 or human EGFR and which lacks tyrosine kinase activity. In addition, truncation species comprising substituted amino acids may also be effective. However, truncation species must be able to dimerize with human p185 or human EGFR. Thus, any portion of human p185 that is able to dimerize with either human p185 or human EGFR while also having a tk⁻ phenotype is included herein. Preferably, the nucleic acid sequence encodes a protein consisting of amino acid residues of human p185 from about 1–646 to about 1–704. In some embodiments, the nucleic acid sequence encodes a protein consisting of amino acid residues of human p185 from about 1–653.

In another preferred embodiment of the present invention, the nucleic acid sequence encodes species of human p185 which lack tyrosine kinase activity by means of substitution or deletion of portions of amino acids, specifically those within the region of the molecule responsible for the tyrosine kinase activity. The present invention includes any tk⁻ species of human p185, comprising either substitution or deletion of amino acids responsible for tk⁻ activity, wherein the species also dimerizes with human p185 or human EGFR. In addition, such species comprising substituted amino acids outside tk-associated sequences may also be effective.

Positions 749–754 of human p185 comprise the critical lysine residue which directly binds the ATP molecule that is the phosphate donor in the tyrosine kinase reaction. Any species of p185 which comprises a disruption in the ATP binding domain or surrounding region, wherein ATP no longer binds to the critical Lys residue, are included herein. However, these species must also dimerize with human p185 or human EGFR. Preferably, the nucleic acid sequence encodes a protein having the amino acid sequence of human p185, which is set forth in GENEBANK Acession No. X03363 which is incorporated herein by reference, and Yamamoto, et al. (1986) *Nature* 319, 230–234, MEDLINE identifier: 86118663, and Papewalls, et al. (1991) *Nucleic Acids Res.* 19, 5452–5452, MEDLINE Identifier: 92020265, each of which is incorporated herein by reference, wherein this amino acid sequence contains a substitution or deletion, or any combination thereof, from about position 749 to about 754, wherein said substitution does not comprise a lysine residue.

In another preferred embodiment of the present invention, the nucleic acid sequence encodes human p185 wherein the amino acid sequence contains a substitution or deletion at position 753. This substitution or deletion specifically removes the critical Lys residue at this position. Thus, ATP can no longer bind this molecule resulting in a tk⁻ phenotype.

In some embodiments, the nucleic acid encodes a human EGFR protein, a human p185 protein, a human erbB3-derived protein or a human erbB4-derived protein. In some embodiments, the nucleic acid encodes a fusion protein. The fusion protein is encoded by chimeric sequences derived from human and non-human, particularly rat, sequences.

In some embodiments, the nucleic acid is selected from the group consisting of:

a truncated rat neu with a stop codon at amino acid 691 (N691stop construct);

a truncated rat neu with a stop codon at amino acid 691 and a val→glu mutation at amino acid 664 (T691stop construct);

a chimeric p185 gene comprising human p185c-erbB2 ectodomain linked to rat neu transmembrane with a stop codon at amino acid 691 (N691stop construct);

a chimeric p185 gene comprising human p185c-erbB2 ectodomain linked to rat neu transmembrane with a stop codon at amino acid 691 and a val→glu mutation at amino acid 664 (T691stop construct);

a chimeric p185 gene comprising human EGFR ectodomain linked to rat neu transmembrane with a stop codon at amino acid 691 (N691stop construct);

a chimeric p185 gene comprising human EGFR ectodomain linked to rat neu transmembrane with a stop codon at amino acid 691 and a val→glu mutation at amino acid 664 (T691stop construct);

a chimeric p185 gene comprising human erbB3 ectodomain linked to rat neu transmembrane with a stop codon at amino acid 691 (N691stop construct);

a chimeric p185 gene comprising human erbB3 ectodomain linked to rat neu transmembrane with a stop codon at amino acid 691 and a val→glu mutation at amino acid 664 (T691stop construct);

a chimeric p185 gene comprising human erbB4 ectodomain linked to rat neu transmembrane with a stop codon at amino acid 691 (N691stop construct); and, a chimeric p185 gene comprising human erbB4 ectodomain linked to rat neu transmembrane with a stop codon at amino acid 691 and a val→glu mutation at amino acid 664 (T69stop construct).

Unlike non-transformed replicating cells which can be killed by exposure to therapeutic radiation, tumor cells are resistant to induction of cell death by radiation. It has now been discovered that by disrupting the multimeric ensembles which produce elevated kinase activity associated with the transformed phenotype of a tumor cell, such a tumor cell, which is ordinarily resistant to radiation induced cell death, becomes sensitive to radiation. Accordingly, one aspect of the present invention provides methods of making radiation-resistant tumor cells radiation-sensitive. The present invention relates to methods of treating an individual who has tumor cells that have multimeric receptor ensembles which provide kinase activity associated with a transformed phenotype. The method comprises the step of first administering to the patient, a composition that disrupts the kinase activity associated with the multimeric receptor ensemble. The patient is then treated with gamma radiation.

There are several known receptor ensembles which, in tumor cells, display elevated kinase activity that is associated with the transformed phenotype. Members of the erbB family of receptors are known to form multimeric ensembles which result in elevated tyrosine kinase activity in tumor cells. Multimeric ensembles involving erbB family members include erbB homodimers as well as erbB heterodimers comprising monomeric components from different erbB family members. Multimeric receptor ensembles of platelet derived growth factor receptors (PDGFR) also display elevated kinase activity that is associated with the transformed phenotype.

According to one aspect of the present invention, dimer formation of erbB proteins in erbB mediated tumor cells is disrupted to render such cells more susceptible to cell destruction using radiation. Accordingly, combination therapies are provided that comprise first administering to an individual a composition which comprises an active agent that results in interference of erbB dimerization followed by exposing the patient to therapeutic amounts of radiation. According to these aspects of the invention, methods for treating individuals who have an erbB protein mediated tumor are provided. The methods comprise the steps of first administering to the individual a composition which inhibits elevated tyrosine kinase activity that results from dimerization of erbB proteins in a tumor cell, followed by, after a period of time sufficient for the composition to inhibit the tyrosine kinase activity associated with dimerization of erbB proteins from the tumor cell, exposing the individual to a therapeutically effective amount of anti-cancer radiation.

In some tumor cells, the p185 translation product of c-erbB2 gene is over expressed and forms homodimers and heterodimers with other erbB family members. Such dimerization of overexpressed p185 leads to elevated tyrosine kinase activities which is associated with the transformed phenotype. Disruption of tyrosine kinase activity, such as by inhibiting dimer formation between monomeric components, results in a cytostatic effect on the tumor cells. It has now been discovered that the disruption also renders the previously radiation resistant tumor cells radiation-sensitive.

Similarly, in some tumor cells, a mutant form of EGFR (ΔEGFR) is expressed which is ligand-independent. ΔEGFR forms homodimers and heterodimers with wild-type EGFR and other erbB family members. Such dimerization of ΔEGFR leads to elevated tyrosine kinase activities which is associated with the transformed phenotype. Disruption of tyrosine kinase activity, such as by inhibiting dimer formation between monomeric components, results in a cytostatic effect on the tumor cells. It has now been discovered that the disruption also renders the previously radiation resistant tumor cells radiation-sensitive.

In some embodiments, the erbB-protein mediated tumor is a brain cancer tumor. In some preferred embodiments, the erbB-protein mediated tumor is a glial tumor. In some preferred embodiments, the erbB-protein mediated tumor is a glioblastoma. In some embodiments, the erbB-protein mediated tumor is a breast cancer tumor. In some embodiments, the erbB-protein mediated tumor is an ovarian cancer tumor. In some embodiments, the erbB-protein mediated tumor is a pancreatic cancer tumor.

In some embodiments, the kinase activity associated with the multimeric receptor ensemble is disrupted by administering to the individual a composition that comprises an active agent which interact is with a monomeric component of the ensemble, and in doing so, prevents dimerization by physically altering the monomer so that it is less thermodynamically disposed to form the ensemble. Such physical alterations may be, for example, conformational, steric, and/or electrostatic changes which render the monomer in a condition less favorable for dimer formation. Examples of active agents which physically alter the monomer include antibodies, proteins, peptides and non-proteinaceous molecules.

As used herein, the term "antibody" is meant to refer to antibodies, as well as antibody fragments such as FAb and F(Ab)$_2$ fragments. Antibodies may, in some preferred embodiments, be monoclonal antibodies or humanized antibodies. Antibodies against p185 are described in U.S. Pat. No. 5,677,171 issued Oct. 14, 1997 which is incorporated herein by reference, and U.S. Pat. No. 5,705,157 issued Jan. 6, 1998, which is incorporated herein by reference, and which also describes antibodies against EGFR. U.S. Pat. No. 5,470,571 issued Nov. 28, 1995, which is incorporated herein by reference, also describes antibodies against EGFR.

In some embodiments, peptides are provided which mimic antibodies are provided to inhibit multimeric ensemble formation and the elevated kinase activity associated which such formation. For example, peptides are designed which have sequences corresponding to CDR regions from antibodies. Methods of making such peptides are also described in Ser. No. 08/257,783 filed Jun. 10, 1994 and PCT Application No. PCT/US95/07157 filed Jun. 6, 1995 which is incorporated herein by reference. Peptidomimetics of antibodies against p185 are described in U.S. Pat. No. 5,663,144 issued Sep. 2, 1997, which is incorporated herein by reference.

According to some embodiments of the invention, the composition that is administered to the individual to disrupt the kinase activity associated with the multimeric receptor ensemble comprises an active agent that is a nucleic acid molecule that encodes a kinase deficient protein or peptide which interacts with a monomeric component of said ensemble to prevent it from interacting with another component of the ensemble. That is, the nucleic acid molecule encodes a kinase deficient protein which competes with the endogenous proteins of the cell to form multimeric complexes. Complexes formed between the kinase deficient protein and the cell's endogenous proteins do not provide elevated kinase activity. Thus, the kinase deficient proteins act as decoys to tie up endogenous proteins and thereby preventing formation of kinase active multimeric complexes. Examples of such nucleic acid molecules are described in Ser. No. 08/737,269 filed Feb. 11, 1997, which is incorporated herein by reference, and throughout this disclosure.

According to some methods, the composition that is administered to a patient that comprises a compound that competitively interacts with an erbB protein in a tumor cell to competitively inhibit dimer formation with another erbB protein to a decrease dimerization of erbB proteins is a nucleic acid molecule that encodes a protein. The protein blocks dimer formation by competitively interacting with an erbB protein. In some embodiments, the protein interacts with the transmembrane region of said one erbB protein. In some such embodiments, the protein that interacts with the transmembrane region of one erbB protein comprises a rat neu transmembrane region with a val to glu mutation at amino acid 664. In some embodiments, the protein interacts with the ectodomain region of one erbB protein. In some such embodiments, the protein that interacts with the ectodomain region of one erbB protein comprises a p185 ectodomain. In some preferred embodiments, the nucleic acid molecule that encodes the protein is a viral genome. In some preferred embodiments, it is a genome of a recombinant adenovirus. According to some embodiments, the nucleic acid molecule comprises a coding sequences operably linked to regulatory elements for translation in cells of said individual. In some embodiments, the coding sequence comprising sequences selected from the group consisting of: a truncated rat neu gene with a stop codon at amino acid 691; a truncated rat neu gene with a stop codon at amino acid 691 and a val→glu mutation at amino acid 664; a chimeric p185 gene comprising human p185c-erbB2 ectodomain linked to rat neu transmembrane with a stop codon at amino acid 691; a chimeric p185 gene comprising human p185c-erbB2 ectodomain linked to rat neu transmembrane with a stop codon at amino acid 691 and a val→glu mutation at amino acid 664; a chimeric p185 gene comprising human EGFR ectodomain linked to rat neu transmembrane with a stop codon at amino acid 691; a chimeric p185 gene comprising human EGFR ectodomain linked to rat neu transmembrane with a stop codon at amino acid 691 and a val→glu mutation at amino acid 664; a chimeric p185 gene comprising human erbB3 ectodomain linked to rat neu transmembrane with a stop codon at amino acid 691; a chimeric p185 gene comprising human erbB3 ectodomain linked to rat neu transmembrane with a stop codon at amino acid 691 and a val→glu mutation at amino acid 664; a chimeric p185 gene comprising human erbB4 ectodomain linked to rat neu transmembrane with a stop codon at amino acid 691; and, a chimeric p185 gene comprising human erbB4 ectodomain linked to rat neu transmembrane with a stop codon at amino acid 691 and a val→glu mutation at amino acid 664.

In some embodiments, nucleic acid molecules encode peptides which interact with transmembrane regions of erbB proteins and thus prevent dimerization of erbB proteins. Examples of such nucleic acid molecules are disclosed in Lofts, et al. 1993 *Oncogene* 8:2813–2820, which is incorporated herein by reference.

According to some preferred embodiments, the composition that comprises an active agent which causes disruption of the kinase activity associated with the multimeric receptor ensemble is administered by any route of administration which can be used to deliver the agent to the tumor. In some embodiments, the composition is administered by intravenous, intraarterial, intramuscular, intradermal, subcutaneous, parenteral, or intratumoral administration. According to some preferred embodiments, the individual has had surgery to remove bulk tumor mass prior to administration of the composition.

According to aspects of the present invention, after administering the composition that comprises an active agent which causes disruption of the kinase activity associated with the multimeric receptor ensemble; the individual is then exposed to a therapeutic amount of gamma radiation. Radiation therapy may commence anytime after a sufficient amount of time has elapsed for the active agent to cause disruption of the kinase activity associated with the multimeric receptor ensemble. Generally, the individual is exposed to radiation in some cases 1–10 minutes after, in some cases 1–10 hours after, and in some cases up to 24–72 hours after administration of the active agent. In some cases, the radiation is provided in a single dose while in some embodiments, multiple doses are administered over several hours, days and/or weeks. The active agent renders the radiation resistant tumor cells radiation sensitive. Thus, once the active agent inhibits the kinase activity, exposure to radiation may follow suit. Gamma radiation is delivered according to standard radiotherapeutic protocols using standard dosages and regimens. The administration of the active agent renders the radiation more effective in eradicating tumor cells.

According to aspects of the present invention, after administering the composition that comprises an active agent which causes disruption of the kinase activity associated with the multimeric receptor ensemble; the individual is then administered a cytotoxic chemotherapeutic agent in addition to or in lieu of exposure to a therapeutic amount of gamma radiation. As in the case of radiation therapy, chemotherapy may commence anytime after a sufficient amount of time has elapsed for the active agent to cause disruption of the kinase activity associated with the multimeric receptor ensemble. Generally, the individual is administered the chemotherapeutic in some cases 1–10 minutes after, in some cases 1–10 hours after, and in some cases up to 24–72 hours after administration of the kinase inhibiting active agent. In some cases, the chemotherapeutic is provided in a single dose while in some embodiments, multiple doses are administered over several hours, days and/or weeks. The active agent renders the tumor cells more sensitive to cytotoxic agents. Thus, once the active agent inhibits the kinase activity, administration of chemotherapeutics may follow suit. Chemotherapeutics are delivered according to standard radiotherapeutic protocols using standard agents, dosages and regimens. In some embodiments, the chemotherapeutic is selected from the group consisting of: cisplatin, doxirubicin, danurubicin, tamoxiphen, taxol, and methotrexate. In some embodiments, chemotherapy and radiation treatments are both employed following the administration of the active agent. In such embodiments, standard combinations of the two therapeutic modalities are used in conjunction with administration of the kinase inhibiting active agent.

The present invention is not intended to be limited by any theory. The present invention is further illustrated by the following examples, which are not intended to be limiting in any way.

EXAMPLES

Example 1

Construction of Mutants, Expression Vectors and Creation of Cell Lines

Detailed methods for the construction of mutant p185 species, expression vectors and cell lines have been described previously (Qian et al., *Proc. Natl. Acad. Sci. USA*, 1994, 91, 1500; and Weiner et al., *Oncogene*, 1989, 4, 1175, each of which is incorporated herein by reference).

Construction of Mutant N757

The ATP-binding mutant Nneu K757M (N757) was derived from pSV2TneuK757M (Weiner et al., *Oncogene*, 1989, 4, 1175, which is incorporated herein by reference) by subcloning techniques. This construct was prepared by site-directed mutagenesis to substitute a Met for Lys$^{757}$. One skilled in the art would readily understand the preparation of a such a mutant by site-directed mutagenesis. Briefly, an Xba1 fragment of pSV2neuT corresponding to a 1.2 kb band spanning the probable ATP binding site of the published nucleotide sequence was cloned into M13Mp18 and transfected into *E. coli* strain CJ236 (dot⁻, ung⁻) pUC13 so that the HindIII site of the polylinker fell at the 5' end of the inserted sequences. Mutagenesis was performed as described utilizing a primer in which the codon AAG, coding for Lys, was replaced by the codon AUG corresponding to Met (Bargmann et al., *Nature*, 1986, 319, 226, which is incorporated herein by reference). The point mutations thus created were verified by DNA sequencing. The plasmid bearing the novel mutation was cleaved with Xba1 which liberated the original fragment. This fragment was isolated by standard techniques known to those skilled in the art and ligated back into pSV2-neu to regenerate the oncogenic p185neu expression vector except that the vector contained the substitution of Met for Lys at amino acid position 757 (clone M757).

Construction of Mutant N691stop

The carboxy-terminal 591 amino acid deletion mutant N691stop was derived from pSV2Nneu (Bargmann et al., *Nature*, 1986, 319, 226, which is incorporated herein by reference) by substitution of a stop codon for normal codon Thr$^{691}$ via site-directed mutagenesis.

Construction of Ndx

The carboxy-terminal 541 amino acid deletion mutant Ndx was derived from c-neu cDNA by the deletion of an XbaI fragment and insertion of a stop codon for the normal codon at position 741 via site-directed mutagenesis.

Construction of Expression Vectors

For expression vectors, fragments containing mouse dihydrofolate reductase (DHFR) cDNA from pSV2DHFR and bacterial neomycin phosphotransferase-resistant gene (neo$_r$) from pSV2NEO (Southern et al., *J. Mol. Appl. Genet.*, 1982, 1, 327, which is incorporated herein by reference) were subcloned into pSV2Nneu so that a 14.8 kb DHFR, neo$^r$, and Nneu cDNA combined vector was generated. The wt or mutated neu fragments were isolated and ligated back into a pSV2neo$^r$/dhfr/Nneu expression vector. All these cDNAs were under the control of the simian virus 40 (SV40) early promoter. A gene unit encoding the bacterial hygromycin-resistance (Hyg$^r$) gene under the control of herpes simplex virus thymidine kinase promoter was isolated from pHyg and substituted for a neo$^r$ gene fragment in pEGFR1 (Gorman et al., *J. Cell. Biochem.*, 1988, 12A, Suppl., C219, which is incorporated herein by reference) to generate another combined expression vector, pEGFR/Hyg$^r$. Human EGFR cDNA was under the control of the SRα promoter, an efficient transcriptional control element containing SV40 early promoter and the R-U5 segment of human T-cell leukemia virus type 1 long terminal repeat (Takebe et al., *Mol. Cell. Biol.*, 1988, 8, 466, which is incorporated herein by reference).

Transfection and Maintenance of Cell Lines

The construct pEGFR/Hyg$^r$ was first transfected into NR6 cells (Pruss et al., *Proc. Natl. Acad. Sci. USA*, 1977, 74, 3918, which is incorporated herein by reference) by calcium phosphate precipitation. After 3 weeks of hygromycin selection (35 μg/ml), the EGFR expression of resultant colonies was identified by anti-EGFR immunoblotting. Cells that expressed EGFR were further cloned by limiting dilution prior to second round transfection with neu cDNA expression vectors. The EGFR-expressing cells, named NE91, together with NR6 cells, were transfected with pSV2neo$^r$/dhfr/neu encoding wt or mutant neu proteins and selected with G418. The Neu-expressing clones in NR6 cells and NE91 cells were screened by flow cytometric assay with anti-neu monoclonal antibody 7.16.4 staining (Drebin et al., *Cell*, 1985, 41, 695, which is incorporated herein by reference) and were named NR6 Neu and NE Neu, respectively. These DHFR-containing single (expressing Neu only) or double (expressing Neu and EGFR) transfected clones were maintained in Dulbecco's modified Eagle's medium (DMEM) containing 5% fetal bovine serum, G418 (0.3 mg/ml), and hygromycin (15 μg/ml). Neu amplification was achieved by stepwise increased dosages (0.3–1.0 μM) of methotrexate for a few months in order to elevate receptor expression level.

Flow Cytometry

Cells were removed from tissue culture dishes with buffered EDTA (Versene, M.A. Bioproducts) and washed twice in FACS medium (Hanks' balanced salt solution (Gibco) supplemented with 2% fetal calf serum, 0.2% sodium azide, and 10 mM HEPES). 1×10$^6$ cells were incubated in 0.1 ml of FACS medium with 7.16.4, anti-neu monoclonal antibody (Drebin et al., *Cell*, 1985, 41, 695, which is incorporated herein by reference) or isotype matched irrelevant control antibody for 1 hour at 4° C. The cells were washed twice with 2.5 ml of FACS medium. The cell pellet was resuspended and cells were incubated with 0.1 ml of FITC-conjugated goat rabbit anti-mouse IgG (reactive with antibody heavy and light chains, Tago) diluted 1:50 in FACS medium, for 1 hour at 4° C. Cells were washed twice and analyzed on a FACS IV Becton Dickenson.

Example 2

Tyrosine Kinase Activity

Membrane Purification

Cells were lysed by a combination of snap freeze-thawing and Dounce homogenization as described in Gaulton et al., *J. Immunol.*, 1986, 7, 2470, which is incorporated herein by reference. The nuclear fraction was removed by centrifugation at 2000×g for 5 minutes. The 2000×g supernatant fraction was then recentrifuged at 25000×g for 30 minutes at 4° C., and the 25000×g supernatant was retained as the cytosol fraction. The pellet was redissolved in 1.5 ml of membrane buffer (40 mM NaCl, 0.1 mM EDTA, 20 mM HEPES (pH 6.8), 2 mM PMSF, and 5 mM Na pyrophosphate) then layered over a (20%–37%) sucrose solution in membrane buffer and centrifuged at 22000 rpm for 18 hours at 2° C. by using a Beckman SW50.1 rotor. The membrane-rich interface was removed in 1 ml total volume, diluted with 10 ml of membrane buffer, and was recentrifuged at 40000 rpm for 60 minutes by using an SW40.1 rotor exactly as described in Zick et al., *Biochem. Biophys. Res. Commun.*, 1984, 119, 6, which is incorporated herein by reference. The resultant pellet containing purified membrane fragments, was redissolved in 100 $\mu$l of Kinase buffer (see below) per $10^7$ original cells. Membrane proteins were quantitated using a BioRad protein assay kit and stored at −80° C. until assay.

Tyrosine Kinase Activity in Membranes

Membrane concentrations were determined by the method of Bradford as described in Gaulton et al., *J. Immunol.*, 1986, 7, 2470, which is incorporated herein by reference. Dilutions of membranes were incubated in quadruplicate in the presence or absence of synthetic polypeptide containing tyrosine as a specific indicator of tyrosine phosphorylation. Kinase reaction buffer, (50 $\mu$l of 0.1 M Hepes pH 7.3, 10 mM $MgCl_2$, 5 mM $MnCl_2$, 50 $\mu$M $Na_3VO_4$ were incubated in the presence of ATP (1 $\mu$Ci of gamma [$^{32}$P]ATP; Amersham) for 5 minutes at room temperature. Reactions were halted by adding 5 mM EDTA (final concentration) followed immediately by TCA immunoprecipitation onto glass fiber filters (Whatman GF/A). Filters were washed extensively with TCA followed by ether, air-dried, immersed in scintillation cocktail (Biofluor) and beta emissions determined. Quadruplicate wells assayed in the absence of tyrosine containing substrate were subtracted from tyrosine substrate containing wells.

Membrane proteins were incubated with the random polymer of glutamic acid-tyrosine (4:1) poly glu:tyr, PGT) as substrate for tyrosine phosphorylation as described in Zick et al., *Biochem. Biophys. Res. Commun.*, 1984,119, 6, which is incorporated herein by reference. Briefly, membrane proteins were incubated in 50 $\mu$l of 10 mM HEPES pH 7.2, containing 10 mM $MgCl_2$, 100 $\mu$M $Na_3VO_4$, and 150 $\mu$M (10 $\mu$Ci) [$^{32}$P]ATP for 15 minutes at room temperature in the presence (specific) or absence (background) of poly glu:tyr substrate at 2.5 mg/ml. Reactions were stopped by the addition of EDTA to 50 mM final concentration and cold excess ATP and samples were spotted onto Whatman glass fiber filter paper. Filters were washed 3 times with ice cold 10% TCA containing 10 mM pyrophosphate and 1 mM ATP followed by once with acetate. Samples were then dried and counted in BioFlur (NEN). For immunoprecipitation of phosphotyrosine containing membrane proteins, 50 $\mu$g of purified membranes were incubated in kinase buffer as described above for 15 minutes. After labeling, samples were solubilized in Lysis buffer supplemented with 5 mM EDTA, precleared and immune precipitated with 2 $\mu$l ascites from MA-2G8A6+protein A agarose. The MA-2G8 antibody specifically precipitates phosphotyrosine labeled polypeptides as described in Daniel et al., *Proc. Natl. Acad. Sci. USA*, 1985, 82, 2084, which is incorporated herein by reference.

Example 3

Dimerization with p185 or EGFR

EGFR and p185 heterodimers are detected by anti-receptor-specific antibody immunoprecipitation and immunoblotting after EGF and chemical cross-linker treatment. The physical association of EGFR and kinase-deficient p185 proteins were examined in this manner.

Chemical Cross-linking Assay

Cells were cultured overnight in 10 cm Petri dishes, incubated with or without EGF (GIBCO/BRL) at 37° C. for 10–15 minutes, and washed twice with cold phosphate buffered saline (PBS). Three ml of PBS containing 2 mM bis(sulfosuccinimidyl) suberate ($BS^3$) or 3,3'-dithiobis (sulfosuccinimidylpropionate) (DTSSP) (Pierce) was added and incubated at 18° C. for 30 minutes with occasional rocking of the plates. After quenching the crosslinking reaction mixture with buffer containing 10 mM Tris-HCl, 0.9% NaCl, and 0.1 M glycine, cells were washed twice with cold PBS and solubilized with PI/RIPA buffer (Wada et al., *Cell*, 1990, 61, 1339, which is incorporated herein by reference).

Labeling and Immunoprecipitation

All reagents were obtained from Sigma unless otherwise indicated. For [$^{32}$P]-labeling 1×$10^6$ cells were plated and were cultured for 24 hours and then were incubated with inorganic [$^{32}$P] (Amersham) at 0.5 mCi/ml in 5% FCS/phosphate-free RPMI for 6 hours. After labeling cells were washed with cold phosphate buffered saline containing 400 $\mu$M EDTA, 10 mM sodium fluoride, 10 mM sodium pyrophosphate and 400 $\mu$M sodium orthovanadate and were lysed in lysis buffer (1% NP40, 0.1% deoxycholate, 0.1% SDS, 0.15 M NaCl, 0.01 M sodium phosphate pH 7.4, 1% Trasylol, 1 mM PMSF, 2 mM EDTA, 10 mM sodium fluoride, 10 mM sodium pyrophosphate, 400 $\mu$M $Na_3VO_4$, 10 mM iodoacetoamide and 1 mM ATP) for 30 minutes. Pre-cleared supernatants were subjected to immunoprecipitation with monoclonal antibody 7.16.4, or rabbit antisera recognizing human and rat neu proteins DBW-2 (Kokai et al., *Proc. Natl. Acad. Sci. USA*, 1988, 84 8498, which is incorporated herein by reference). Immunoprecipitates were boiled in Laemmli's sample buffer and analyzed in 8% SDS-PAGE (Laemmli, *Nature*, 1970, 227, 680, which is incorporated herein by reference). Dried gels were exposed to prefogged film at −70° C. Densitometer tracings of gels were performed on a Hoefer GS300 scanning densitometer. Relative densities were determined by cutting out in side by side experiments the relevant scanned peaks and weighing them on an analytical balance. The incorporation of the proto oncogenic and oncogenic p185neu was then directly compared.

Focus Formation and Tumorigenicity Assays

Cells ($10^4$) were plated in Petri dishes and cultured in DMEM containing 2% FBS. The medium was changed every 3–4 days. After 3 weeks in culture, cells were fixed with 10% formalin and stained with hematoxylin to observe morphologically transformed foci. To analyze the tumor growth in athymic nude mice, cells ($10^6$) of each line were suspended in 0.1 ml of PBS and injected intradermally in the mid-dorsum of NCR nude mice. PBS alone was also injected as a control. Tumor growth was monitored every 4–5 days up to 10–12 weeks.

Results

NE91 is a transfected cell line expressing the EGFR in NR6 cells (Pruss et al., *Proc. Natl. Acad. Sci. USA*, 1977, 74, 3918, which is incorporated herein by reference), a mouse fibroblast cell line devoid of endogenous EGFR. Wildtype (WT) cellular p185 (Nneu) or kinase deficient Neu (i.e. N757 and N691stop, carrying a point mutation K757M at the ATP-binding site and cytoplasmic domain deletion, respectively), were expressed in both NR6 and NE91 cells. The resultant transfected clones were named NR6 Neu or NE Neu, respectively.

Kinase Deficient Mutant Neu Proteins Suppressed EGFR Function in Cellular Transformation and Abolished the Transforming Synergy with EGFR We have previously shown that co-expression of increased levels of EGFR and cellular p 185, but not either separately, transformed murine fibroblast cells completely as demonstrated with the M1 cell line (Kokai et al., *Cell*, 1989, 58, 287, which is incorporated herein by reference). In the present study, the transformed phenotypes of these transfected cells expressing WT or kinase deficient Neu proteins in the presence or absence of EGF were analyzed.

NE91 cells expressing EGFR alone formed a monolayer in the absence of EGF and foci in the presence of EGF. The observed incomplete transformation, (i.e., in an EGF-dependent manner), is in agreement with previous reports (DiFiore et al., *Cell*, 1987, 51, 1063; Dobashi et al., *Proc. Natl. Acad. Sci. USA*, 1991, 88, 8582, each of which is incorporated herein by reference). However, in a similar manner to M1 cells, co-expression of WT cellular p185 and EGFR in NE NneuB2 cells resulted in complete transformation, i.e., the focus formation was EGF-independent. Cell lines co-expressing EGFR with either form of kinase deficient Neu (NE N757 and NE N691stop cells) did not form foci even in the presence of EGF. Similar results were observed when anchorage-independent colony growth in soft agar was assayed.

Tumor growth in nude mice was used as a criterion for complete transformation in vivo. B104-1-1 cells expressing oncogenic p185 were used as a positive control and tumors caused by those cells appeared quickly (with a latency of 5 days). Cell lines expressing equivalent levels of EGFR (NE91) or cellular p 185 (NR6 Nneu) alone did not grow tumors. However, injection of the cells co-expressing both EGFR and cellular p185 (M1 and NE NneuB2) caused tumors (2–3 weeks latency). The results were consistent with a previous report (Kokai et al., *Cell*, 1989, 58, 287, which is incorporated herein by reference).

However, no tumors were observed (>10 weeks) after injection of cell lines expressing kinase deficient Neu alone or co-expressed with EGFR. These data suggested that the normal cellular p185 kinase activity and EGFR function was required for synergistic transformation and tumor formation. Co-expression of kinase deficient Neu proteins with EGFR not only abolished this type of synergy, but also suppressed the EGF-dependent transformation potential of EGFR. Therefore, EGF receptor function mediated by ligand stimulation was further analyzed in the following studies.

EGF-induced Receptor Down-regulation Was Less Efficient in Neu Kinase Deficient Mutant Cells We next examined whether normal receptor down-regulation was affected by co-expression with kinase deficient Neu. Cells were incubated with EGF for various times prior to cell surface staining with anti-neu mAb 7.16.4 or anti-EGFR mAb 425 followed by the staining with FITC conjugated anti-mouse-IgG. The cell surface expression of either receptor was analyzed using flow cytometric analysis. The cell surface expression of EGFR in NE91 cells was reduced after 15 minutes of EGF treatment and over 60% of receptors disappeared from the cell surface after 1 hour treatment. The efficiency of EGFR down-regulation in M1 cells (co-expressing WT Neu and EGFR) was similar to that observed in NE91 cells. About 20% of cellular p185 co-downregulated along with EGFR in M1 cells. Similar results were observed in NE Nneu B2 cells. However, cell lines expressing cellular p185 only did not respond to EGF. In cell lines in which EGFR was co-expressed with kinase deficient mutant Neu proteins the down-regulation of EGFR was less efficient (maximum reduction was about 20–25%). In addition, the surface expression of either mutant Neu protein was not altered significantly in these cells upon EGF treatment.

Increased Receptor Half-lives Observed in Kinase Deficient Mutant Neu Co-expressed Cells To determine whether the receptors that were down-regulated from the cell surface underwent degradation, pulse-chase labeling of receptor proteins was performed as described in materials and methods, and immunoprecipitated Neu and EGFR proteins were analyzed by SDS-PAGE. EGF treatment caused a rapid degradation of EGFR in NE91 cells (expressing EGFR alone). A similar EGFR degradation rate was observed in M1 cells upon EGF treatment. However, EGF-induced EGFR degradation was slowed in cells co-expressing EGFR with either form of Neu kinase deficient mutant (NE N757 or NE N691stop).

The degradation patterns of WT or mutant Neu proteins in response to EGF treatment were also investigated. The labeled WT cellular p185 in both M1 cells and NE NneuB2 cells disappeared proportionately to the time treated with EGF, indicating that WT cellular p185 is efficiently co-degraded with EGFR. There was only a slight reduction of N757 protein levels and no discernible change in the abundance of the truncated N691stop protein after EGF treatment up to 6 hours. The suggested normal half-life of human c-erbB2 in mammary epithelial cells is 11–13 hours (Kornilova et al., *Oncogene*, 1992, 7, 511, which is incorporated herein by reference). Densitometric analysis of our autoradiograms confirmed that the half life of WT cellular p185 was reduced to 3–4 hours after EGF treatment, while the mutant Neu levels did not change significantly over the time course examined.

EGF Binding Affinity in Wt or Mutant Neu Protein Expressed Cells

Our experiments have demonstrated that kinase deficient Neu mutants suppress EGFR functions, such as kinase activity (Qian et al., *Proc. Natl. Acad. Sci. USA*, 1994, 91, 1500, which is incorporated herein by reference), EGF-mediated transformation, receptor down-regulation and degradation. Since these effects could be interpreted, in part, by altered EGF binding affinities, we analyzed [$^{125}$I]-EGF binding parameters by Scatchard analysis.

The mean dissociation constants (Kd) of [$^{125}$I]-EGF binding to these cell lines were determined from three individual experiments. EGFR in NE91 cells displayed two binding components representing high ($7.5 \times 10^{-11}$M) and low (4.4×

$10^{-9}$M) binding affinities, and the fraction of high affinity receptors was 5.4% of the total receptors. Co-expression of EGFR with WT Neu in NE NneuB2 cells resulted in a slight increase in EGF binding affinities ($3.2\times10^{-11}$M) and ($2.0\times10^{-9}$M) for both high and low affinity subclasses, respectively, and the fraction of high affinity receptors was 5.7%. The increased affinities for M1 cells were reproducible and the Kd values ($1.3\times10^{-11}$M and $1.8\times10^{-9}$M) were in agreement with our previous reports, Kokai et al., Cell, 1989, 58, 287; and Wada et al., Cell, 1990, 61, 1339, each of which is incorporated herein by reference). However, the EGFR in kinase deficient Neu co-expressing cells displayed predominantly low affinity EGF binding, $4.9\times10^{-9}$M and $5.2\times10^{-9}$M in NE N691 and NE N757 cells, respectively, although a rare high affinity subclass of EGFR was sometimes detectable, i.e., $7.2\times10^{-11}$M (0.5%) in NE N691stopcells and $6.6\times10^{-11}$M ($\leq$1%) in NE N755 cells. These rare species may represent a set of EGFR homodimers still observed when co-expressed with kinase inactive Neu proteins (Qian et al., Proc. Natl. Acad. Sci. USA, 1994, 91, 1500, which is incorporated herein by reference). It is clear from the Scatchard analysis that EGFR in cells co-expressing kinase active WT Neu display the normal percentage of high affinity EGF receptors, with a slightly increased affinity for EGF when compared with NE91 cells. However, the co-expression of kinase deficient Neu protein greatly reduced the EGF-binding affinities in correlation with the reduced heterodimeric kinase activities.

Discussion

In the current studies, receptor functions and cell phenotypes have been analyzed by using stably transfected cell lines co-expressing EGFR with WT or mutant Neu proteins. Unlike WT Neu, the kinase deficient Neu did not cooperate with EGFR to mediate cell transformation; in addition, we have shown novel aspects of dominant negative receptor functions resulting from the interaction of mutant Neu with EGFR.

The intermolecular association and resultant tyrosine kinase activation between EGFR and WT (Qian et al., Proc. Natl. Acad. Sci. USA, 1992, 89, 1330, which is incorporated herein by reference) or mutant Neu proteins (Qian et al., Proc. Natl. Acad. Sci. USA, 1994, 91, 1500, which is incorporated herein by reference) have been well-characterized: our studies showed that heterodimerization of EGFR and c-neu products can be detected even in the absence of EGF, and are favored over either form of homodimerization. However, the homodimerization and co-dimerization of WT EGFR and cytoplasmic domain deleted EGFR were equally efficient and EGF-dependent (Kashles et al., Mol. Cell Biol., 1991, 11, 1454, which is incorporated herein by reference). The predominance of heterodimers may help to explain the resultant cell phenotypes, and inducible dominant negative effect of kinase deficient Neu on suppression of EGFR function, which occurred significantly even when there is a 1:1 ratio of EGFR and mutant Neu proteins.

Receptor interaction with resultant activation of the tyrosine kinase occurs by an intermolecular mechanism and is often followed by rapid transphorylation events as has been observed in pp60$^{c-src}$ (Cooper et al., Proc. Natl. Acad. Sci. USA, 1988, 85, 4232, which is incorporated herein by reference), insulin receptor (Boni-Schnetzler et al., J. Biol. Chem., 1988, 263, 6822, which is incorporated herein by reference) and EGFR (Honegger et al., Mol. Cell. Biol., 1990, 10, 4035, which is incorporated herein by reference). Transphosphorylation also occurs between hetero-receptor species, EGFR and Neu/c-erbB2 (Connelly et al., Proc. Natl. Acad. Sci. USA, 1990, 87, 6054; Spivak-Kroizman et al., J. Biol. Chem., 1992, 267, 8056; and Qian et al., Proc. Natl. Acad. Sci. USA, 1994, 91, 1500; each of which is incorporated herein by reference). Preferential heterodimerization of EGFR and Neu receptor (Qian et al., Proc. Natl. Acad. Sci. USA, 1994, 91, 1500, which is incorporated herein by reference) may facilitate transphosphorylation of N757 by EGFR. Currently, the specific substrates for the EGFR and Neu kinase have not been well-characterized. In vitro binding assays showed that the phosphorylated kinase deficient N757 was still able to associate with recombinant SH2-containing protein upon EGF-treatment. However, unlike active heterodimers in M1 and NE NneuB2 cells, the loss of Neu kinase activity of mutant heterodimer of NE N757 cells may prohibit the phosphorylation of certain cellular substrates. Furthermore, the predominant transphosphorylation of N757 by EGFR and the occupancy of cellular substrates in nonfunctional N757 may compete with EGFR for cellular signaling molecules leading to qualitative and quantitative reductions in EGFR function. Therefore, the defective heterodimer may not transmit signals as effectively as the kinase active heterodimer and EGFR homodimer, thus impairing the synergistic signaling that lead to cell transformation seen in M1 and NE NneuB2 cells and inhibiting EGFR function. Studies of heterodimerization of EGFR with cytoplasmic domain deleted N691stop showed that the heterodimer form was inactive due to the failure of protein-protein interaction between the cytoplasmic domains, indicating that Neu/c-erbB2 is not simply a substrate for EGFR, but a trans-activator for EGFR as well (Qian et al., Proc. Natl. Acad. Sci. USA, 1994, 91, 1500, which is incorporated herein by reference). Thus, the reduced amounts of normal EGFR homodimer form and the preponderance of unproductive heterodimers resulted in the suppression of normal EGFR function and resultant dominant negative phenotype. The observation is comparable to the effects of dimers formed between WT EGFR and cytoplasmic domain deleted EGFR (Kashles et al., MOl. Cell. Biol., 1991, 11, 1454, which is incorporated herein by reference).

Kinase active receptors have been reported to be targeted to lysosomes for degradation upon ligand binding (Chen et al., Cell, 1989, 59, 33; Felder et al., Cell, 1990, 61, 623, which is incorporated herein by reference). Previous studies using kinase-deficient insulin receptors (McClain et al., J. Biol. Chem., 1987, 262, 14663; and Russell et al., J. Biol. Chem., 1987, 262, 11833; each of which is incorporated herein by reference) and EGFR (Honegger et al., Cell, 1987, 51, 199, which is incorporated herein by reference) suggested that active kinase domains are essential for normal ligand-induced receptor routing. We used EGF-treated cell lines to study how the activities of receptor kinase complexes correlate with receptor endocytosis and destruction. Our work demonstrates that EGFR is WT Neu co-expressed cells (M1 or NE NneuB2) undergoes rapid down-regulation and degradation upon EGF stimulation. This process was significantly retarded in mutant cells compared to the NE91 cells expressing EGFR alone. Only the WT cellular p185, but not the kinase deficient mutant Neu protein, was co-downregulated and co-degraded with EGFR. Similarly, EGF-treatment of the human mammary cell line HC11 cells affected c-erbB2 protein surface expression and protein turnover: a 3–4 fold increase in the lysosomal c-erbB2 protein and the half-life of c-erbB2 proteins was reduced from 11 hour (untreated) to 3.5 hour (EGF-treated) (Kornilova et al., Oncogene, 1992, 7, 511, which is incorporated herein by reference). Together with our observation, these results suggested that WT Neu/c-erbB2, (but not kinase deficient Neu), associates with EGFR and an active receptor tyrosine kinase complex and undergoes normal receptor routing.

In conclusion, our results provide experimental evidence that the defective or inactive heterodimers of EGFR and kinase deficient Neu proteins impair synergistic heteroreceptor signaling, suppress the function of normal EGFR, and abolish the transformed phenotype in living cells. Our experimental model suggests a causal relationship between heterodimeric kinase activities and cell malignancy which may have clinical implications. A recent report has shown that a truncated ecto-domain of c-erbB2 protein produced by alternative RNA processing in human carcinoma cells overexpressing $p_{185}{}^{c-erbB2}$ receptor results in resistance to the growth inhibiting effects of the anti-c-erbB2 monoclonal antibody (Scott et al., Mol. Cell. Biol., 1993, 13, 2247, which is incorporated herein by reference). It is speculated that the direct gene transfer of kinase deficient Neu cDNA into tumor cell lines with co-overexpression of EGFR and Neu/c-erbB2 may relieve the malignant phenotype, as the mutant Neu proteins may suppress the function of either normal EGFR or c-erbB2 receptors by homo- or hetero-receptor interactions.

Example 4

Inhibition of a Naturally Occurring EGFR Oncoprotein by the P185Neu Ectodomain: Implications for Subdomain Contributions to Receptor Assembly Introduction Receptor activation of the erbB family involves both homodimer and heterodimer assembly formation. In many cases, the formation of heterodimers between erbB family members increases ligand-binding affinity and results in the formation of a more active signaling complex which influences cell phenotype. Using p185neu and EGF receptor mutants, the ectodomain alone of these erbB receptors has been shown to be sufficient to allow for a thermodynamically preferred heteromeric physical association and that cytoplasmic contacts in the resultant dimer affect ligand affinity, signaling and phenotype. Biochemical analysis of p185neu and EGFR suggests that the consequences of dimer formation between extracellular domains alone is different from the signaling resultant from endodomain dimer formation. p185neu ectodomain-derived mutants are capable of specific trans-inhibition of EGF receptor signaling in both murine fibroblasts and primarily transformed EGFR-overexpressing human cells. The active receptor complex for Neu Differentiation Factor (NDF/heregulin) appears to be either an erbB2-erbB3 or erbB2-erbB4 heterodimer, suggesting that p185neu/erbB2 functions, in part, as a transregulator of other erbB family receptor kinases.

To further examine receptor subdomains responsible for trans regulatory interactions mediated by the extracellular domain in the erbB family, the interaction between the EGFR and p185neu/c-erbB2 in transformed cells was analyzed. An EGFR oncoprotein commonly observed in human glial neoplasms and other human epithelial malignancies (ΔEGFR or EGFRvIII) results from an in-frame truncation involving exons 2 through 7 (amino acids 6 to 273) in the gene encoding the extracellular region of the molecule resulting in the expression of truncated, constitutively phosphorylated ΔEGFRs of 140–155 kDa. ΔEGF receptors have been observed to exist spontaneously in a dimeric form and mediate constitutive signaling and oncogenic transformation of rodent fibroblasts in a ligand-independent manner, while overexpressed p170 holo-EGFRs are only weakly transforming in the presence of EGF. ΔEGFR oncoproteins confer a dramatic growth advantage in vivo in human glioblastoma cells and in murine fibroblasts.

Recent reports indicate that ΔEGF receptors are present on the cell surface and internalize more slowly than ligand-stimulated holo-EGFRs, which may increase transforming efficiency of ΔEGFR oncoproteins. Other mutations which functionally separate the extracellular domain from the transmembrane and cytoplasmic region of RTK polypeptides have also been observed to lead to spontaneous dimerization and to the acquisition of transforming potential, suggesting that a portion of the extracellular domain imposes a structural constraint on dimer formation which is presumably removed by ligand-binding or mass action. Extracellular deletions observed in ΔEGFRs or avian v-erbB oncogenes presumably facilitate dimer formation by mimicking the conformational changes resulting from ligand-binding. Soluble extracellular domains of the EGFR have been observed to oligomerize and structural alteration in the ectodomain can induce spontaneous oligomerization of extracellular domains, cytoplasmic domains, or both.

The extracellular deletion in ΔEGFR removes the majority of amino acids comprising subdomains I and II of the EGFR, which includes a large portion of the first (more amino-terminal) of two cysteine-rich sequences in the extracellular region of the receptor. Subdomain m, which has been reported to confer ligand-binding properties to the EGFR, is preserved in the ΔEGFR oncoprotein, although ΔEGFRs do not appear to bind ligand in NIH3T3 cells. Coexpression of holo-EGFRs and ΔEGFRs has been observed in human glioblastoma and other tumor samples, suggesting that EGFR/ΔEGFR co-expressing cells may be a close correlate of human disease.

An ectodomain-derived, carboxy-terminal deletion mutant of the p185neu oncogene (T691stop neu), lacking the entire kinase domain and carboxyl-terminal autophosphorylation sites was expressed in human glioblastoma cells coexpressing full-length EGFR and ΔEGFRs to examine whether the p185neu ectodomain could associate with truncated, ectodomain-deleted ΔEGFRs and modulate ΔEGFR-mediated signaling.

Results

Expression of EGFR and p185Neu Mutant Forms in Human Glioblastoma Cells

U87MG human glioblastoma cells express elevated levels ($10^5$ receptors/cell) of endogenous, wild-type EGFR. Three clonal derivatives of parental U87MG human glioblastoma cells were utilized for these studies: U87/T691-1 cells contain T691stop neu in the U87MG background; U87MG.ΔEGFR cells express elevated levels ($10^6$ receptors/cell) of human EGFR proteins in parental U87MG cells; and doubly transfected U87MG.ΔEGFR/T691s cells contain endogenous EGFR, ΔEGFRs, and T691stop mutant neu proteins. Expression levels of EGRFs and truncated neu proteins in U87MG-derived human glioblastoma cells after metabolic labeling were compared. Subclones derived from parental U87MG human glioblastoma cells notable for the expression of ΔEGFR and/or T691stop neu mutant receptors were labeled with $^{35}$S-cysteine for 15 h and cell lysates were immunoprecipitated with either anti-EGFR mAb 528 reactive with both the EGFR and ΔEGFR ectodomains or anti-neu mAb 7.16.4 which recognizes the p185neu ectodomain. Immune complexes were resolved and separated by 8% SDS-PAGE. Protein signals representing EGFR (170 kDa), ΔEGFRs (140–155 kDa), and truncated T691stop neu proteins (115 kDa) were observed. U87MG cells express endogenous full-length EGFR only; U87/T691-1 cells express endogenous EGFR and T691stop neu proteins; U87MG.ΔEGFR cells express endogenous EGFR and transfected ΔEGFRs; and U87MG.ΔEGFR/T691s cells express EGFR, ΔEGFRs, and T691stop neu proteins. All signals were observed after autoradiography (24 h exposure). Immunoprecipitating with mAb 528 (Oncogene Science) reactive with EGFR and ΔEGFR demonstrated all EGFR forms expressed in the U87MG-derived cell lines. EGFRs were identified in U87MG.ΔEGFR and U87MG.ΔEGFR/T691s cells only. Metabolic labeling and immunoprecipitating with mAb 7.16.4 reactive with the p185neu ectodomain allowed for the identification of T691stop mutant neu receptors of 1 15 kDa in U87/T691-1 cells and in U87MG.ΔEGFR/T691s cells. Flow cytometric analysis of U87/T691-1 and U87MG.ΔEGFR/T691s subclones with mAb 7.16.4 confirmed surface localization of T691stop neu proteins. Flow cytometric analysis also confirmed cell surface localization of ΔEGFRs on both U87MG.ΔEGFR and U87MG.ΔEGFR/T691s subclones. U87MG glioblastoma cells contain negligible levels of erbB-2 or erbB-3.

Immunoprecipitation and immunoblotting of EGFRs in U87MG.ΔEGFR cells revealed the presence of endogenous EGFR (170 kDa) and transfected ΔEGFRs running as a doublet species of Mr140 kDa and 155 kDa. U87MG.ΔEGFR cell lysates were immunoprecipitated with either mAb A Δ124 reactive with ΔEGFR only or mAb 528 reactive with the extracellular domain of both EGFR and ΔEGFR. Equal protein amounts, as determined by the Bio-Rad protein assay kit (Bio-Rad Laboratories), were immunoprecipitated and immunocomplexes were separated by SDS/8% PAGE under reducing conditions. Immunoprecipitated EGFRs were detected by immunoblotting with Ab-4, a polyclonal antibody against human EGFR. The A Δ124 antibody precipitated two species of ΔEGFRs of 140–155 kDa. mAb 528 precipitated endogenous EGFR (Mr=170 kDa) as well as ΔEGFRs (140–155 kDa). The two species of ΔEGFRs in U87MG.ΔEGFR cells were more clearly resolved by mAb Δ124. All protein signals were visualized by the enhanced chemiluminescence (ECL) system (Amersham). Scanning densitometry of mAb Δ124-immunoprecipitated ΔEGF receptors revealed that the ratio of 155 kDa to 140 kDa ΔEGFR forms was 2.3 in U87MG.ΔEGFR cells. Additionally, densitometric analysis of mAb 528 immunocomplexes showed that the ratio of ΔEGFRs/EGFR in U87MG.ΔEGFR cells was approximately 10:1. This pattern was also demonstrated for U87MG.ΔEGFR/T691s double transfectants. Scanning densitometry was used to confirm a stoichiometric ratio of ΔEGFR:EGFR of 10:1 by immunoprecipitation of cell lysates using mAb 528 reactive with the extracellular domains of EGFR and ΔEGFR, followed by immunoblotting with a polyclonal antisera reactive with EGFR in both U87MG.ΔEGFR cells and U87MG.ΔEGFR/T691s cells.

T691stop neu ectodomain was demonstrated to efficiently form heterodimers with full-length, wild-type EGFR on the surface of parental U87MG cells and in rodent fibroblasts, using the membrane-impermeable cross-linker DTSSP (3,3'-dithiobis(sulfosuccinimidylpropionate). The p185neu ectodomain inhibited the EGF-induced downregulation of endogenous EGFR in U87MG-derived cells as determined by immunoblotting. Flow cytometric analysis indicated that receptor association occurring at the cell-surface mediates inhibition of EGFR, rather than endocytosis and degradation. In particular, experiments showing the association between endogenous EGFR and truncated neu receptors in vivo and inhibition of EGF-induced downmodulation of EGFR in glioma cells expressing T691stop neu receptors were performed. U87MG parental cells and U87/T691-1 cells (U87MG cells which express T691stop neu) were precipitated with anti-EGFR mAb 528 (Oncogene Science) or anti-neu mAb 7.16.4 after cross-linking with DTSSP (3,3'-dithiobis(sulfosuccinimidylpropionate) (2 mM) (Pierce) with or without EGF treatment (100 ng/ml at 37° C. for 10–15 min). Immunocomplexes were analyzed by SDS/8% PAGE under reducing conditions. EGFR (Mr=170 kDa) was detected by immunoblotting with Ab-4 (Oncogene Science), a polyclonal antibody against human EGFR. Co-precipitated EGFR proteins were detected in U87/T691-1 cells immunoprecipitated with anti-neu mAb 7.16.4. EGF treatment resulted in more efficient downmodulation of EGFR in U87MG cells than in U87/T691-1 cells. These data are in agreement with prior studies performed in rodent fibroblasts. The T691stop neu ectodomain inhibited the EGF-induced phosphorylation of wild-type endogenous EGFR in U87MG-derived cells. ΔEGFR is constitutively phosphorylated in U87MG.ΔEGFR cells, while p170 EGFR is phosphorylated in U87MG parental cells and in U87MG.EGFR cells only upon the addition of EGF. Blotting with an antiphosphotyrosine antibody revealed that the lower molecular weight species (p140) of ΔEGFR is underphosphorylated relative to the p155 species in U87MG.ΔEGFR cells. Ligand-dependent activation of EGFRs in U87MG-derived human glioblastoma cells was determined as follows. Phosphotyrosine content of anti-EGFR immunocomplexes in U87MG cells, U87/T691-1 cells (contain endogenous full-length EGFR and T691stop mutant neu), and U87MG.ΔEGFR cells (contain endogenous EGFR and ΔEGFR) was determined. Equal cell numbers were plated and starved in serum-free media for 24 h after attachment to 10-cm dishes. Cells were treated ±EGF (100 ng/ml at 37° C. for 10–15 min), washed twice with cold PBS and solubilized with PI/RIPA buffer. Lysates of equal protein concentrations as determined by the Bio-Rad assay (Bio-Rad Laboratories) were immunoprecipitated with anti-EGFR mAb 528 and immunocomplexes were analyzed by SDS/8% PAGE under reducing conditions. Phosphorylated EGFRs were detected in parental U87MG and U87MG.ΔEGFR cells, but not U87/T691-1 cells. The phosphorylation of endogenous, full-length EGFR (170 kDa) was EGF-dependent in U87MG cells and in U87MG.ΔEGFR cells. However, the phosphorylation of ΔEGFRs was not dependent on EGF treatment in U87MG.ΔEGFR cells. The blot was stripped and reprobed with the polyclonal anti-EGFR antibody, Ab-4. The presence of all EGFRs was confirmed in the cell types treated as above. EGFR proteins appear as a doublet of 140–155 kDa, with the higher molecular weight species more significantly phosphorylated. All protein signals were visualized by the enhanced chemiluminescence (ECL) system (Amersham).

Modulation of ΔEGFR-mediated Cell Growth and transformation by the T691Stop Neu Mutant Cell proliferation and transforming efficiency of U87MG-derived human glioblastoma cell lines was assessed in vitro and in vivo in order to determine modulation of ΔEGF receptor signaling by ectodomain-derived p185neu mutant proteins. Inhibition of cell growth in full or reduced serum conditions was studied in the following experiments. $2 \times 10^4$ cells of each cell line were plated in 6-well plates and allowed to attach in full-growth media. The next day, the cells were either maintained in full-growth media (10%-FBS) or changed to 2%-FBS serum. Cells were allowed to grow for four days and were then trypsinized and counted. Parental U87MG cells were used for normalization (growth ratio=1.0 for all experiments). The growth of all derived cell lines was expressed as a fraction of the parental cell line for comparison. U87MG.ΔEGFR cells express endogenous EGFR and ΔEGFRs, U87MG.ΔEGFR/T691s cells express EGFR, ΔEGFR, and T691stop neu, and U87/T691-1 cells express endogenous EGFR and T691stop neu proteins. ΔEGFR expression (U87MG.ΔEGFR cells) increased cell proliferation in reduced serum conditions over parental U87MG cells, which is consistent with ligand-independent activation of ΔEGFRs. Expression of T691stop mutant neu proteins inhibited cell growth in reduced serum and, notably, in full-growth media in both EGFR/ΔEGFR- coexpressing glioblastoma cells and in parental U87MG cells containing endogenous EGFR only. Of note, U87MG.ΔEGFR/T691s subclones exhibited decreased cell proliferation than parental U87MG cells lacking EGFRs in both full-growth media and, to a greater degree, in reduced serum conditions.

ΔEGFR did not increase transforming efficiency in vitro in anchorage-independent growth assays over parental U87MG cells. Anchorage-independent growth was studied in the following experiments. 1000–3000 cells of each cell line were seeded in soft agar dishes and cultured for 21–28 day. Colonies were then visualized and counted after staining. U87MG cells are primary transformed human cells containing multiple somatic genetic alterations, including deletions of p16 and in the putative protein tyrosine phosphatase gene, PTEN. Soft agar growth of U87MG.ΔEGFR/T691s cells was reduced 41.3% and 45% compared to parental U87MG and U87MG.ΔEGFR cells, respectively. Inhibition of anchorage-independent growth achieved by T691stop neu proteins was more significant in U87MG parental cells lacking ΔEGFR (mean 75.2% inhibition relative to parental U87MG cells in three independent experiments).

The ΔEGF receptor confers a selective growth advantage in vivo in the U87MG cell background, while many studies have shown that holo-EGFRs are nontransforming in vivo, except under defined conditions in which p185neu receptors are co-expressed. Expression of the T691stop mutant neu ectodomain in U87MG cells has been shown to preferentially inhibit the U87MG oncogenic phenotype when compared to a form of truncated p185neu (N691stop ) which differs from T691stop by containing the protooncogenic transmembrane region. A comparison of tumor growth in athymic mice between U87MG-derived cells lines was made as follows. $10^6$ cells of each cell line were injected intradermally on day 0 and tumor volume was recorded 1–2×/week. U87MG cells were injected on one side and the transfected cell line was injected into the contralateral side of the animal. T691stop neu protein expression abrogated the selective in vivo growth advantage mediated by ΔEGFR in U87MG cells. This result was confirmed by an analysis of three additional U87MG.ΔEGFR/T691s subclones. The U87MG.ΔEGFR/T691s subclone exhibited growth kinetics which are similar to parental U87MG cells, though appeared to be more inhibited than U87MG cells in vivo. Inhibition observed in vivo for all U87MG.ΔEGFR/T691s subclones was directly related to the stoichiometry of T691stop mutant neu expression.

The T691Stop Neu Mutant Forms Heterodimers with ΔEGFR in Vivo

Because of the genetic complexity of U87MG.ΔEGFR transfectants and U87MG.ΔEGFR/T691s doubly transfected subclones, and the multiple homodimeric and heterodimeric complexes migrating at similar molecular weights in gradient SDS-PAGE analysis, the thiocleavable, membrane-impermeable cross-linker DTSSP was employed to examine individual components of putative surface-localized heteromeric complexes. The mAb 528 was utilized to immunoprecipitate all EGFRs (wild-type and ΔEGFRs) which might form heteromers with mutant neu proteins. Co-precipitated ΔEGFR monomers from anti-neu immunocomplexes were deleted by in vivo cross-linking experiments using DTSSP. Cross-linking of U87MG.ΔEGFR/T691s cells and separating immunocomplexes by SDS/6–8% PAGE under reducing conditions revealed evidence of heterodimer formation between T691stop neu proteins and the p140ΔEGFR, p155ΔEGFR, and p170EGFR forms. Most of the T691stop neu mutant receptors associated with the p140ΔEGFR form using these methods, although faint bands identifying heterodimerized p155ΔEGFR and p170EGFR proteins were repeatedly observed. Identification of ΔEGFR proteins on the cell surface of U87MG.ΔEGFR and U87MG.ΔEGFR/T691s double transfectants by flow cytometry supports the observations made with the membrane-impermeable cross-linker. T691stop neu mutant receptors form heterodimers with ΔEGF receptors on the cell surface. Experiments to detect co-precipitated ΔEGFRs from anti-neu immunocomplexes by in vivo cross-linking were performed as follows. 1 mg lysates of U87MG parental cells (lanes 1, 2), U87MG.EGFR cells, and U87MG.EGFR/T691s cells were immunoprecipitated with anti-EGFR mAb 528 or anti-neu mAb 7.16.4 after cross-linking with DTSSP (3,3'-dithiobis (sulfosuccinimidylpropionate) (2 mM) (Pierce) following EGF treatment (37° C. for 15 min). Immunocomplexes were analyzed by SDS/8% PAGE under reducing conditions and the nylon membrane was blotted with Ab-4, a polyclonal Ab against human EGFR. EGFRs were identified in U87MG cells (endogenous EGFR only, Mr=170 kDa); U87MG.ΔEGFR cells (endogenous EGFR and ΔEGFRs, Mr 140–155 kDa); and U87MG.ΔEGFR/T691s cells (endogenous EGFR and ΔEGFRs, Mr 140–155 kDa). Co-precipitated EGFR proteins were detected in U87MG.ΔEGFR/T691s cells immunoprecipitated with anti-neu mAb 7.16.4. In U87MG.ΔEGFR/T691s cells, T691stop neu was found to co-precipitate with the lower molecular weight form of ΔEGFR (140 kDa, strongest signal), the slower migrating form of ΔEGFR (p155), and endogenous holo-EGFR (p170). EGF treatment resulted in better visualization of immunocomplexed monomers but co-precipitated EGFRs could be identified in anti-neu immunocomplexes from U87MG-derived cell lines without EGF treatment.

Phosphotyrosine content of immunoprecipitated EGFRs in U87MG.ΔEGFR/T691s cells was determined using the blot described above. The blot was stripped and reprobed with the antiphosphotyrosine antibody, mAb PY-20 (Santa Cruz Biotechnology, Santa Cruz, Calif.). EGFR proteins detected in anti-neu immunocomplexes had negligible phosphotyrosine content after EGF treatment in U87MG.ΔEGFR/T691s cells compared to anti-EGFR immunocomplexes in U87MG parental cells, and in U87MG.ΔEGFR and U87MG.ΔEGFR/T691s cells. The phosphotyrosine content of anti-EGFR immunocomplexes in U87MG.ΔEGFR and U87MG.EGFR/T691s cells was not appreciably different at these protein lysate concentrations. Blotting with an antiphosphotyrosine antibody confirmed that both ΔEGFR species associated with T691stop neu are underphosphorylated. Negligible phosphotyrosine content for EGFR monomers immunocomplexed to T691stop neu receptors was consistently demonstrated in all experiments. EGF has been observed to increase the efficiency of heterodimer formation between p170EGFR and the neu ectodomain, although this association is ligand-independent. EGF minimally increased the formation of EGFR-p185neu ectodomain immunocomplexes, suggesting that EGF may stabilize heteromeric formation, if not EGFR homodimeric formation.

Reduction of Phosphotyrosine Content of EGFR Monomers in Vivo by T691Stop Neu Coexpression The phosphotyrosine content for ΔEGFR monomers immunocomplexed to T691stop neu receptors was negligible in all experiments. Results also revealed that the lower molecular weight form of ΔEGFR (140 kDa) was relatively underphosphorylated as compared to the p155ΔEGFR form in both U87MG.ΔEGFR cells and U87MG.ΔEGFR/T691s double transfectants.

Differences in the phosphotyrosine content of ΔEGFR monomers between U87MG.ΔEGFR cells and U87MG.ΔEGFR/T691s cells were not observed in immunoprecipitations of larger cell lysates using mAb 528, which reacts with all EGFR forms, for in vivo cross-linking experiments. Therefore, in order to specifically examine the phosphotyrosine content in vivo of ΔEGFRs in T691stop neu-expressing cells, an antibody reactive with the ΔEGFR only was used to precipitate ΔEGFRs from cell lysates containing reduced protein concentrations from those required to detect heterodimeric complexes. Phosphotyrosine content of ΔEGFRs in vivo in U87MG.ΔEGFR cells with or without T691stop mutant neu co-expression was determined as follows. Lysates (200 μg) of U87MG.ΔEGFR cells and U87MG.ΔEGFR/T691s cells were immunoprecipitated with mAb Δ124 reactive with ΔEGFR only and blotted with either anti-phosphotyrosine mAb PY-20 or the anti-EGFR polyclonal antibody Ab-4. Blotting with PY-20 after immunoprecipitating with mAb Δ124 reactive with ΔEGFR only revealed several phosphoproteins in U87MG.ΔEGFR and U87MG.ΔEGFR/T691s cells. The slower migrating form of ΔEGFR (155 kDa) was detected while the faster migrating form of ΔEGFR (140 kDa) was not detected by the PY-20 antibody, indicating relatively lower phosphotyrosine content than p155 kDa. After stripping the membrane and reprobing with Ab-4 reactive with all EGFRs, both ΔEGFR forms were visualized in both U87MG.ΔEGFR and U87MG.ΔEGFR/T691s double transfectants. Scanning densitometric analysis of the phosphorylation content of immunoprecipitated p155ΔEGFR monomers in these cell lines revealed a decrease of 33.7% in U87MG.ΔEGFR/T691s cells when compared to U87MG.ΔEGFR cells, under conditions of full-growth. Observed constitutive differences in ΔEGFR phosphotyrosine content could therefore not be overcome by serum-containing factors. The ratio of PTyr/ΔEGFRs in U87MG.ΔEGFR cells was 1.57; this ratio in U87MG.ΔEGFR/T691s cells was found to be 1.04, as determined by scanning densitometry. This difference was observed in two additional experiments.

The phosphotyrosine content in living cells of total immunoprecipitated ΔEGFR monomers, not only ΔEGFR monomers immunocomplexed to T691stop neu proteins, was analyzed. In addition to the finding that ΔEGFRs immunocomplexed to T691stop neu mutant receptors have negligible phosphotyrosine content, these data indicate that T691stop neu surface expression alone is sufficient to reduce ΔEGFR monomeric phosphotyrosine content in trans. In T691stop neu-containing cells, the observed 33.7% reduction in phosphotyrosine content of immunoprecipitated ΔEGFR monomers may diminish signaling from the activated ΔEGF receptor complex, since the signaling complex may be a higher order multimer and ΔEGFR has been reported to have a lower stoichiometry of phosphotyrosine content than EGF-stimulated wild-type EGFR. Substrate binding and/or catalytic activity of the ΔEGFR receptor kinase could be altered by a reduction of monomeric ΔEGFR phosphotyrosine content. The lower level of constitutive phosphotyrosine content of ΔEGFR relative to ligand-stimulated wild-type EGFR may account for the disabling effect on in vivo growth behavior of individual point mutations in terminal autophosphorylation sites of ΔEGFR. Hetero-oligomers formed by the association between ΔEGFR dimers and T691stop neu dimers may be one mechanism for the reduction of ΔEGFR phosphotyrosine content and the phenotypic inhibition resulting from T691stop neu expression and surface localization.

Reduction of in Vitro Kinase Activity of ΔEGFR by T691Stop Neu Expression

Since a reduction of monomeric ΔEGFR phosphotyrosine content was observed in cells expressing T691stop neu mutant receptors, whether the catalytic activity of the EGFR receptor kinase could be altered by T691stop neu protein expression was investigated. Using conditions identical to those which confirmed the presence of ΔEGFRs in cross-linked T691stop neu-associated heterodimers, experiments studying the reduction of EGFR in vitro kinase activity by T691stop neu expression were performed. 200 μg of lysates were obtained from U87MG.ΔEGFR and U87MG.ΔEGFR/T691s cells with and without pretreatment with the membrane-impermeable cross-linker DTSSP (2 mM). Anti-EGFR (mAb Δ124) immune complexes from these cells were suspended in 50 μl of kinase reaction buffer containing 0.2 mCi[$^{32}$P]-γ-ATP at room temperature for 30 min. Protein samples were separated by 10% SDS-PAGE and analyzed by autoradiography. Anti-EGFR immune complexes were shown o have increased in vitro kinase activity in U87MG.ΔEGFR cells pretreated with a membrane-impermeable cross-linker (DTSSP), but not in doubly transfected cells expressing T691stop neu mutant receptors. T691stop neu expression resulted in a striking inhibition of the trans-phosphorylation of the slower migrating form (155 kDa) of ΔEGFR, due to heterodimer formation confirmed by using DTSSP). These results were confirmed on three independent occasions. Since the 155 kDa ΔEGFR is in higher abundance in both U87MG.ΔEGFR and U87MG.ΔEGFR/T691s cells, the T691stop neu-mediated reduction of catalytic activity of the ΔEGF receptor kinase may explain the phenotypic inhibition observed in doubly transfected human glioblastoma cells. No significant differences were observed in the phosphorylation of the p140ΔEGFR form in these in vitro experiments; however, since this species was phosphorylated in vitro, a fraction may be phosphorylated in vivo. Inhibition of ΔEGF receptor catalytic activity was consistently observed for receptor trans-phosphorylation. At the lower protein concentrations used in in vitro kinase experiments, there was minimal phosphorylation of the exogenous Histone III substrate in all anti-EGFR immune complexes.

The phenotypic inhibition of ΔEGFR signaling mediated by T691stop neu mutant receptors in human glioblastoma cells thus appears to result from: (1) heterodimer formation between T691stop neu proteins and both forms of ΔEGFR, although increased heterodimer formation with p140ΔEGFR was observed; (2) trans-inhibition of 155ΔEGFR monomeric phosphotyrosine content in vivo by T691stop neu expression; and (3) inhibition of trans-phosphorylation of the p155ΔEGFR kinase as a consequence of T691stop neu expression and heterodimer formation.

Discussion

U87MG cells in which constitutively active ΔEGF receptors are coexpressed with endogenous EGFR represent a close approximation of a particularly aggressive subset of human glioblastomas, those tumors in which p16 deletion, allelic loss on chromosome 10q, and EGFR activation occur, while p53 is nonmutated. U87MG-derived human glioblastoma cells expressing endogenous EGFR, elevated amounts of ΔEGFR oncoproteins, and T691stop kinase-deficient neu mutant receptors (U87MG.ΔEGFR/T691s doubly transfected subclones) were inhibited in all in vitro and in vivo assays more than parental U87MG cells. This represented a significant reduction in the phenotype observed with expression of ΔEGFR oncoproteins alone in the U87MG background (U87MG.ΔEGFR cells), particularly in vivo. Given that wild-type EGFR overexpression alone is non-oncogenic in vivo, the observed formation of ΔEGFR-neu ectodomain heterodimers, and the ratio of ΔEGFR:EGFR proteins in these cells, it appears that the observed growth inhibition conferred by T691stop neu and exhibited by U87MG.ΔEGFR/T691s cells was mediated by disabling signaling through ΔEGF receptors rather than endogenous p170 EGFRs.

It is possible that T691stop neu mutant receptors disable a ΔEGFR-EGFR heterodimeric complex, although the stoichiometric ratio of ΔEGFR:EGFR is approximately 10:1 in U87MG.ΔEGFR cells and in U87MG.EGFR/T691s cells. Unlike endogenous wild-type EGFR,ΔEGF receptor dimer formation and autophosphorylation in glioma cells occur independently of ligand and ΔEGFR-expressing NIH3T3 cells exhibit ligand-independent growth and transforming properties, suggesting that oncogenic signaling results from constitutively phosphorylated ΔEGFR dimers. Others have not identified EGFR-ΔEGFR heterodimers in U87MG.ΔEGFR cells. Additionally, tyrosine phosphorylation of kinase-deficient mutants of ΔEGFR expressed in U87MG cells cannot be restored by activating wild-type EGFR with ligand treatment, suggesting a lack of substantial trans-phosphorylation between EGFR and ΔEGFRs. Given the thermodynamic preference of p185neu/erbB2 proteins to heterodimerize with EGFR and other erbB receptors, ΔEGFRs may form dimers with p185neu ectodomain-derived proteins more readily than with holo-EGFRs.

T691stop inhibits the phosphorylation of p170EGFR in U87MG cells, and EGFR and ΔEGFR monomers immunocomplexed to T691stop neu proteins have a negligible phosphotyrosine content. The demonstration of association between T691stop and the ΔEGFR does not necessarily indicate a preferential association over p170 EGFR because ΔEGFR and EGFR are not expressed at comparable levels in these cells. Flow cytometric analysis of all EGFRs in U87MG.ΔEGFR and U87MG.ΔEGFR/T691s-expressing subclones indicated that expression of the p185neu ectodomain did not alter the total EGFR, wild-type EGFR, or ΔEGFR cell-surface populations either in U87MG cells containing endogenous EGFR only or in U87MG.ΔEGFR transfectants containing EGFR and ΔEGFR. This is consistent with the observation that p185neu ectodomains disable EGFR signaling through the formation of defective heteromeric or oligomeric receptor assemblies located on the cell surface, rather than by inducing ΔEGF receptor internalization and downmodulation.

Autophosphorylation of tyrosine residues on EGF receptors activates binding sites for signaling molecules and may also regulate the catalytic activity of the EGF receptor. The constitutive phosphotyrosine content of ΔEGFR monomers in vivo and the kinase activity of ΔEGFR in vitro is reduced in trans as a consequence of T691stop neu expression. The phenotypic inhibition observed in vitro and in vivo in U87MG cells coexpressing ΔEGFRs and T691stop neu proteins (U87MG.ΔEGFR/T691s cells) relative to ΔEGFRs alone (U87MG.ΔEGFR cells) could be due in part to reduced binding sites on EGFRs for signaling molecules as a result of forming heterodimers with T691stop neu. Additionally, kinase activity for trans-phosphorylation of the ΔEGF receptor or other substrate(s) may be also be reduced by a conformational change induced by associating with the T691stop neu mutant receptor. The data support the argument that a diminution of kinase activity for receptor trans-phosphorylation contributes to a reduction in transformation. In vitro kinase activity for an exogenous Histone substrate was observed to be much lower than for receptor trans-phosphorylation and was not appreciably altered by T691stop neu expression. The in vitro kinase activity of ΔEGFR for exogenous substrate is only minimally altered by substitutions of the carboxyl terminal autophosphorylation sites; the reduction of phosphotyrosine content in vivo as a consequence of carboxyl terminal point mutations in ΔEGFR appeared to more reliably correlate with phenotypic inhibition. The level of inhibition achieved in vivo by the T691stop neu mutant expressed in U87MG.ΔEGFR cells was similar to that exhibited by a point mutant of the ATP-binding site in ΔEGFR or by a ΔEGFR mutant with substitution of tyrosines 1068, 1148, and 1173.

Studies using trans-dominant p185neu mutants have indicated that the ectodomains of p185neu and EGFR are sufficient for physical association, and that EGFR signaling can be modulated with these kinase-negative p185neu mutants. Receptor interactions in the cytoplasmic domain determine productive signaling for both p185neu and EGF receptors. In the absence of crystallographic data on the extracellular regions of p185neu and EGFR, the structural features of ectodomain interactions between these receptors are undefined. ΔEGF receptors have been observed to exist in a dimerized form in the absence of ligand. Soluble extracellular regions of the EGFR have been observed to oligomerize in response to EGF after cross-linking, although proteolytic fragments derived from subdomain III alone did not oligomerize, suggesting that other subdomains contribute to dimer formation. Subdomain III has been reported to confer ligand-binding properties to EGFR. Activated avian erbB oncogenes form homodimers in the absence of ligand with deletions of the entire extracellular region other than a portion of subdomain IV (second cysteine-rich domain). However, the physiologic significance of this observed homodimer formation was unclear since this did not correlate with tissue-specific transforming properties of these mutants.

Physical association can occur between the p185neu and EGFR extracellular regions in transformed cells, despite a deletion which includes most of two independent subdomains (I, II) in the extracellular region of the EGF receptor. Extracellular mutants of p185neu deleted of either subdomain I or II still retain the ability to form heterodimers with full-length EGFR, confirming that these sequences are not critical for p185neu/EGFR heteromeric physical associations. The phenotypic inhibition of EGFR oncoproteins by T691stop neu proteins supports the argument that a physical association primarily governed by subdomains III and IV is sufficient to modulate signaling. Based on an analysis of the transforming efficiency of fibroblasts expressing wild-type human EGFR and extracellular subdomain deletion mutants of p185neu, subdomain III in p185neu appears to be the least relevant extracellular subdomain for the formation of a transforming p185neu/EGFR heterodimeric signaling complex, suggesting that subdomain IV-mediated interactions may be most important for the initiation and/or stabilization of homodimeric and heterodimeric receptor complexes.

Each of the two extracellular cysteine-rich domains in subdomain II and IV of p185neu and EGFR may possess a unique fold known as the "EGF fold" or "cysteine knot". The motif is characterized by a repeat of six cysteine residues and by at least two intrachain disulfide bonds. Although a similar motif has been observed in other proteins, its presence is highly conserved in cytokines and transmembrane receptors, including the structurally resolved tumor necrosis factor (TNF) receptor. Several tyrosine kinase receptors have been shown to contain these cysteine-rich domains and it is presumed that they adopt similar conformations to that of the TNF receptor. Tumor necrosis factor (TNF) receptors have been observed as dimers in crystal structures of the uncomplexed form. In this form, the last extracellular cysteine-rich domain forms the major dimeric contacts. In these studies, the membrane proximal domain is disordered perhaps due to the lack of the transmembrane region that holds this domain in a stable state. Thus, it is hypothesized that in the whole receptor, the last cysteine-rich domain just amino-terminal to the transmembrane sequence might be stabilized by the transmembrane sequence and possibly involved in the formation of functional dimers. A high degree of sequence homology between the second cysteine-rich domain (subdomain IV) of p185neu and EGFR and the cysteine knot fold in the TNF receptor has been identified. A simple comparison of sequences in the transmembrane proximal domains of the TNF and p185neu receptors shows at least four of six cysteines are conserved.

Regulation by trans-receptor interactions has been observed for all erbB family members, many of which exhibit altered expression or regulation in human epithelial malignancies. The physiologic tendency of this receptor family to form heteromeric associations suggests that targeting human erbB oncoproteins with structures or pharmaceuticals which mimic certain subdomains in the p185neu ectodomain might be achievable in certain human malignancies. Alternatively, the p185neu ectodomain cDNA could be delivered to erbB receptor-positive tumor cells in a gene therapy approach to human neoplasia. ΔEGFR oncoproteins are differentially expressed in many human epithelial neoplasms and may represent a tumor-specific target, however, these receptors are not regulated by ligand binding, are constitutively phosphorylated, and internalize poorly. These features may limit efforts to inhibit signaling from ΔEGF receptors in human tumors. The preferred thermodynamic tendency for erbB heterodimer formation in the absence of ligand suggests that targeting erbB oncoproteins with the p185neu ectodomain, novel pharmaceuticals, or peptide mimetics relevant to dimer formation would be more effective in achieving growth inhibition than inhibiting ligand-induced activation with monoclonal antibodies or ligand-binding antagonists.

Materials And Methods
Vector Construction

The deletion mutant T691stop neu was derived from the rat oncogenic neu cDNA, pSV2Tneu, containing a single point mutation in the transmembrane region. Site-directed mutagenesis was used to introduce a stop codon at the Thr-691 position in the endodomain. This cytoplasmic-deleted form of p185neu, lacking the kinase catalytic domain and the carboxyl terminal autophosphorylation sites, was then inserted into a mammalian expression vector. A fragment containing the hygromicin$^r$ gene from pHYG was subcloned into APtag-1, an alkaline phosphatase (AP) expression vector under control of the Maloney Leukemia Virus promoter and LTR (MuLVLTR). The AP gene was then replaced by the mutant T691stop neu cDNA. Thus, T691stop was expressed in the pMuLVLTR/T691stop/Hyg$^r$ expression vector.

Maintenance of Cells and Development of Stably Transfected Cell Lines

The U87MG parental human glioblastoma cell line and the previously reported U87MG.ΔEGFR human glioblastoma subclone containing human ΔEGF receptors (Nishikawa et al., 1994) were obtained from Dr. Webster Cavenee (Ludwig Cancer Institute, San Diego, Calif.). For stable cell transfections, ten micrograms of the pMuLVLTR/T691stop/Hyg$^r$ construct was transfected into U87MG.ΔEGFR cells via the lipofectamine reagent (GIBCO/BRL, Gaithersberg, Md.) under conditions determined by transfections using the pCMV-β (bacterial β-galactosidase) (Clontech) reporter construct. Optimal transfection efficiency was determined by chemiluminescence as detected by a luminometer (Tropix). All cells were cultured in Dulbecco's modified Eagle's medium (DMEM, Bio-Whittaker, Walkersville, Md.) with 10% fetal bovine serum (Hyclone, Ogden, Utah), 100U penicillin, 50 μg/ml streptomycin, and 2 mM L-glutamine (GIBCO BRL). Cultured cells were maintained at 37° C. in 95% air/5% $CO_2$. U87MG.ΔEGFR cells were supplemented with 0.4 mg/ml G418 (Geneticin, GIBCO BRL) for maintenance of ΔEGFR transgene expression.

For the development of U87MG-derived double transfectants expressing ΔEGFR and T691stop neu proteins, the media was supplemented with both G418 sulfate and hygromicin B. After 2–3 weeks in selection media containing 70 ug/ml hygromicin B (Boehringer Manheim) and 0.4 mg/ml G418 sulfate (Geneticin, GIBCO BRL), established U87MG.ΔEGFR clones expressing T691stop neu (designated U87MG.ΔEGFR/T691 cells) were isolated and screened by flow cytometric analysis using mAb 7.16.4 against the neu ectodomain. The medium for stably transfected subclones was supplemented with 0.4 mg/ml G418 sulfate and 35–70 ug/ml hygromicin B for maintenance of transgene expression. Stably transfected cell lines were periodically checked by flow cytometric analysis with mAb 7.16.4 to document stable levels of T691stop neu transgene expression.

Metabolic Labeling of Cells Followed by Immunoprecipitation

Subconfluent cells ($1\times10^6$) are seeded overnight onto 10-cm dishes in fill growth medium (10% FBS-DMEM). The following day, cells are starved in cysteine-free DMEM for one hour then pulsed with $^{35}$S-cysteine (50 μCi/ml) (Amersham) for 15 h in 3% dialyzed FBS/cysteine-free DMEM. Lysates are harvested after two washes in PBS using a PI/RIPA buffer. Immunoprecipitations are carried out on ice for 60 minutes and complexes are separated by binding to protein A-sepaharose prior to separation by 8% SDS-PAGE, drying, and exposure to film. Monoclonal antibody 7.16.4 against the p185neu ectodomain is described in U.S. Pat. No. 5,677,171. Monoclonal antibody 528 against the extracellular domains of both EGFR and EGFR was obtained from Oncogene Science. 5 μg of antibody was utilized for immunoprecipitating proteins from lysates recovered from 10-cm dishes.

Cross-linking Studies, Immunoprecipitations, and Western Blotting

Equal cell numbers were plated and cultured overnight in 10-cm dishes. Cells were starved for 24 h in serum-free media and were treated with EGF (100 ng/ml at 37° C. for 10–15 min)and then washed twice with cold phosphate-buffered saline (PBS). For cross-linking, PBS containing 2 mM DTSSP (3,3'-dithiobis(sulfosuccinimidylpropionate) (Pierce) was then added and cells were incubated at 23° C. for 30 min, with occasional rocking of the plates. The cross-linking reaction was quenched with buffer containing 10 mM Tris HCl, 0.9% NaCl, and 0.1 M glycine. Cells were then washed twice with cold PBS and solubilized with PI/RIPA buffer. Cell lysates were subjected to immunoprecipitation with either anti-neu mAb 7.16.4, anti-EGFR mAb 528, or anti-ΔEGFR mAb A124. The immunocomplexes of neu proteins or EGFR proteins were then solubilized and separated by SDS-PAGE gels (6–8%), and transferred onto nitrocellulose before immunoblotting with either the polyclonal anti-EGFR antibody, Ab-4 (Oncogene Science) or the anti-phosphotyrosine mAb PY-20 (Santa Cruz Biotechnology, Santa Cruz, Calif.)

In Vitro Kinase Assay

Cells were plated in 100 mm culture dishes and the next day were washed twice in ice cold PBS and lysed in 1 ml of lysis buffer (50 mM Hepes, pH 7.5, 150 mM NaCl, 3% Brij-35, 2 mM EDTA, 0.02 mg/ml Aprotinin, 10% glycerol, 1.5 mM $MgCl_2$). Cell lysates were centrifuged at 20,000 g for 15 min. Protein concentrations of cell lysates were measured with the Dc Protein Assay (Bio-Rad). 40 microliters of 50% (vol/vol) protein A-sepharose were used to collect the immune complexes, which were then washed three times with wash buffer (50 mM Hepes, 150 mM NACl 0.1% Brij-35, 2 mM EDTA, 0.01 mg/ml Aprotinin, 0.03 mM $Na_3Vo_4$). The pellets were suspended in 20 microliters of 20 mM HEPES (pH 7.4, 5mM $MnCl_2$, 0.1% Brij-35, 0.03 mM $Na_3Vo_4$, 0.02 mg/ml Aprotinin) containing 5 uCi of $^{32}P$-γ-ATP, and incubated at room temperature for 30 min. The reaction were terminated by the addition of 3× electrophoresis sample buffer containing 2 mM ATP. After incubation at 100° C. for 3 min, samples were then analysed by SDS-PAGE.

In Vitro and in Vivo Tumorigenicity Assays

Cell growth in full or reduced serum conditions was assessed as follows: $2 \times 10^4$ cells of each cell line were plated in 6-well plates and allowed to attach in full-growth media. The next day, the cells were either maintained in full-growth media (10%-FBS or changed to 2%-FBS serum. Cells were allowed to grow for four days and were then trypsinized and counted.

Anchorage-independent growth was determined by assessing the colony-forming efficiency of cells suspended in soft agar. $1-3 \times 10^3$ cells were suspended in a 1 ml top layer (0.18% agarose/10% FBS-DMEM) in 6 cm culture dishes containing a 3 ml cell-free feeder layer consisting of 0.25% agarose in DMEM supplemented with 10% FBS and 20 mMHepes (pH 7.5). Colonies (>0.3 mm) were visualized and counted on day 21–28 for all cell lines after staining with p-iodonitrotetrazolium violet (1 mg/ml). Each cell line was examined in triplicate for three separate experiments.

6–8 week-old NCr homozygous nude mice were purchased from the National Cancer Institute. Cells ($1 \times 10^6$) were suspended in 0.1 ml of PBS and injected intradermally into the mid-dorsum of each animal. Parental U87MG cells were injected on one side of individual animals and stably transfected cell lines were injected on the contralateral side to make direct comparisons of growth within each animal. PBS alone was also injected into each animal as an additional control. Animals were maintained in accordance with the guidelines of the Committee on Animals of the University of Pennsylvania and those prepared by the Commitee on Care and Use of Laboratory Animals of the Institute of Laboratory Animal Resource. Tumor growth is monitored twice weekly for 10–12 weeks. Tumor size was calculated by measuring tumor volume (length×width×thickness).

Antibodies

Monoclonal antibody (mAb) 7.16.4 reactive with the ectodomain of p185neu has been described previously. The antiphosphotyrosine antibody, mAb PY-20, was obtained from Santa Cruz Biotechnology (Santa Cruz, Calif.). mAb 528 (Ab-1) reactive with the extracellular region of EGFR and ΔEGFR was purchased from Oncogene Science (Uniondale, N.Y.). mAb Δ124 reactive with the ΔEGFR only was obtained from Dr. Webster K. Cavenee, Ludwig Cancer Institute, San Diego, Calif. The polyclonal antibody Ab-4, reactive with the EGFR and utilized for immunoblotting, was obtained from Oncogene Science (Uniondale, N.Y.).

Example 5

Conversion of a Radioresistant Phenotype to a More Sensitive one by Disabling erbB Receptor Signaling in Human Cancer Cells Introduction The molecular parameters which determine how a cell becomes more or less sensitive to DNA damage induced by radiation or chemotherapeutic agents are poorly understood. Status of cell cycle checkpoint signaling pathways has been argued to be an important determinant of the response to DNA damage and mutations in checkpoint components are prevalent in human cancers. A recently introduced paradigm suggests that tumor cells exhibit growth arrest or apoptosis in response to cytotoxic therapies depending on the functional state of checkpoint pathways, and that radiation-induced apoptosis may result from impaired growth arrest pathways. Similarly, in other systems using nontransformed cells, incomplete mechanisms of DNA repair, occurring during checkpoint phase delay, increase the tendency to apoptosis.

Human glioblastomas exhibit many genetic alterations, including amplification and/or mutation of the gene encoding the Epidermal Growth Factor Receptor (EGFR), in some casing resulting in expression of a constitutively activated EGF receptor kinase.

Expression of a trans-receptor inhibitor of the EGFR, derived from the ectodomain of the p185neu oncogene (T691stop neu), forms heterodimers with both full-length EGFR and a constitutively activated extracellular-deleted mutant EGFR form (ΔEGFR) commonly observed in human glial tumors, particularly those of higher pathologic grade. Cell growth and transformation of EGFR-positive or EGFR/ΔEGFR-coexpressing human glioma cells is inhibited by kinase-deficient deletion mutants of p185neu. The surface-localized T691stop neu mutant/EGFR heterodimeric receptor complex has decreased affinity for the EGF ligand, impaired internalization kinetics, reduced phosphotyrosine content, and diminished enzymatic kinase activity relative to full-length EGFR and EGFR homodimeric complexes.

The specific pathways mediating oncogenic transformation in EGFR-positive transformed human cells have not been completely characterized. Naturally occurring ΔEGFR oncoproteins may increase constitutive activity of a Grb2/Shc/Ras pathway and signaling through phosphatidyl inositol-3 (PI-3) kinases, presumably by binding to distinct adaptor proteins. Particular mitogen-activated protein (MAP) kinases, such as those of the c-jun amino terminal kinase (JNK) family, may be constitutively activated by ligand-independent oncogenic ΔEGF receptors. Though holo-EGFRs have been found to be weakly transforming only in a ligand-dependent manner at high levels of receptor expression in fibroblasts, many human tumors exhibit elevated levels of EGFR and this may contribute to unregulated kinase activity in transformed cells.

Experiments were designed to address whether specific inhibition of signaling through the overexpressed EGFR in radioresistant human glioma cells would alter the physiologic response of these cells to the induction of genomic damage. Gamma-irradiation combined with erbB receptor inhibition resulted in a greater degree of radiation-induced growth arrest and apoptosis in cells normally resistant to ionizing radiation. Increased apoptosis occurred in transformed human glioma cells containing either a wild-type or mutated p53 protein, and suggested that both p53-dependent and p53-independent mechanisms mediated this physiologic outcome. Pathways distal to the specific inhibitory interaction between the T691stop mutant neu protein and the EGF receptor determine tumor responsiveness to genomic damage and these pathways can be modulated by proximal receptor associations. Specific inhibitory pathways initiated at the level of the cell membrane and associated with growth arrest and/or apoptosis may modulate subsequent checkpoint outcomes in response to DNA damage. These results have implication for the design of receptor-specific agents capable of sensitizing cells to cytotoxic therapies and suggest that erbB receptor-specific inhibition combined with cytotoxic treatments may improve the response to anticancer agents.

Materials and Methods

Vector Construction

The derivation of the T691stop neu mutant receptor construct is detailed above.

Maintenance of Cells and Development of Stably Transfected Cell Lines

The U87MG human glioblastoma cell line was obtained from Dr. Webster Cavenee (Ludwig Cancer Institute, San Diego, Calif.). U373MG human glioma cells, originally isolated from a human anaplastic astrocytoma, were obtained through the American Type Tissue Collection (ATCC) (Rockville, Md.).

Flow Cytometric Analysis of Cell Cycle Distribution

Cells were stained for flow cytometry by sequential treatment with 0.003% trypsin solution, followed by 0.05% trypsin inhibitor, 0.01% RNase A solution, and then 0.0416% propidium iodide (PI) and 5 mM spermine tetrachloride solution. Each treatment was performed for 10 minutes with continuous shaking at room temperature. All reagents were ordered from Sigma. Cell cycle analysis was performed within 2 h of staining on a Becton-Dickinson FACScan flow cytometer. Ten thousand events were collected for each sample and the data analyzed using the ModFIT cell cycle analysis program (Becton-Dickinson, version 2.0).

Nuclei Staining and Morphologic Analysis of Apoptosis

Cells were plated onto coverslips for at least 12 hours prior to irradiation. Irradiation was performed in conditions identical to the Colony Formation Assays. Coverslips were then washed twice with PBS at the indicated times, and fixed in 50:50 mix of ice-cold methanol/acetone for ten minutes. Coverslips were subsequently stained with 4',6-Diamidino-2-phenylindole dihydrochloride hydrate (DAPI) (Sigma, St. Louis, Mo.) at a concentration of 0.1 µg/ml in PBS. Interobserver consistency in apoptosis counts were confirmed with terminal deoxynucleotidyl transferase-mediated dUTP nick end labeling (TUNEL)-staining and by three independent observers.

Cell counts were performed within 30 minutes of staining and photographs were taken on a Zeiss Axioplan epiflouorescence microscope. At least three independent fields of 100 cells were counted for each sample.

Colony Formation Assay

Cell survival following irradiation was assessed by the colony formation assay. The number of cells to be plated was calculated to form 20 to 200 colonies per dish at each radiation dose, and plated into 10 cm culture dishes (Fisher Scientific, Pittsburgh, Pa.). Cells were irradiated using a J. L. Shepherd model 30 Mark I Cesium-137 irradiator delivering 12.8 Gy/min with the cells on a rotating platform to ensure uniform irradiation. Cells were incubated after irradiation at 37° C. with 5% $CO_2$ for 7–10 days and then stained with crystal violet. Colonies containing more than 50 cells were counted under a dissecting microscope. The surviving fraction is the ratio of the number of colonies formed to the number of cells plated, and was corrected for plating efficiency. At least three different cell concentrations were used for each radiation dose.

Western Blotting

For each time point, $10^5$ cells per 6 cm plate were harvested by lysis in 400 µl of sample buffer (10% glycerol, 2% SDS, 100 mM DTT, 50 mM Tris, pH 6.8). 30 µl of each lysate was loaded per lane and separated by electrophoresis on a 15% SDS-polyacrylamide gel prior to overnight transfer to a nitrocellulose membrane (Bio-Rad, Hercules, Calif.). Membranes were probed with mouse anti-human p53 monoclonal antibody (NeoMarkers, Femont, Calif.), followed by goat anti-mouse secondary antibody coupled to horseradish peroxidase (Amersham, Arlington Heights, Ill.). In order to reduce background antibody binding, incubation with secondary antibody in 2.5% powdered milk in PBS was performed. Detection was performed by chemiluminescence (ECL, Amersham, Arlington Heights, Ill.). Relative levels of p53 expression were determined by scanning the blots using a scanning densitometer (Molecular Dynamics).

Antibodies

The monoclonal antibody 7.16.4 reactive against the p185neu ectodomain is described above. Anti-ERK and anti-JNK antibodies were obtained from Santa Cruz Biotechnology (Santa Cruz, Calif.). Polyclonal antibodies reactive with p53 and p21 were obtained from NeoMarkers (Fremont, Calif.). Antibodies reactive with bcl-2, bax, and bcl-$x_L$ were obtained from Oncogene Science (Uniondale, N.Y.).

Results

Cell cycle Distribution of Cycling Human Glioblastoma Cells Treated with Gamma-irradiation: Effects of Disabling erbB Signaling on Growth Arrest For both U87MG and U87/T691 cells, prolonged serum starvation alone (72–100 h) led to increased accumulation of cells in G0/G1, with modest reductions in both the S and G2/M populations. U87/T691 cells exhibited a higher G0/G1 fraction than parental U87MG cells either in the presence of serum or after prolonged serum deprivation, indicating that the relatively increased growth arrest induced by expression of the T691stop neu mutant receptor was not overcome by growth in full serum.

Figure 1B:
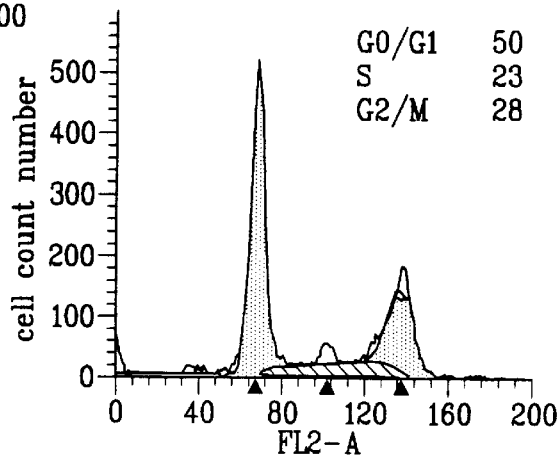
Figure 1C:
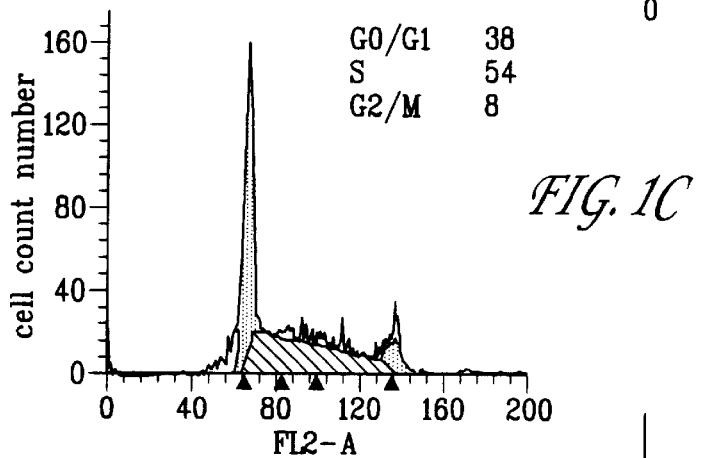
Figure 1D:
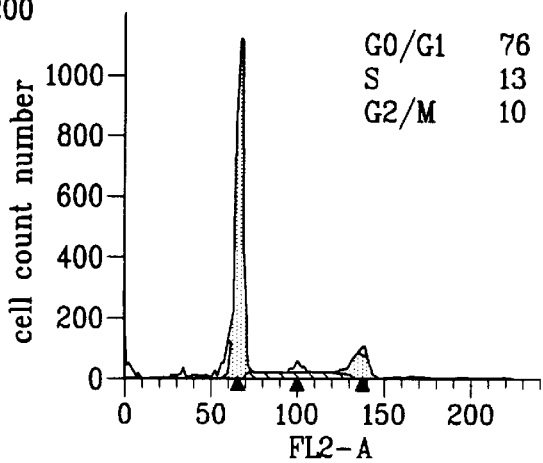

Induction of growth arrest by exposure of asynchronously cycling transformed human glial cell populations to gamma-irradiation was greater than that induced by prolonged serum deprivation alone. In both U87MG and U87/T691 cells, irradiation of cells grown under full serum growth conditions caused robust increases in G0/G1 and G2/M, and a decrease in the percentage of cells in S phase, as determined by flow cytometric staining for DNA content (FIGS. 1B and 1D). Reduction of the S phase fraction and accumulation of cells in G2 is characteristic of cells sustaining DNA damage. The data in FIGS. 1A, 1B, 1C and 1D depict a representative experiment of cells analyzed 72 h after gamma-irradiation. Earlier time points indicated similar trends, but analysis 72 h after irradiation was chosen to be consistent with subsequent experiments. An analysis of three independent experiments revealed the following changes in cell cycle distribution (mean percent of cells±SEM;±radiation treatment [RT]):

1.) U87MG parental cells:
G0/G1:26±2.8,+RT 51.5±2.1;
S: 66±4.2,+RT 21±2.8;
G2/M: 8±1.4,+RT 28.5±0.7;
2.) U87/T691 cells:
G0/G1: 34.5±4.9,+RT 71±7.1;
S: 57.5±4.9,+RT 16±4.2;
G2/M:7.5±0.7,+RT 12.5±3.5.

U87/T691 cells exhibited a higher G0/G1 fraction, and reduced S and G2/M populations when compared to parental glioblastoma cells when grown asynchronously in culture either with or without radiation treatment, and the largest difference was in the G0/G1 population. Radiation-induced increases in the G2/M fraction were seen in both U87MG and U87/T691 cells, although to a greater degree in parental U87MG cells. The combination of serum deprivation and radiation treatment in these cell populations was not additive and did not appreciably alter the cell cycle distributions in either cell line from that observed with radiation treatment in full serum. Thus, disabling EGFR-mediated signaling appears to induce a growth arrest by a mechanism distinct from that observed with prolonged serum deprivation.

Trans-receptor Inhibition Sensitizes Human Glioblastoma Cells to Radiation-induced Apoptosis Human glioblastoma cells have been shown to be especially resistant to radiation treatment both experimentally and clinically. EGFR overexpression and/or mutation has been correlated with particularly aggressive human glial tumors and oncogenicity was suggested to be due to reduced apoptosis in vitro and in vivo. Whether inhibition of EGFR-mediated signaling in human glioblastoma cells by the T691stop neu mutant receptor could sensitize cells to apoptotic cell death was examined.

With prolonged serum deprivation, only 0–1% apoptosis was observed in U87MG parental cells by either 4'-6-diamidino-2-phenylindole (DAPI) staining or TUNEL staining, which was less than that observed in other studies. U87MG-derived cells were found not to exhibit a sub-G0 peak by flow cytometric analysis after PI staining under conditions causing apoptosis, which is in agreement with others. Expression of the T691stop neu inhibitor in U87MG cells resulted in only 0–2% apoptosis with prolonged serum deprivation as determined by immunohistochemical identification of apoptotic nuclei with DAPI.

Apoptosis was maximal in repeated studies at 72 h and this time point was selected for all additional experiments. Expression of the T691stop neu protein in the U87MG cell background increased the level of radiation-induced apoptosis to 23±7.9% (mean±SEM) at 72 h in four independent experiments in full growth media (FIG. 2A). Prolonged serum deprivation combined with radiation resulted in 33±10.6% apoptosis in U87/T691 cells and in 11±1.5% apoptosis in parental U87MG cells, a comparable increase in both populations above that observed with radiation of cells in full growth media. Experiments including morphologic assessment of apoptosis in human glioma cells following gamma-irradiation were performed. All cells were stained with DAPI a 72 h after being exposed to gamma-irradiation. Nuclei exhibiting apoptotic morphology were observed. The morphological changes of nuclear blebbing and fragmentation characteristic of apoptosis are shown by immunohistochemical analysis of U87MG-derived cultured cells stained with DAPI. The apoptotic indices represent an underrepresentation of total cell death after radiation in U87/T691 cells since we were unable to examine floating cells immunohistochemically.

Clonogenic Survival of Irradiated Human Glioblastoma Cells.

We measured the number of cells that escape growth arrest or death and are able to go on to form a colony, an assay commonly used to determine radiosensitivity. In certain cases, clonogenic growth assays have not correlated with sensitivity to radiation or chemotherapy, presumably since the fate of the dead or stably arrested cells is not determined in this assay. As shown in FIG. 3, U87/T691 cells exhibited increased sensitivity to radiation across a range of radiation concentrations (2–10 Gy). U87/T691 cells were approximately one-half log more sensitive to radiation than their untransfected parental counterparts at all radiation doses tested. These results were confirmed with additional T691stop neu-expressing subclones. U87MG cells and their derivatives contain wild-type p53 and p21 proteins.

Relationship of Radiation Sensitivity of Human Glioblastoma Cells to p53 Status p53 status has been shown to influence the response to ionizing radiation in a number of transformed and nontransformed cell types. An analysis of p53 induction in human glioblastoma cells following gamma-irradiation was made. $10^5$ U87MG and U87/T691 cells containing a wild-type p53 gene product were plated and gamma-irradiated (10 Gy) following attachment overnight. Lysates were then taken at the indicated times after radiation, subjected to SDS-PAGE and immunoblotted with an antibody reactive with p53. Control cells were MCF-7 breast cancer cells containing immunoreactive p53 protein. More robust induction of the p53 protein at 12 h following gamma-irradiation in U87/T691 subclones was consistently observed. Western analysis of cell lysates obtained at distinct time points following radiation treatment indicated persistent increases in p53 protein levels detected at all times between 6–72 h after radiation in both U87MG and their T691stop neu-transfected derivatives. The zero time point indicates cells which were gamma-irradiated and immediately lysed for analysis. p53 densities were comparable at this time point to mock-irradiated, cycling cells. A 10-fold increase in p53 density 12 h post-radiation in U87/T691 cells, was observed as compared to only 1.5- to 3-fold increases in both U87MG cells and U87/T691 cells at all other time points examined. This trend was consistently observed (four experiments) and was seen in U87/T691 cells as early as 6 h following radiation in some experiments, and suggests that p53-dependent signaling pathways may be more efficiently activated by disabling the EGFR in the presence of genomic damage. Alterations in p53-regulated checkpoint proteins have been observed 12 h after the induction of genomic damage by gamma-irradiation. Growth inhibition and differentiation of human breast cancer cells following ligation of erbB receptors has been associated with activation of a p53-dependent pathway.

p21 was induced in both U87MG and U87/T691 cells following radiation treatment, with highest levels seen 24 h after radiation exposure in both cell lines. In both U87MG cells and U87/T691 cells, p21 protein density 6–24 h after radiation was comparable. Although others have suggested that upregulation of bcl-$x_L$ is associated with reduced apoptosis in human glioma cells, we detected no changes in bcl-$x_L$ protein expression following radiation in either U87MG or U87/T691 cells. Both constitutive and radiation-induced bcl-$x_L$ levels were equivalent in U87MG and U87/T691 cells. Examination of bax and bcl-2 protein levels did not reveal differences between glioblastoma cells and their inhibited subclones.

Apoptosis in p53-mutated Human Glioblastoma Cells

U373MG human glioma cells contain a mutated p53 gene product, are deficient in p21 expression and display a comparable elevation of surface EGFR to U87MG cells by flow cytometric analysis. These cells were used to determine whether the observed apoptosis following inhibition of EGFR-mediated signaling and gamma-irradiation was dependent on a wild-type p53 protein. U373MG cells exhibited increases in levels of a mutated p53 protein following gamma-irradiation, but do not express p21 constitutively or after radiation treatment.

The T691stop neu mutant receptor was expressed in U373MG glioma cells and confirmed expression comparable to U87/T691 cells in four U373/T691subclones by metabolic labeling and flow cytometic analysis. Flow cytometry indicated that surface levels of the T691stop mutant neu receptor were equivalent in U87/T691, U373/T691 cl 1 and U373/T691 cl 12 subclones, and two additional T691stop neu-expressing U373MG derivatives. U373MG derivatives expressing the T691stop neu mutant receptor were capable of growth arrest in low serum, and displayed an arrested lawn of confluent cells without the development of morphologically transformed foci in vitro, indicating that p53 and p21 wild-type proteins were not required neither to arrest growth nor to inhibit transformation of glioma cells in which erbB signaling was disabled. U373/T691 cl 1 and U373/T691 cl 12 subclones were then irradiated along with U373MG cells and exhibited increased levels of apoptosis over their parental counterparts (FIG. 2B). In the representative experiment shown, two U373/T691 subclones exhibited 32% and 59% apoptosis, respectively, 72 h after gamma-irradiation, compared to 2% apoptosis in parental U373MG cells and a 20% apoptotic index in U87/T691 cells. Disabling EGFR signaling by expression of T691stop neu in two distinct human glioma cell lines containing differences in p53 and p21 status resulted in increased radiation-induced apoptosis. Sensitization of human glioblastoma cells to genomic damage can thus occur in the absence of wild-type p53 and p21 proteins. Taken together, these data suggest that both p53-dependent and p53-independent pathways may mediate sensitization to cell death induced by a combination of trans-receptor inhibition and genomic damage. Of note, human glioblastoma cells in which EGFR signaling is disabled do not appear to be more sensitive to either prolonged serum deprivation or tumor necrosis factor α-mediated cell death than parental cells.

Discussion

Specific inhibition of EGFR-signaling which inhibits cell growth and transformation also sensitized radioresistant human glioma cells to radiation-induced genomic damage. Glioblastoma cells expressing a trans-dominant p185neu-derived mutant receptor exhibited a greater G1 phase arrest and higher levels of apoptosis after radiation than their parental counterparts. In mammalian fibroblasts and in specialized neuronal cells, serum or growth factor deprivation can lead to apoptosis under particular conditions. Prolonged serum deprivation alone did not induce apoptosis in human glioblastoma cells in these studies. DNA damage combined with either disabling of erB receptor signaling or serum deprivation was required to induce apoptosis. Apoptosis was induced by radiation in 23% of U87MG derivatives and in 32–59% of U373MG-derived subclones in which EGFR was disabled (compared to only 1–2% in parental cells) in full growth media, indicating that inhibition of EGFR signaling by trans-receptor inhibition could not be overcome by growth in serum. Serum deprivation combined with radiation damage increased observed levels of apoptosis in both parental U87MG cells and T691stop neu-expressing human glioblastoma derivatives to the same degree. Notably, after DNA damage, the apoptosis observed by disabling erbB receptor signaling at the cell surface was greater than that seen with serum deprivation.

Surveillance systems, or checkpoints, have evolved to arrest the cell cycle when damage to the genome or mitotic spindle has occurred. The DNA damage checkpoint operates differentially at distinct stages of the cell cycle and requires the coordinated action of multiple pleiotropic gene products involved in growth arrest, DNA repair, transcriptional activation, and apoptosis. DNA damage checkpoints constitute signal transduction pathways communicating information from damaged DNA to cell cycle components. The data presented in these studies show that receptor tyrosine kinase (RTK)-mediated signaling events can influence DNA damage checkpoint signaling pathways. In particular, inhibition of the EGFR in malignant human glioma cells can increase the degree of growth arrest and apoptosis observed after DNA damage caused by X-rays.

Resistance of gamma-irradiated cells is affected by the functional state of distinct oncogenes. Expression of oncogenic Ras or Raf diminishes radiosensitivity in NIH3T3 cells and expression of the $Ras^H$ plus either c- or v-myc oncogenes conferred resistance to rat embryo fibroblasts exposed to gamma-irradiation. It is also true that expression of various oncogenes can sensitize cells to apoptosis, upon exposure to low serum or to anticancer agents. Division delay occurring in both the G1 and G2 phases of the cell cycle is influenced by the expression of dominant oncoproteins such as H-ras. Expression of a wild-type p53 protein has been associated with decreased survival following gamma-irradiation, due to the induction of a higher fraction of apoptosis over cells containing a mutated p53 protein. However, tumor cells containing a mutated p53 protein and proliferating lymphoid cells derived from p53-/- mice have been shown to undergo apoptosis following radiation, suggesting p53-independent mechanisms of cell death following genomic damage.

Factors mediating the degree of growth arrest versus apoptosis observed following DNA damage in a particular cell type have not been defined and cell-specific factors influencing DNA damage detection, cell recovery, and the decision to apoptose are not completely understood. p53-dependent mechanisms may influence the response of inhibited glioma cells to undergo relative growth arrest and/or apoptosis. The results in U373MG-derived cells also indicate that apoptotic cell death occurring after genomic damage in transformed human cells in which EGFR signaling is inhibited involves mechanisms that are distinct from the p53 and p21 proteins. p21-/- mice develop normally and do not appear to have defects in programmed cell death required for normal organ development, indicating that p21 is not likely to be required for apoptosis. p53-/- mice display genetic instability and contain elevated c-myc levels. These mice undergo significant levels of apoptosis in vivo, indicating that p53-independent mechanisms of apoptosis are functional in both normal tissues and transformed cells.

Interestingly, recent work demonstrates that the absence of p21 in isogenically matched colorectal carcinoma cells resulted in reduced growth arrest when compared to p21-positive derivatives of the same cell line and this was correlated to more inhibited tumor growth in vivo. These observations were ascribed to increased apoptosis due to defects in p21-mediated checkpoint growth arrest, though the increased tendency to apoptose by p21-/- cells was not directly shown in this work. Induction of apoptosis was suggested to be preferable to growth arrest in anticancer therapy in vivo. In our studies, unlike those of Waldmann et al. (1997), there was a correlation between apoptosis, increased growth arrest and reduction in clonogenic survival following radiation.

Under certain circumstances, particularly in cancer cells, apoptosis may be favored following genomic damage if defects in pathways mediating growth arrest are present. Additionally, even when cells are capable of undergoing both growth arrest and apoptosis, as in the case of p21-deficient U373MG human cells in which EGFR signaling is disabled, cells may be induced to apoptosis after certain signals such as radiation, presumably by activating distinct pathways. Our data indicate that the relative proportion of growth arrest or apoptosis induced by genomic damage is influenced by both the integrity of specific checkpoints and alterations in erbB signaling pathways. Notably, modulating RTK signaling pathways may influence checkpoint outcomes following DNA damage in transformed cells. Others have shown that activation of erbB signaling pathways in breast cancer cells contributes to radioresistance, suggesting that erbB family signaling pathways influence the response to DNA damage in many tumor types. By combining biologic inhibition of signaling with agents capable of specifically inhibiting receptor oncoproteins of the tyrosine kinase family, we may be able to influence the kinetics of tumor cell response to standard cytotoxic agents. The timing of administration of cytotoxic therapies may be optimized in such combination therapies and these data suggest that selective antitumor effects of presently available anticancer regimens could be improved, even in the treatment of advanced human malignancies containing alterations in multiple checkpoint signal transduction pathways.

Example 6

Recombinant Adenovirus

Recombinant adenoviruses according to some embodiments of the present invention are disabled by deleting E1a and E1b, which are normally required to activate the expression of other viral genes. These recombinant adenoviruses, which are based on human Ad5, are capable of very efficiently transducing genes into human hepatocytes without apparent cytopathic effects or expression of adenoviral proteins. Construction of recombinant adenoviruses which can be adapted for use in the present invention are described in Kozarsky et al. 1993 Somatic Cell and Molecular Genetics 19(5):449–458, which is incorporated herein by reference. The reference teaches recombinant adenovirus with a lacZ insert. The lacZ insert may be replaced with sequences that encode tyrosine kinase deficient, erbB-dimerizing proteins according to the invention. The gene construct of the invention is inserted in a linker sequence at the site of the lacZ insert.

Materials and Methods

Recombinant Adenoviruses. The plasmids used to generate the recombinant, E1-deleted adenoviruses Ad.CBlacZ and Ad.CBhLDLR were constructed as follows. The plasmid CMVβAlacZ (10) was digested with SnaB1 and NheI, and gagβAhLDLR (16) was digested with NheI and then partially digested with XhoI to isolate a fragments containing the β-actin promoter and either the lacZ gene or the human LDL receptor cDNA. These fragments were blunt-ended with klenow. The plasmid pAdCMV-lacZ (17) was digested with SnaBI and NotI to remove the CMV promoter and lacZ gene (retaining the CMV enhancer), blunt-ended with Klenow, and ligated with inserts containing the β-actin promoter fused to either the lacZ or LDLR genes. The resulting vectors were designated to pAdCBlacZ and pAd-CBhLDLR, respectively.

Plasmids were linearized with NheI and cotransfected into 293 cells with wild-type adenoviral DNA (strain sub 360 (18) which contains a partial E3 deletion) that had been digested with XbaI and ClaI to remove the 5'ITR. Recombinant adenoviruses were isolated following transfection (19), subjected to two rounds of plaque purification, and lysates were purified by cesium chloride centrifugation (20). The viral stocks were evaluated for titers by limiting dilution plaque assay on 293 cells and stored at 20° C. after diluting fourfold with 10 mM Tris Cl, pH 8.1, 100 mM NaCl, 0.1% bovine serum albumin, and 50% glycerol. Titers of the glycerol stocks were: Ad.CBlacZ, $2.4 \times 10^9$ plaque-forming units (PFU)/ml; Ad, CvhLDLR, $4 \times 10^9$ PFU/ml; wild-type Ad, $8 \times 10^9$ PFU/ml.

Gene constructs according to the invention are inserted in place of the lacZ sequences into a linker sequence in the plasmid.

Example 7

Recombinant Adenovirus

Recombinant adenoviruses according to some embodiments of the present invention are disabled by deleting E1 and E4 genes, which are normally required to activate the expression of other viral genes. These recombinant adenoviruses, which are based on human Ad5, are capable of very efficiently transducing genes into human hepatocytes without apparent cytopathic effects or expression of adenoviral proteins. Construction of recombinant adenoviruses which can be adapted for use in the present invention are described in PCT application serial number PCT/US96/10245, which is incorporated herein by reference. The reference teaches recombinant adenovirus with a lacZ insert. The lacZ insert may be replaced with sequences that encode tyrosine kinase deficient, erbB-dimerizing proteins according to the invention. The gene construct of the invention is inserted in a linker sequence at the site of the lacZ insert.

Figure 4:
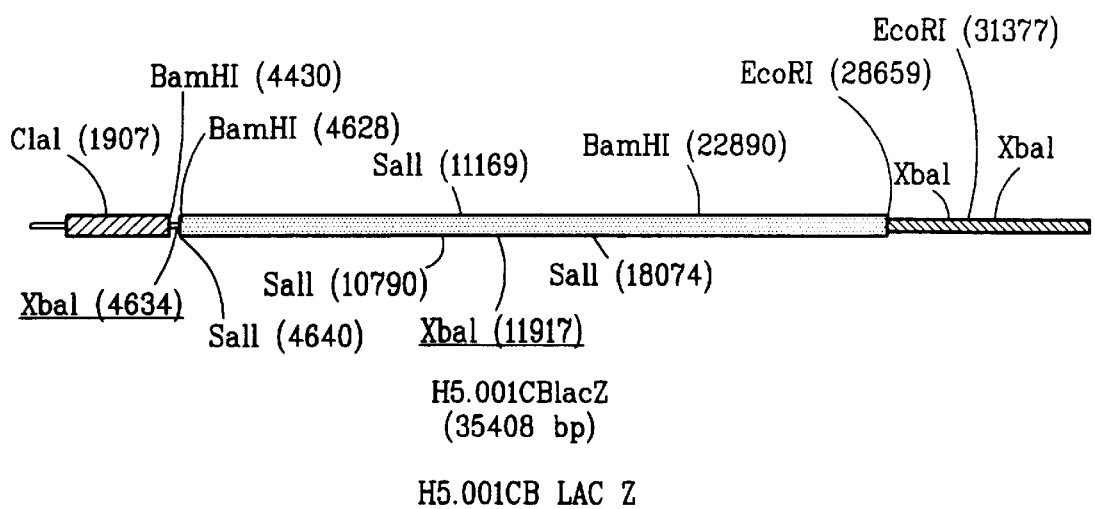
FIG. 4 is a schematic map of recombinant adenovirus H5.001CBLacZ.

FIG. 4 is a schematic map of recombinant adenovirus H5.001CBLacZ, with indicated restriction endonuclease enzyme sites. The striated bar represents the CBLacZ minigene; the black bar represents Ad5 viral backbone, the crosshatched bar represents Ad E4 deletion.

Novel packaging cell lines enable the production of recombinant adenoviruses functionally deleted in both the E1 and E4 genes.

Early region 4 (E4) of adenovirus serotype 5 consists of 7 open reading frames (ORFs) believed to be involved in viral DNA replication, host cell shut-off, and late mRNA accumulation. To generate recombinant adenoviruses (Ad) deleted in E4, the function of the E4 region must be supplied to the recombinant virus by a helper virus or packaging cell line.

To avoid this problem, the packaging cell line contains the Ad5 E1 gene and only the ORF6 of the Ad5 E4 gene. ORF6 of E4 alone can provide the requirements for E4 in the viral life cycle. The ORF6 is further preferably under the transcriptional control of an inducible promoter, such as the sheep metallothionine promoter, inducible by zinc, or the mouse mammary tumor virus (MMTV) promoter, inducible by a glucocorticoid, particularly, dexamethasone.

After the desired shuttle vector containing the adenoviral sequences is transfected into the cell line, expression of the E4 ORF6 can be induced by the appropriate inducer.

In a preferred form, the packaging cell line is a human embryonic kidney (HEK) 293 E1 expressing cell line into which is introduced the E4 ORF 6 sequence under the control of an inducible promoter. The MMTV promoter with its glucocorticoid inducer is presently preferred, because the zinc sulfate inducer of the MT promoter can itself be toxic to the cells.

Specific teaching of the construction of packaging cell lines containing only the ORF 6 of Ad5 E4 region or, for functional comparisons, the entire E4 region is set forth below. Briefly described, the entire E4 region and an ORF6 sequence of Ad E4 gene are obtained by known techniques (see, e.g., Sambrook et al., "Molecular Cloning. A Laboratory Manual.", 2d edit., Cold Spring Harbor Laboratory, New York (1989) and references cited therein which are all incorporated by reference). To isolate the ORF6 region, the anchored polymerase chain reaction technique was used to amplify the ORF6 sequence from its initiation codon to its termination codon. Primers selected from the published sequence of ORF6 are used to amplify the ORF sequence and insert restriction sites onto the end of the sequence. The entire E4 gene sequence including the E4 ORF6 sequence is published in the Genbank sequence of Ad5 (Genback Accession No. M73260).

A minigene is constructed that placed the ORF6 sequence under the control of a selected promoter. The ORF6 sequence gene is operatively linked to regulatory components in a manner which permits its transcription. Such components include conventional regulatory elements, such as a promoter to drive ORF6 expression. One inducible promoter was an $Zn^{+2}$ inducible sheep metallothionine (MT) promoter (M. G. Peterson et al., Eur. J. Biochem., 174: 417–424 (1988)). The second promoter is the dexamethasone-inducible mouse mammary tumor virus (NMTV) promoter.

The polyA sequence employed in the MMTV-ORF6 minigene is supplied by the growth hormone gene terminator and an SV40 origin of replication.

The ORF6-containing minigene is subcloned into a pBR322-based shuttle plasmid that contained a neomycin resistance gene, resulting in a shuttle vector.

The E1/E4 ORF6 expressing packaging cell lines are useful in the generation of recombinant E1/E4 deleted adenoviruses.

Recombinant Adenoviruses

The novel E1/E4 expressing cell line is useful in further constructing E1/E4 deleted recombinant adenoviruses containing any selected transgene. The recombinant adenoviruses are capable of delivering a suitable gene to mammalian cells and tissues. These recombinant adenoviruses are functionally deleted in at least the E1a, E1b and E4 Ad gene regions. By the term "functionally deleted" is meant that a sufficient amount of the gene region is removed or otherwise damaged, e.g., by mutation or modification, so that the gene region is no longer capable of producing the products of gene expression. If desired, the entire gene region may be removed.

Similarly, the methods employed for the selection of viral sequences useful in a vector, the cloning and construction of the "minigene" and its insertion into a desired viral shuttle vector and the production of a recombinant infectious virus are within the skill in the art given the teachings provided herein.

Construction of the Transgene Containing "Minigene"

A minigene in this context is defined as above, except that the components of this minigene are designed to express the gene product in vivo. Such components include conventional regulatory elements necessary to drive expression of the transgene in a cell transfected with the recombinant virus. For this minigene, a selected promoter is operatively linked to the transgene and located, with other regulatory elements, within the selected viral sequences of the recombinant vector. Selection of the promoter is a routine matter and is not a limitation of this invention. Useful promoters may be constitutive promoters or regulated (inducible) promoters, which will enable control of the amount of the transgene to be expressed. For example, a desirable promoter is that of the cytomegalovirus (CMV) immediate early promoter/enhancer (see, e.g., Boshart et al., Cell, 41:521–530 (1985)).

Another desirable promoter includes the Rous sarcoma virus LTR promoter/enhancer. Still another promoter/enhancer sequence is the chicken cytoplasmic β-actin (CB) promoter (T. A. Kost et al., Nucl. Acids Res., 11(23):8287 (1983)). Other suitable promoters may be selected by one of skill in the art.

Production of Recombinant Adenovirus

Adenovirus sequences useful in this invention may include the DNA sequences of a number of adenovirus types, which are available from Genbank, including type Ad5 (Genbank Accession No. M73260). The adenovirus sequences may be obtained from any known adenovirus serotype, such as serotypes 2, 3, 4, 7, 12 and 40, and further including any of the presently identified 41 human types.

Similarly adenoviruses known to infect other animals may also be employed in the vector constructs of this invention. The selection of the adenovirus type is not anticipated to limit the following invention. A variety of adenovirus strains are available from the American Type Culture Collection, Rockville, Md., or available by request from a variety of commercial and institutional sources. In the following exemplary embodiment an adenovirus, type 5 (Ad5) is used for convenience.

An adenovirus of this invention contains a functional deletion of the adenoviral early immediate early gene E1a (which spans mu 1.3 to 4.5) and delayed early gene E1b (which spans mu 4.6 to 11.2). Similarly the adenovirus has a functional deletion of the E4 region (which spans mu 92 to 97.2), or at least of ORF6 of the E4 region.

Exemplary recombinant adenoviruses for use in this invention, for example, may be obtained by homologous recombination of desired fragments from various recombinant adenoviruses, a technique which has been commonly employed to generate other recombinant adenoviruses for gene therapy use. The recombinant adenovirus, H5.001CBLacZ, is constructed by homologous recombination between the adenovirus dl1004 (also H5dl1004) viral backbone and pAdCBLacZ minigene DNA. H5dl1004 is an Ad5 virus deleted of from about map unit 92.1 through map unit 98, i.e., substantially the entire E4 gene. The dl1004 virus is described in Bridge and Ketner, J. Virol., 632(2): 631–638 (February 1989), incorporated by reference herein.

The pAdCBLacZ vector is a cDNA plasmid containing Ad m.u. 0–1, an E1 deletion into which is inserted a bacterial β-galactosidase gene under the control of a chicken β-actin promoter, with other regulatory elements as described below, and flanked by Ad m.u. 9–16 and plasmid sequence.

Novel E1a/E1b and E4 Expressing Packaging Cell Lines

Construction of E4 ORF6 Expressing Plasmids pMTE4ORF6

One exemplary plasmid useful for the construction of a packaging cell line of this invention is pMTE4ORF6, which contains a sheep metallothionine promoter (MT promoter) in control of the transcription of a human E4 ORF6 gene sequence, a growth hormone terminator (GH), an SV40 origin of replication, plasmid sequences from pBR322-based plasmid including a neomycin resistance gene, an SV40 polyadenylation site and an ampicillin resistance gene.

The various functional fragments of this plasmid may be readily replaced with other conventionally used sequences and are not critical to the design of the plasmid.

pMMTVE4ORF6

Another exemplary plasmid useful for the construction of a packaging cell line of this invention is pMMTVE4ORF6, which contains a mouse mammary tumor virus promoter (MMTV) in transcriptional control of a human E4 ORF6 gene sequence, a growth hormone terminator (GH), an SV40 origin of replication, plasmid sequences from plasmid pBR322, including a neomycin resistance gene, and an ampicillin resistance gene. The various functional fragments of this plasmid may be readily replaced with other conventionally used sequences and are not critical to the design of the plasmid.

pLTR.E4(−) Endogenous E4 Promoter

A plasmid used as a control for the construction of a packaging cell line of this invention is pLTR.E4(−). This plasmid contains the constitutive retroviral MLV LTR and most of the Ad E4 gene region except that the endogenous E4 promoter and a portion of E4 ORF1 are missing. The other plasmid sequences remain the same as described above.

pLTR.E4(+) Endogenous E4 Promoter

Still another plasmid is pLTR.E4, which contains the constitutive MLV LTR and endogenous E4 promoter and an intact E4 gene. The other plasmid sequences remain the same as described above.

Transfections and Selections of Clones

Each of the above-described plasmids was transfected by the calcium phosphate precipitation technique into the human embryonic kidney cell line 293 (ATCC CRL1573) which expresses the product of the adenovirus E1 genes, seeded on 100 mm plates (10 µg plasmid/plate). Twenty four hours post-transfection, cells were harvested and seeded at varying dilutions (1:10–1:100) in 100 mm plates for about 10 days. Seeding media contain G418 (Geneticin, BRL) at 1 mg/ml. Resistant colonies that developed were selected using the following assays and expanded. Preliminary analysis of clones was based on enhanced transduction efficiency of a recombinant adeno-associated virus, AV.CMVLacZ, and immunofluorescence localization of Ad Er protein as follows.

AV.CMBLacZ Transduction Enhancement Assay

E1 and E4 Ad gene products are needed for recombinant adeno-associated virus (AAV) function. This primary assay involves seeding the packaging cell lines of Example 1 in 96 well 35 mm culture plates ($2 \times 10^6$ cells/well) and infecting the cells with purified, heat-treated AV.CMVLacZ at an MOI of 1000 virus particles/cell.

Preparation of AV.CMVLacZ

A recombinant AAV virus is prepared by conventional genetic engineering techniques for the purposes of this experiment. Recombinant AAV is generated by plasmid transfections in the presence of helper adenovirus (Samulski et al., J. Virol., 63:3822–3828 (1989)). A cis-acting plasmid pAV.CMVLacZ is derived from psub201 (Samulski et al., J. Virol. 61:3096–3101 (1987)) and contains an *E. coli* βgalactosidase minigene in place of AAV Rep and Cap genes. The 5' to 3' organization of the recombinant AV.CMVLacZ genome (4.9 kb) includes (a) the 5'AAV ITR (bp 1–1 73) was obtained by PCR using pAV2 (C. A. Laughlin et al., Gene, 23:65–73 (1983)) as template;

(b) a CMB immediate early enhancer/promoter (Boshart et al., Cell, 41:521–530 (1985));

(c) an SV40 intron;

(d) *E. coli* beta-galactosidase cDNA;

(e) an SV40 polyadenylation signal (a 237 Bam HI-BclI restriction fragment containing the cleavage/poly-A signals from both the early and late transcription units; and (f) 3' AAV ITR, obtained from pAV2 as a SnaBI-BglII fragment. Rep and Cap genes are provided by a trans-acting plasmid pAAV/Ad.

Monolayers of 293 cells grown to 90% confluency in 150 mm culture dishes ($5 \times 10^7$ cells/plate) are infected with H5.CBALP at an MOI of 10. H5.CBALP (also called (H5.0101ALP) is a recombinant adenovirus that contains an alkaline phosphatase minigene in place of adenovirus E1A and E1b gene sequences (map units 1–9.2 of the Ad5 sequence of GenBank (Accession No.M73260)). The alkaline phosphatase cDNA is under the transcriptional control of a CMV-enhanced β-actin promoter in this virus. This helper virus is described in Goldman et al., Hum. Gene Ther., 6:839–851 (July, 1995); Engelhardt et al., Hum. Gene Ther., 5:1217–1229 (October, 1994); and references cited therein.

Infections are done in Dulbecco's Modified Eagles Media (DMEM) supplemented with 2% fetal bovine serum (FBS) at 20 ml media/150 mm plate. Two hours post-infection, 50 µg plasmid DNA (37.5 µg transacting and 12.5 µg cis-acting) in 2.5 ml of transfection cocktail is added to each plate and evenly distributed. Transfections are calcium phosphate based as described (B. Cullen, Meth. Enzymol., 152:684–704 (1987)). Cells are left in this condition for 10–14 hours after which the infection/transfection media is replaced with 20 ml fresh DMEM/2% FBS. Forty to fifty hours post-transfection, cells are harvested, suspended in 10 mM Tris-Cl (pH 8.0) buffer (0.5 ml/150 mm plate) and a lysate prepared by sonication. The lysate is brought to 10 mM manganese chloride, after which bovine pancreatic Dnase I (20,000 units) and Rnase (0.2 mg/ml final concentration) were added, and the reaction incubated at 37° C. for 30 minutes. Sodium deoxycholate is added to a final concentration of 1% and incubated at 37° C. for an additional 10 minutes.

The treated lysate is chilled on ice for 10 minutes and solid CsCl added to a final density of 1.3 g/ml. The lysate is brought to a final volume of 60 ml with 1.3 g/ml CsCl solution in 10 mM Tris-Cl (pH 8.0) and divided into three equal aliquots. Each 20 ml sample is layered onto a CsCl step gradient composed of two 9.0 ml tiers with densities 1.45 g/ml and 1.60 g/ml.

Centrifugation is performed at 25,000 rpm in a Beckman SW-28 rotor for 24 hours at 4° C.

Fractions containing peak titers of functional AV.CMV-LacZ virus are combined and subjected to three sequential rounds of equilibrium sedimentation in CsCl. Rotor selection includes a Beckman NVT-90 (80,000 rpm for 4 hours) and SW-41 (35,000 rpm for 20 hours). At equilibrium, AV.CMVLacZ appears as an opalescent band at 1.40–1.41 g/ml CsCl. Densities are calculated from refractive index measurements. Purified vector is exchanged to 20 mM HEPES buffer (pH7.8) containing 150 mM NaCl (HBS) by dialysis and stored frozen at −80° C. in the presence of 10% glycerol or as a liquid stock at −20° C. in HBS/40% glycerol.

Purified virus is tested for contaminating H5.CBALP helper virus and AV.CMVLacZ titers. Helper virus is monitored by histochemical staining for reporter alkaline phosphatase activity. A sample of purified virus representing 1.0% of the final product is added to a growing monolayer of 293 cells seeded in a 60 mm plate. Forty-eight hours later, cells are fixed in 0.5% glutaraldehyde/phosphate buffered saline (PBS) for 10 minutes at room temperature, washed in PBS (3×10 minutes) and incubated at 65° C. for 40 minutes to inactivate endogenous alkaline phosphatase activity. The monolayer is allowed to cool to room temperature, rinsed once briefly in 100 mM Tris-Cl (pH9.5)/100 mM NaCl/ 5mM MgCl, and incubated at 37° C. for 30 minutes in the same buffer containing 0.33 mg/ml nitroblue tetrazolium chloride (NBT) and 0.165 mg/ml 5-bromo4-chloro-3-indolyphosphate p-toluidine salt (BCIP). Color development is stopped by washing the monolayer in 10 mM Tris-Cl (pH 8.0)/5 mM EDTA. Routinely the purification scheme described above removes all detectable H5.CBALP helper virus by the third round of buoyant density ultracentrifugation.

AV.CMVLacZ titers are measured according to genome copy number (virus particles/ml), absorbance at 260 nm ($A_{260}$ particles/ml) and LacZ Forming Units (LFU/ml). Virus particle concentrations are based on Southern blotting. Briefly, a sample of purified AV.CMVLacZ is treated with capsid digestion buffer (50 mM Tris-Cl, pH 8.0/1.0 mM EDTA, pH 8.0/0.5% SDS/Proteinase K 1.0 mg/ml) at 50° C. for one hour to release virus DNA. The reactions are allowed to cool to room temperature, loading dye was added and electrophoresed through a 1.2% agarose gel. Standard quantities of ds AV.CMVLacZ genome are also resolved on the gel.

DNAs are electroblotted onto a nylon membrane, hybridized with a $^{32}p$ random primer labeled restriction fragment, and the resulting blot scanned on a PhosphorImager 445 SI (Molecular Dynamics). A standard curve is generated from the duplex forms and used to extrapolate the number of virus genomes in the sample. LFU titers are generated by infecting indicator cells with limiting dilutions of virus sample. Indicator cells include HeLa and 293. Twenty-four hours later, cells are fixed in glutaraldehyde and cells are histochemically stained for E. coli β-galactosidase (LacZ) activity as described in J. M. Wilson et al., Proc. Natl. Acad. Sci. USA, 85:3014–3018 (1988). One LFU is described as the quantity of virus that is sufficient to cause visually detectable β-galactosidase expression in one cell 24 hours post-infection.

Induction of ORF6 Expression

Induction of ORF6 expression with 10 μM dexamethasone or 150 μM zinc sulfate (for negative control, no inducer used) is initiated 2 hours before the addition of virus and continued throughout the duration of the experiment. Twenty-four hours after the addition of virus, cells are harvested, lysates are generated by sonication and analyzed for the β-galactosidase expression (i.e., β-galactosidase activity) and virus DNA as described above. Hirt extracts are prepared for low molecular weight DNA from cell extracts. The preparation of the Hirt extracts and subsequent analysis by Southern hybridization are performed by resort to conventional procedures known to one of skill in the art.

In the absence of the inducers, the packaging cell lines generate lower levels of β-galactosidase in rAAV infected cells. Induction of ORF6 expression with the inducer dexamethasone results in a concomitant rise in AV.CMVLacZ cell transduction to a level that is much greater than the parent 293 line. Expression of E1 alone is insufficient to have an effect in the adenovirus mediated augmentation of rAAV transduction.

Immunofluorescence Localization of Ad5 Late Protein

Positive clones from the assay are infected with the recombinant E4 deleted adenovirus H5D11004 and screened for E4 complementation using an immunofluorescence assay for late gene expression. The H511004 virus was obtained from Dr. Ketner of Johns Hopkins University and is described in Bridge and Ketner, J. Virol., 632(2):63 1–638 (February 1989), incorporated by reference herein. Because ORF6 of E4 complements late Ad gene expression, specifically in the formation of the hexon and penton fibers of the adenovirus, cell lines containing ORF6 are able to bind with antibody against these proteins.

Each cell line is infected with E4 deleted virus H5d11004 virus at an MOI of 0.1. The cells are treated with mouse anti-adenovirus FITC-labeled monoclonal antibody to either the hexon or penton fibers in a 1:10 dilution (Chemicon International Inc., Temecula, Calif.). Positive clones are identified by reaction with the antibody.

Relative Plaquing Efficiency

The cell lines demonstrating strong complementation ability are screened for relative plaquing efficiency of H5d11004 as compared to W162 cells (an E4-complementing Vero cell line which does not express E1) (Weinberg and Ketner, Proc. Natl. Acad. Sci., USA, 80(17):5383–5386 (1983)). RPE%, i.e., relative plaquing efficiency, representing the titer of H5d11004 on tested cell lines/titer of H5d11004 on W162 cells are determined. For example, the RPE of 293 cells is 0.

The positive cell lines selected by all criteria are identified in Table I below, with the results of the assays.

TABLE I

E1/E4 Double Complementing Cell Lines

| Cell Line | Trans-Gene | Promoter | AV.CMV IF/LP LacZ | | RPE % |
|---|---|---|---|---|---|
| 293-10-3 | ORF6 | MT | ++++ | ++++ | 246 |
| 293-39-11 | ORF6 | LTR | ++++ | +++ | 52 |
| 293-84-31 | E4- | LTR | ++++ | ++++ | 179 |
| 293-12-31 | whole E4 | LTR + E4 | ++++ | ++++ | 174 |
| 293-27-6 | ORF6 | MMTV | | +++++ | 327 |
| 293-27-17 | ORF6 | MMTV | | ++++ | 313 |
| 293-27-18 | ORF6 | MMTV | | ++++ | 339 |
| 293-27-28 | ORF6 | MMTV | | ++++ | 261 |

Construction and Purification of H5.001CBLacZ

The plasmid pAd.CBLacZ is constructed as described in detail in K. Kozarsky et al., Som. Cell Mol. Genet., 19(5): 449–458 (1993), incorporated by reference herein. This plasmid contains a minigene comprising a 5' flanking NheI restriction site, followed by Ad5 sequence m.u. 0–1, followed by an E1 deletion into which is inserted a CMV enhancer/chicken β-actin promoter sequence (T.A. Kost et al., Nucl. Acids Res., 11(23):8287 (1983)), which controls the transcription of the following bacterial β-galactosidase, followed by a poly A sequence and flanked 3' by Ad m.u. 9–16, and another NheI site. In the plasmid, the minigene is flanked on both sides by plasmid sequence containing drug resistance markers.

The plasmid pAd.CBLacZ is linearized with NheI and co-transfected by the calcium phosphate co-transfection method into the novel packaging cell line with ClaI digested H5d11004 (an Ad5 sequence deleted of from about map unit 92.1 through map unit 98, corresponding to substantially the entire E4 gene).

Homologous recombination occurs in the cell line between these two viral constructs between Ad map units 9–16, resulting in recombinant adenovirus, designated H5.001CBLacZ. This recombinant adenovirus contains the sequence from about nucleotide 1 to about 4628 from pAd.CBLacZ and Ad5 map units 9–92.1 and 97.3 to 100 from H5d11004. This recombinant adenovirus is thereby functionally deleted, and substantially structurally deleted, of the Ad E1 and E4 genes.

Viral plaques were selected and screened by the β-galactosidase assay and H5.001CBLacZ isolated following three rounds of plaque purification. The purified virus is also subjected to cesium chloride density centrifugation and large scale production. For the following mouse experiments, virus is used after column purification and glycerol is added to a final concentration of 10% (v/v). Virus is stored at −70° C. until use.

Growth Kinetics of H5.001CBLacZ in Packaging Cell Lines

The cell lines described above are infected with recombinant H5.001CBLacZ at an MOI of 0.5. Maximum viral yield is reported as LFU/ml in Table II below.

TABLE II

| Cell Line | Maximum Viral Yield |
| --- | --- |
| 293-10-3 | $2.8 \times 10^{10}$ |
| 293-39-11 | $9.5 \times 10^{8}$ |
| 293-84-31 | $1.1 \times 10^{9}$ |
| 293-12-31 | $4.5 \times 10^{8}$ |
| 293-27-6 | $2.8 \times 10^{10}$ |
| 293-27-17 | $2.5 \times 10^{10}$ |
| 293-27-18 | $2.9 \times 10^{10}$ |
| 293-27-28 | $1.2 \times 10^{10}$ |

When grown in 293-27-18 cells (the E4 ORF6 cell line with MMTV promoter inducible by dexamethasone) the maximum yield of this virus is $2.9 \times 10^{10}$ LFU/ml. Several of the cell lines are passaged between 5 and 20 times and the viral production of the passages remained stable. However, RPE did fall following repeated passages of cells.

Gene constructs according to the invention are inserted in place of the lacZ sequences into a linker sequence in the plasmid.

Example 8

Background

Anti-p185$^{neu}$ monoclonal antibodies (mAbs) have been found to inhibit the growth of p185$^{neu}$ expressing tumors in a dose-dependent manner in vitro and in vivo. Combinations of anti-p185$^{neu}$ mAbs reactive with distinct epitope domains revealed a synergistic inhibitory effect on neu-overexpressing of tumors in vivo. These studies demonstrated the potential of mAb-based oncoprotein-specific therapies.

The three-dimension structure of antigen-antibody complexes reveals that the binding site is defined by 6 hyper-variable complimentarily determining regions (CDRs) loop structures (Peterson and Greene, 1994), but the specificity of interactions is conferred by the CDR3 loops. The prerequisite of conformation and structure of CDR loops can be imitated by small peptides when the sequence and structure of anti-receptor antibodies are known.

Inhibition of cell growth and transformation can be achieved in transformed glial cells by modulating erbB receptor's signaling. Recent studies by us indicate that the induction of apoptosis may underly successful therapy of human cancers. Radiation resistant human glioblastoma cells in which erbB receptor signaling was inhibited by transfection of truncated neu T691, exhibited increased growth arrest and apoptosis in response to DNA damage. Inhibition of erbB signaling is a potent stimulus for the induction of apoptosis. Proximal receptor interactions between erbB receptor members thus influence cell cycle check point pathways activated in response to DNA damage. Therefore, disabling erbB receptors may improve the response to gamma-irradiation and other cytotoxic therapies.

Data suggest that radioresistant human tumor cells which need complete erbB signaling pathway, can be turned to be radiation sensitive and to be in apoptotic pathway to any DNA damage by inhibition of erbB signaling pathway.

Anti-p185$^{c-erbB-2}$ mimetic, CDR4D5 was designed and developed and used to investigate whether the mimetic CDR4D5 derived from anti-p185$^{c-erbB-2}$ Ab can inhibit human tumor cell proliferation and enhance apoptosis following gamma-irradiation. The experiments performed are described below.

Material and Method

1. Peptidomimetic Design

Anti-erbB2 antibody, 4D5 has been shown to be effective in down modulating the erbB2 receptor. The crystal structure of the humanized antibody (1FVD) is analyzed. The CDR3 of 4D5 was used as a template. Several analogs of cyclic peptides were generated. Peptides which may be used include

| | |
| --- | --- |
| SEQ ID NO: 1 | FCGDGFYACYMDV-CONH2 |
| SEQ ID NO: 2 | FCDGFYACYMDV-CONH2 |
| SEQ ID NO: 3 | FCDPFYACYMDV-CONH2 |
| SEQ ID NO: 4 | FCPDGFYACYMDV-CONH2 |
| SEQ ID NO: 5 | FCDPPFYACYMDV-CONH2 |
| SEQ ID NO: 6 | FCDGFYACYMDV-CONH2 |
| SEQ ID NO: 7 | FCDPFYACYMDV-CONH2 |
| SEQ ID NO: 8 | FCDPPFYACYMDV-CONH2 |
| SEQ ID NO: 9 | FCGDGFYACYMDV-COOH |
| SEQ ID NO: 10 | FCDGFYACYMDV-COOH |
| SEQ ID NO: 11 | FCDPFYACYMDV-COOH |
| SEQ ID NO: 12 | FCPDGFYACYMDV-COOH |
| SEQ ID NO: 13 | FCDPPFYACYMDV-COOH |
| SEQ ID NO: 14 | FCDGFYACYMDV-COOH |
| SEQ ID NO: 15 | FCDPFYACYMDV-COOH |
| SEQ ID NO: 16 | FCDPPFYACYMDV-COOH |

2. Cell Lines

The following human tumor cell lines expressing variable levels of p185$^{c-erbB-2}$ receptor were used: a) U87MG (undetectable p185$^{c-erbB-2}$), b) parental U373MG and T691 transfected U373/T691 expressing low-moderate p185$^{c-erbB-2}$, c) MCF7 expressing moderate p185$^{c-erbB-2}$, and SKBR3 (high level of p185$^{c-erbB-2}$).

3. Flow Cytometric Analysis of Surface c-erbB-2 Receptor Expression

Subconfluent cells were harvested by quick treatment with trypsin (<3 min), and kept on ice. Cells were washed and resuspended in FACS buffer (PBS with 0.5% BSA and 0.1% NaAzide) at a concentration about $2\times10^6$ cells/ml, then incubated with the primary reagents (anti-p185$^{c\text{-}erbB\text{-}2}$ Ab) and the secondary (anti-IgG-FITC) reagents for 30 min each at 4° C., with 2 washed between each step. After staining, cells were resuspended in FACS buffer and immediately analyzed. Flow Cytometric analysis was performed on a Becton-Dickinson FACScan. Positive p185$^{c\text{-}erbB\text{-}2}$ cell lines were determined by the difference in mean channel fluorescence between cell lines stained with anti-receptor antibody and corresponding cell lines stained with the secondary (anti-IgG-FITC) reagents alone. The homogeneity of p185$^{c\text{-}erbB\text{-}2}$ positive clones was determined by the peak of the positively stained cell population around its axis. On FACS histograms, increased fluorescence is indicated by a shifting to the right of the positive peak, away from the background peak. Higher surface receptor expression correlated with the degree of shift. Relative receptor numbers on each cell type are estimated by comparing mean fluorescence intensity with that from cells with known receptor copy numbers.

4. Cell Proliferation Assay

Proliferation assay as measured by MTT [3-(4,5-Dimethylthiazol-2-yl)-2, 5-diphenyltetrazolium Bromide] incorporation. Cell lines were plated in 96-well plates (5,000 cells/well) in 10% DMEM with indicated amount of mimetic CDR4D5 and were incubated for 48 hours. MTT was given to the cells for 4 hours. The cells were lysed in 50% SDS/20% dimethyl sulfoxide and kept at 37° C. overnight. Proliferation was assessed by taking optical density reading at 570 nm, using an ELISA reader. The number of cells used in this assay was determined to be within the linear range for this cell type.

5. Radio-sensitizing Effect of the Anti-p185$^{c\text{-}erbB\text{-}2}$ mimetic CDR4D5 as determined by Morphologic Analysis of Apoptosis 30,000 cells were allowed to attach to coverslips overnight in 6 well plates. Cells were incubated with 50 μg/ml of mimetic CDR4D5 for 48 hours prior to irradiation. 10 Gy of irradiation was given and cells were incubated at 37° C. Nuclear morphology was assessed at the following time points: 12, 24, 48 and 72 hours after irradiation. Coverslips were washed twice with PBS at the indicated times, and fixed in 50:50 mix of ice-cold methanol/acetone for 1 minute. Fixed cells were subsequently stained with 4', 6'-Diamidino-2-phenylindole dihydrochloride hydrate (DAPI) (Sigma., St. Louis, Mo.) at a concentration of 0.25 ng/ml in PBS and morphologic assessment of apoptotic nuclei was determined using direct counting. Inter-observer consistency in apoptosis counts were confirmed with terminal deoxynucleotidyl transferase-mediated dUTP nick end labeling (TUNEL)-staining and by analysis of three independent observers.

Cell counts were performed within 30 minutes of staining and photographs were taken on a Zeiss Axioplan epiflouorescence microscope. At least three independent fields of 100 cells were counted for each sample.

Results

1. Expression of Surface c-erbB-2 Receptor

Flow cytometric analysis was used to determine surface p185$^{c\text{-}erbB\text{-}2}$ receptor expression on human tumor cells. The expression of surface c-erbB-2 receptor was highest in SkBR3, moderate in MCF7, low moderate in U373MG, and undetectable in U87MG. The mean fluorescence of the SKBR3 was 50 times of the control and that of MCF7, U373MG, and U87MG were 6.5, 2, and 1 times of the control, respectively.

2. Inhibition of Proliferation

Figure 5:
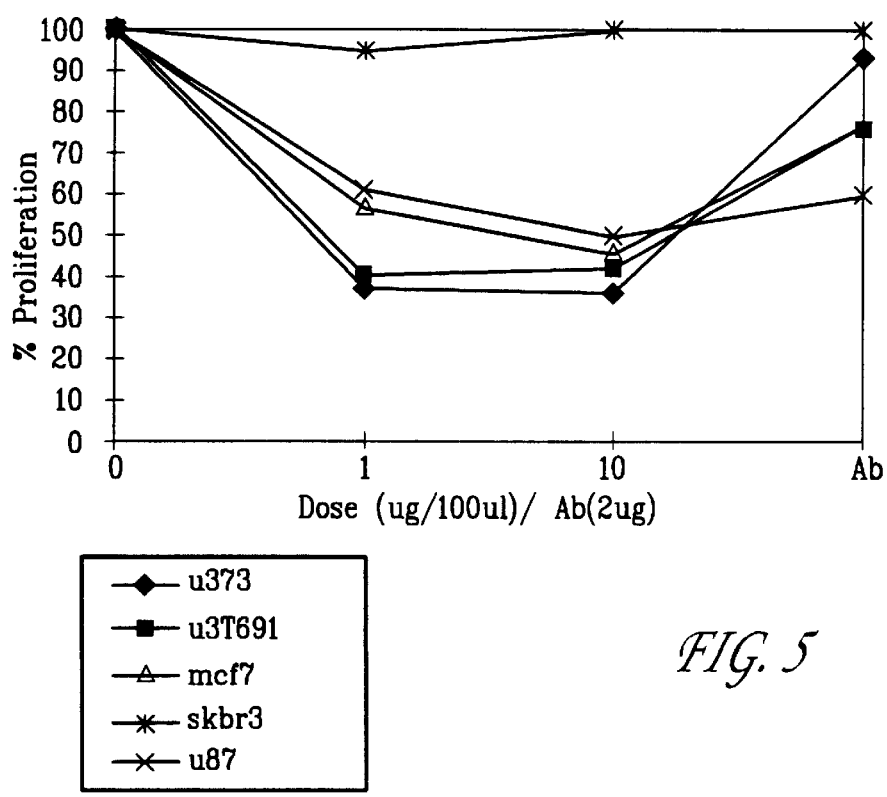
FIG. 5 show inhibition of cell proliferation of $p185^{c-erbB-2}$ expressing human tumor cells. 5,000 cells/well were plated with indicated amount of mimetic CDR4D5 or anti-$p185^{c-erbB-2}$Ab (Neomarkers Inc., Calif.) and incubate at 37 degrees for 24 hours. 100 $\mu g$ of MTT (in 200 $\mu l$) was added to each well for 4 hours, followed by addition of 100 $\mu l$ of lysis buffer to each well. After 12–24 hours, O.D. was read at 570 nm ELISA reader. %proliferation indicates degree of proliferation relative to the control cells (without mimetic CDR4D5 or anti-$p185^{c-erbB-2}$ Ab treatment).

CDR4D5 treatment inhibited tumor cell proliferation in a dose-dependent and surface p185$^{c\text{-}erbB\text{-}2}$ receptor density inversely dependent manner. CDR4D5 did not inhibit proliferation of c-erbB-2 non-expressing U373MG parental and U373/T691 was inhibited 62% with 1 μg of mimetic CDR4D5. Proliferation of MCF7 and SKBR3 cells was inhibited 43%–53%, and 39%–49% respectively in a dose-dependent manner (FIG. 5).

3. Radiosensitizing Effect of the Anti-p185$^{c\text{-}erbB\text{-}2}$ mimetic CDR4D5

Figure 6A:
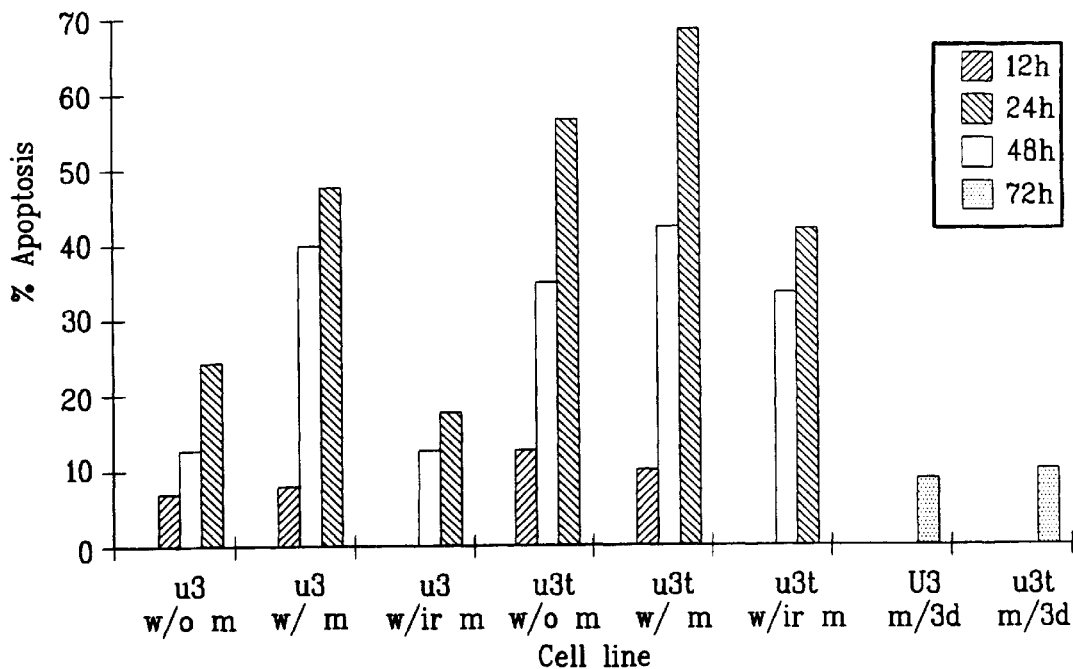
FIGS. 6A and 6B show that anti-$p_{185}{}^{c-erbB-2}$ mimetic CDR4D5 sensitizes human tumor cells to gamma-irradiation induced apoptosis. u3, u3t, S and M indicate U373MG and U373/T691, SKBR3 and MCF7 cell line, respectively. m and ir m indicate mimetic 4D5 and irrelevant mimetic CD4-Serine.
Figure 6B:
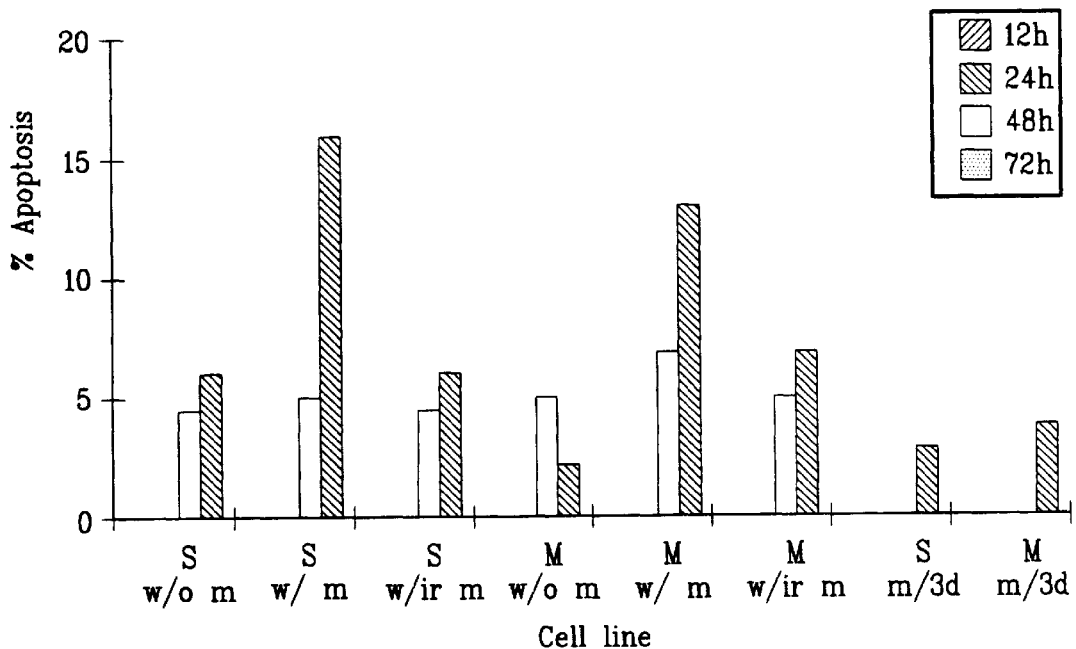

Apoptosis was maximal at 72 hours following radiation in all cells. Mimetic CDR4D5 treatment on U373MG cell resulted in 20–28% more apoptosis than nontreated U373MG cells at 48 h and 72 h after radiation. The effect of CFR4D5 treatment on apoptosis in U373MG cells was comparable with that resulted with truncated neu, an inhibitory receptor mutant which disables erbB signaling and induces increased apoptosis in response to radiation (FIG. 6A). A significant radiosensitizing effect of CDR4D5 was observed 72 hours after radiation in MCF7 and SKBR3 cell lines as well (FIG. 6B). Since sensitivity to apoptotic cell death correlated inversely with surface p185$^{c\text{-}erbB\text{-}2}$ receptor levels increasing the amount of CDR4D5 according to the amount of surface c-erbB-2 receptor expression should improve the effect.

This 4D5 mimetic is approximately 1.5 KD sized small, protease-resistant peptide which is specific to human p185$^{c\text{-}erbB\text{-}2}$ receptor and is less immunogenic than full length antibodies. The 4D5 mimetic illustrates the use of anti-receptor mimetics in cancer diagnosis and treatment, yielding synergistic effects which combined with cytotoxic therapeutics such as gamma-irradiation.

What is claimed is:

1. A method of treating an individual who has p185-mediated tumor by killing cells of the p185-mediated tumor, the method comprising the steps of:
   a) administering to said individual a peptide which inhibits formation of erbB protein dimers that comprise p185, wherein inhibiting formation of erbB protein dimers that comprise p185 renders the tumor cell more sensitive to radiation induced cell death; and
   b) exposing said individual to a therapeutically effective amount of anti-cancer radiation whereby the anti-cancer radiation kills cells of the p185-mediated tumor.

2. The method of claim 1 wherein said peptide is selected from the group consisting of SEQ ID NOS: 1–5 and SEQ ID NOS: 9–13.

3. The method of claim 2 said peptide is SEQ ID NO:1.

4. The method of claim 2 wherein said peptide is SEQ ID NO:2.

5. The method of claim 2 wherein said peptide is SEQ ID NO:3.

6. The method of claim 2 wherein said peptide is SEQ ID NO:4.

7. The method of claim 2 wherein said peptide is SEQ ID NO:5.

8. The method of claim 2 wherein said peptide is SEQ ID NO:9.

9. The method of claim 2 wherein said peptide is SEQ ID NO:10.

10. The method of claim 2 wherein said peptide is SEQ ID NO: 11.

11. The method of claim 2 wherein said peptide is SEQ ID NO: 12.

12. The method of claim 2 wherein said peptide is SEQ ID NO:13.

13. The method of claim 1 wherein the erbB protein dimers that comprise p185 are p185 homodimers.

14. The method of claim 1 wherein the erbB protein dimers that comprise p185 are p185/EGFR heterodimers.

15. The method of claim 1 wherein the erbB protein dimers that comprise p185 are p185 homodimers.

16. The method of claim 1 wherein the erbB protein dimers that comprise p185 are p185/EGFR heterodimers.

17. A method of treating an individual who has a p185 mediated tumor by killing cells of the p185-mediated tumor, the method comprising the steps of:
   a) administering to said individual a peptide selected from the group consisting of SEQ ID NOS: 1–5 and SEQ ID NOS: 9–13, wherein said peptide renders cell of the p185-mediated tumor more sensitive to effects of cytotoxic chemotherapeutic agents; and
   b) administering to the individual a therapeutically effective amount of a cytotoxic chemotherapeutic agent; whereby the cytotoxic chemotherapeutic agent kills cells of the p185-mediated tumor.

18. The method of claim 17 wherein said peptide is SEQ ID NO:1.

19. The method of claim 17 wherein said peptide is SEQ ID NO:2.

20. The method of claim 17 wherein said peptide is SEQ ID NO:3.

21. The method of claim 17 wherein said peptide is SEQ ID NO:4.

22. The method of claim 17 wherein said peptide is SEQ ID NO:5.

23. The method of claim 17 wherein said peptide is SEQ ID NO:9.

24. The method of claim 17 wherein said peptide is SEQ ID NO:10.

25. The method of claim 17 wherein said peptide is SEQ ID NO:11.

26. The method of claim 17 wherein said peptide is SEQ ID NO:11.

27. The method of claim 17 wherein said peptide is SEQ ID NO:12.

28. The method of claim 17 wherein the erbB protein dimers that comprise p185 are p185 homodimers.

29. The method of claim 17 wherein the erbB protein dimers that comprise p185 are p185/EGFR heterodimers.

* * * * *

UNITED STATES PATENT AND TRADEMARK OFFICE
CERTIFICATE OF CORRECTION

PATENT NO. : 6,417,168 B1
DATED : July 9, 2002
INVENTOR(S) : Greene et al.

It is certified that error appears in the above-identified patent and that said Letters Patent is hereby corrected as shown below:

Column 134,
Lines 56-59, Claims 26 and 27 should read:
26. The method of claim 17, wherein said peptide is SEQ ID NO: 12.
27. The method of claim 17, wherein said peptide is SEQ ID NO: 13.

Signed and Sealed this

Sixth Day of July, 2004

JON W. DUDAS
*Acting Director of the United States Patent and Trademark Office*